United States Patent
Blomquist

(10) Patent No.: US 8,998,878 B2
(45) Date of Patent: Apr. 7, 2015

(54) INSULIN PUMP HAVING CORRECTION FACTORS

(75) Inventor: Michael L. Blomquist, Blaine, MN (US)

(73) Assignee: Tandem Diabetes Care, Inc., San Diego, CA (US)

( * ) Notice: Subject to any disclaimer, the term of this patent is extended or adjusted under 35 U.S.C. 154(b) by 8 days.

(21) Appl. No.: 13/477,684

(22) Filed: May 22, 2012

(65) Prior Publication Data

US 2012/0232521 A1 Sep. 13, 2012

Related U.S. Application Data

(63) Continuation of application No. 13/281,168, filed on Oct. 25, 2011, now Pat. No. 8,657,807, which is a continuation of application No. 11/582,519, filed on Oct. 17, 2006, now abandoned.

(51) Int. Cl.
| | |
|---|---|
| A61M 31/00 | (2006.01) |
| G06F 19/00 | (2011.01) |
| A61M 5/142 | (2006.01) |
| G06F 3/0482 | (2013.01) |
| G06F 3/0484 | (2013.01) |

(52) U.S. Cl.
CPC ....... *G06F 19/3468* (2013.01); *A61M 5/14244* (2013.01); *A61M 2202/07* (2013.01); *A61M 2205/35* (2013.01); *G06F 3/0482* (2013.01); *G06F 3/04842* (2013.01); *G06F 3/04847* (2013.01)

(58) Field of Classification Search
CPC ............ G06F 19/3468; G06F 19/3437; G06F 19/3481; G06F 19/3406; A61M 2230/201; A61M 2005/14208; A61M 5/172; A61M 5/1723; A61M 2005/14296; A61M 2205/52; A61B 5/14532; A61B 5/4839; G01N 33/66
USPC .......................................... 604/66
See application file for complete search history.

(56) References Cited

U.S. PATENT DOCUMENTS

| | | | |
|---|---|---|---|
| 5,455,496 | A | 10/1995 | Williams et al. |
| 5,685,844 | A | 11/1997 | Marttila |
| 5,713,856 | A | 2/1998 | Eggers et al. |
| 5,754,355 | A | 5/1998 | Nakamura et al. |
| 5,814,015 | A | 9/1998 | Gargano et al. |
| 5,822,715 | A | 10/1998 | Worthington et al. |
| 5,876,370 | A | 3/1999 | Blomquist |

(Continued)

FOREIGN PATENT DOCUMENTS

| | | |
|---|---|---|
| EP | 1102194 | 5/2001 |
| WO | WO2004093648 | 11/2004 |
| WO | WO2007065944 A1 | 6/2007 |

OTHER PUBLICATIONS

International Search Report and Written Opinion mailed Mar. 10, 2008 for International Application No. PCT/US2007/022052.

(Continued)

*Primary Examiner* — Jason Flick
(74) *Attorney, Agent, or Firm* — Patterson Thuente Pedersen, P.A.

(57) ABSTRACT

Methods of regulating blood glucose levels using an insulin pump are disclosed. A method includes receiving a current blood glucose level, and determining whether the current blood glucose level is above a threshold value. The method also includes calculating a correction bolus value based upon the current blood glucose.

21 Claims, 32 Drawing Sheets

(56) References Cited

U.S. PATENT DOCUMENTS

| | | | |
|---|---|---|---|
| 5,935,099 A | 8/1999 | Peterson et al. | |
| 5,959,418 A | 9/1999 | Gotou | |
| 5,997,475 A | 12/1999 | Bortz | |
| 6,172,474 B1 | 1/2001 | Gotou | |
| 6,188,192 B1 | 2/2001 | Chen | |
| 6,243,222 B1 | 6/2001 | Boutaghou et al. | |
| 6,285,521 B1 | 9/2001 | Hussein | |
| 6,379,301 B1 | 4/2002 | Worhington et al. | |
| 6,396,652 B1 | 5/2002 | Kawachi et al. | |
| 6,551,276 B1 | 4/2003 | Mann et al. | |
| 6,554,798 B1 | 4/2003 | Mann et al. | |
| 6,562,001 B2 | 5/2003 | Lebel et al. | |
| 6,577,899 B2 | 6/2003 | Lebel et al. | |
| 6,744,350 B2 | 6/2004 | Blomquist | |
| 6,782,291 B1 | 8/2004 | Mann et al. | |
| 6,790,198 B1 | 9/2004 | White et al. | |
| 6,819,072 B2 | 11/2004 | White et al. | |
| 6,852,104 B2 | 2/2005 | Blomquist | |
| 6,936,029 B2 | 8/2005 | Mann et al. | |
| 6,979,326 B2 | 12/2005 | Mann et al. | |
| 6,997,920 B2 | 2/2006 | Mann et al. | |
| 7,025,743 B2 | 4/2006 | Mann et al. | |
| 7,109,878 B2 | 9/2006 | Mann et al. | |
| 7,204,823 B2 | 4/2007 | Estes et al. | |
| 7,278,983 B2 | 10/2007 | Ireland et al. | |
| 7,291,107 B2 * | 11/2007 | Hellwig et al. | 600/365 |
| 7,341,577 B2 | 3/2008 | Gill | |
| 7,404,796 B2 | 7/2008 | Gensberg | |
| 7,515,060 B2 | 4/2009 | Blomquist | |
| 7,553,281 B2 | 6/2009 | Hellwig et al. | |
| 7,559,926 B1 | 7/2009 | Blischak | |
| 7,651,489 B2 | 1/2010 | Estes et al. | |
| 7,651,845 B2 | 1/2010 | Doyle et al. | |
| 7,704,226 B2 | 4/2010 | Mueller, Jr. et al. | |
| 7,734,323 B2 | 6/2010 | Blomquist et al. | |
| 7,751,907 B2 | 7/2010 | Blomquist | |
| 7,768,408 B2 | 8/2010 | Reggiardo et al. | |
| 7,806,886 B2 | 10/2010 | Kanderian et al. | |
| 7,815,602 B2 | 10/2010 | Mann et al. | |
| 7,819,843 B2 | 10/2010 | Mann et al. | |
| 7,837,647 B2 | 11/2010 | Estes et al. | |
| 7,884,729 B2 | 2/2011 | Reggiardo et al. | |
| 7,959,598 B2 | 6/2011 | Estes | |
| 7,972,296 B2 | 7/2011 | Braig et al. | |
| 8,012,119 B2 | 9/2011 | Estes et al. | |
| 8,029,459 B2 | 10/2011 | Rush et al. | |
| 8,029,460 B2 | 10/2011 | Rush et al. | |
| 8,140,275 B2 | 3/2012 | Campbell et al. | |
| 8,152,789 B2 | 4/2012 | Starkweather et al. | |
| 8,170,721 B2 | 5/2012 | Nickerson | |
| 8,192,394 B2 | 6/2012 | Estes et al. | |
| 8,192,395 B2 | 6/2012 | Estes et al. | |
| 8,206,350 B2 | 6/2012 | Mann et al. | |
| 8,208,984 B2 | 6/2012 | Blomquist et al. | |
| 8,219,222 B2 | 7/2012 | Blomquist | |
| 8,221,345 B2 | 7/2012 | Blomquist | |
| 8,221,385 B2 | 7/2012 | Estes | |
| 8,226,891 B2 | 7/2012 | Sloan et al. | |
| 8,231,562 B2 | 7/2012 | Buck et al. | |
| 8,250,483 B2 | 8/2012 | Blomquist | |
| 8,343,092 B2 | 1/2013 | Rush et al. | |
| 8,346,399 B2 | 1/2013 | Blomquist | |
| 8,414,523 B2 | 4/2013 | Blomquist et al. | |
| 8,454,510 B2 | 6/2013 | Yodfat et al. | |
| 8,467,980 B2 | 6/2013 | Campbell et al. | |
| 2002/0065454 A1 | 5/2002 | Lebel et al. | |
| 2002/0107476 A1 | 8/2002 | Mann et al. | |
| 2002/0193679 A1 | 12/2002 | Malave et al. | |
| 2003/0028089 A1 | 2/2003 | Galley et al. | |
| 2003/0032867 A1 | 2/2003 | Crothall et al. | |
| 2003/0055570 A1 | 3/2003 | Ribeiro, Jr. | |
| 2003/0130616 A1 | 7/2003 | Steil et al. | |
| 2003/0163088 A1 | 8/2003 | Blomquist | |
| 2003/0163789 A1 | 8/2003 | Blomquist | |
| 2003/0208113 A1 | 11/2003 | Mault et al. | |
| 2003/0212364 A1 | 11/2003 | Mann et al. |
| 2005/0021006 A1 | 1/2005 | Tonnies |
| 2005/0022274 A1 | 1/2005 | Campbell et al. |
| 2005/0143864 A1 | 6/2005 | Blomquist |
| 2005/0171513 A1 | 8/2005 | Mann et al. |
| 2006/0047192 A1 | 3/2006 | Hellwig et al. |
| 2006/0137695 A1 | 6/2006 | Hellwig et al. |
| 2006/0276771 A1 | 12/2006 | Galley et al. |
| 2007/0033074 A1 | 2/2007 | Nitzan et al. |
| 2007/0118405 A1 | 5/2007 | Campbell et al. |
| 2007/0287985 A1 | 12/2007 | Estes et al. |
| 2008/0004601 A1 | 1/2008 | Jennewine et al. |
| 2008/0033357 A1 | 2/2008 | Mann et al. |
| 2008/0071251 A1 | 3/2008 | Moubayed et al. |
| 2008/0097289 A1 | 4/2008 | Steil et al. |
| 2008/0103447 A1 | 5/2008 | Reggiardo et al. |
| 2008/0147004 A1 | 6/2008 | Mann et al. |
| 2008/0147050 A1 | 6/2008 | Mann et al. |
| 2008/0171967 A1 | 7/2008 | Blomquist et al. |
| 2008/0172026 A1 | 7/2008 | Blomquist |
| 2008/0172027 A1 | 7/2008 | Blomquist |
| 2008/0172028 A1 | 7/2008 | Blomquist |
| 2008/0172029 A1 | 7/2008 | Blomquist |
| 2008/0172030 A1 | 7/2008 | Blomquist |
| 2008/0172031 A1 | 7/2008 | Blomquist |
| 2008/0183060 A1 | 7/2008 | Steil et al. |
| 2008/0206799 A1 | 8/2008 | Blomquist |
| 2008/0228056 A1 | 9/2008 | Blomquist et al. |
| 2008/0287922 A1 | 11/2008 | Panduro |
| 2008/0300534 A1 | 12/2008 | Blomquist |
| 2009/0005726 A1 | 1/2009 | Jones et al. |
| 2009/0030398 A1 | 1/2009 | Yodfat et al. |
| 2009/0036753 A1 | 2/2009 | King |
| 2009/0131861 A1 | 5/2009 | Braig et al. |
| 2009/0177142 A1 | 7/2009 | Blomquist et al. |
| 2009/0177147 A1 | 7/2009 | Blomquist et al. |
| 2009/0212966 A1 | 8/2009 | Panduro |
| 2009/0254037 A1 | 10/2009 | Bryant, Jr. et al. |
| 2010/0049164 A1 | 2/2010 | Estes |
| 2010/0156633 A1 | 6/2010 | Buck et al. |
| 2010/0174266 A1 | 7/2010 | Estes |
| 2010/0198142 A1 | 8/2010 | Sloan et al. |
| 2010/0222765 A1 | 9/2010 | Blomquist et al. |
| 2010/0249530 A1 | 9/2010 | Rankers et al. |
| 2010/0262117 A1 | 10/2010 | Magni et al. |
| 2010/0274592 A1 | 10/2010 | Nitzan et al. |
| 2010/0292634 A1 | 11/2010 | Kircher, Jr. et al. |
| 2010/0295686 A1 | 11/2010 | Sloan et al. |
| 2010/0305965 A1 | 12/2010 | Benjamin et al. |
| 2011/0033833 A1 | 2/2011 | Blomquist et al. |
| 2011/0040247 A1 | 2/2011 | Mandro et al. |
| 2011/0040251 A1 | 2/2011 | Blomquist et al. |
| 2011/0047499 A1 | 2/2011 | Mandro et al. |
| 2011/0071464 A1 | 3/2011 | Palerm |
| 2011/0071765 A1 | 3/2011 | Yodfat et al. |
| 2011/0092788 A1 | 4/2011 | Long et al. |
| 2011/0098637 A1 | 4/2011 | Hill |
| 2011/0098638 A1 | 4/2011 | Chawla et al. |
| 2011/0098674 A1 | 4/2011 | Vicente et al. |
| 2011/0124999 A1 | 5/2011 | Reggiardo et al. |
| 2011/0137239 A1 | 6/2011 | Debelser et al. |
| 2011/0160695 A1 | 6/2011 | Sigrist et al. |
| 2011/0208155 A1 | 8/2011 | Palerm et al. |
| 2011/0256024 A1 | 10/2011 | Cole et al. |
| 2012/0041415 A1 | 2/2012 | Estes et al. |
| 2012/0191061 A1 | 7/2012 | Yodfat et al. |
| 2012/0191062 A1 | 7/2012 | Blomquist |
| 2012/0191063 A1 | 7/2012 | Brauker et al. |
| 2012/0226124 A1 | 9/2012 | Blomquist |
| 2012/0232484 A1 | 9/2012 | Blomquist |
| 2012/0232485 A1 | 9/2012 | Blomquist |
| 2012/0232486 A1 | 9/2012 | Blomquist |
| 2012/0232520 A1 | 9/2012 | Sloan et al. |
| 2012/0239362 A1 | 9/2012 | Blomquist |
| 2012/0265722 A1 | 10/2012 | Blomquist |
| 2012/0293328 A1 | 11/2012 | Blomquist |

(56) References Cited

U.S. PATENT DOCUMENTS

2012/0296269 A1 11/2012 Blomquist
2012/0296310 A1 11/2012 Blomquist
2013/0131630 A1 5/2013 Blomquist

OTHER PUBLICATIONS

Plougmann et al., "DiasNet—a diabetes advisory system for communication and education via the internet", International Journal of Medical Informatics. vol. 64, pp. 319-330 (Dec. 2001) Abstract.
International Search Report for PCT/US2007/022048 dated Mar. 7, 2008.
International Search Report for PCT/US2007/022049 dated Mar. 7, 2008.
Application and File History for U.S. Appl. No. 13/477,666, filed May 22, 2012, inventor Blomquist.
Application and File History for U.S. Appl. No. 13/477,679, filed May 22, 2012, inventor Blomquist.
Application and File History for U.S. Appl. No. 11/018,706, filed Dec. 20, 2004 inventor Blomquist.
Application and File History for U.S. Appl. No. 11/582,852, filed Oct. 17, 2006, inventors Blomquist et al.
Application and File History for U.S. Appl. No. 11/582,841, filed Oct. 17, 2006, inventor Blomquist.
Application and File History for U.S. Appl. No. 11/582,877, filed Oct. 17, 2006, inventor Blomquist.

* cited by examiner

INSULIN PUMP HAVING CORRECTION FACTORS

RELATED APPLICATION

This application is a continuation of application Ser. No. 13/281,168, filed Oct. 25, 2011, which in turn is a continuation Ser. No. 11/582,519 filed Oct. 17, 2006, now abandoned, which is hereby fully incorporated herein by reference.

TECHNICAL FIELD

The present invention relates to insulin pumps, and more particularly, to insulin pumps having correction factors.

BACKGROUND

A large portion of the world's population suffers from diabetes. Many of these people need to take injections of insulin to normalize the level of sugar in their bodies to prevent complications. Such complications can include kidney failure, loss of circulation, and blindness. The need to manually take injections with a syringe and the process of determining the dose for various shots can be a great inconvenience and can limit a diabetic's activities and restrict their movements. Furthermore, it can be difficult to maintain a consistent level of blood glucose because there is a practical limit to the number of injections that most patients can receive.

One solution to reduce some of the problems associated with the manual injection of insulin is an ambulatory pump that delivers insulin to the diabetic user. Such insulin pumps can provide a more consistently normal level of blood glucose, which reduces the risk of complications from diabetes. However, current pumps still have practical limits to their programming that make them cumbersome to program and that limits the potential of the pump to provide even greater control over blood glucose levels.

SUMMARY

According to a first aspect, a method of regulating blood glucose levels using an insulin pump is disclosed. The method includes receiving a current blood glucose level, and determining whether the current blood glucose level is above a threshold value. The method also includes calculating a correction bolus value based upon the current blood glucose.

According to a second aspect, an insulin pump is disclosed. The insulin pump includes a pump mechanism and a memory configured to store one or more blood glucose levels. The insulin pump also includes a programmable circuit arranged to control the pump mechanism and operatively connected to the memory. The programmable circuit is programmed to receive a current blood glucose level and determine whether the current blood glucose level is above a threshold value. The programmable circuit is also programmed to calculate a correction bolus value based upon the current blood glucose.

According to a third aspect, an insulin pump is disclosed. The insulin pump includes a pump mechanism and a memory configured to store one or more rules, each rule including a threshold and a percentage. The insulin pump includes a programmable circuit arranged to control the pump mechanism and operatively connected to the memory. The programmable circuit is programmed to prompt a user to input the threshold value and the percentage for at least one rule. The programmable circuit is further programmed to receive a current blood glucose level, and determine whether the current blood glucose level is above a threshold value. The programmable circuit is also programmed to, upon determining that the current blood glucose level is above the threshold value, alter a correction bolus calculation factor. The programmable circuit is programmed to calculate a correction bolus value based upon the correction factor and deliver the correction bolus to the user.

DETAILED DESCRIPTION OF THE PREFERRED EMBODIMENT

Figure 1:
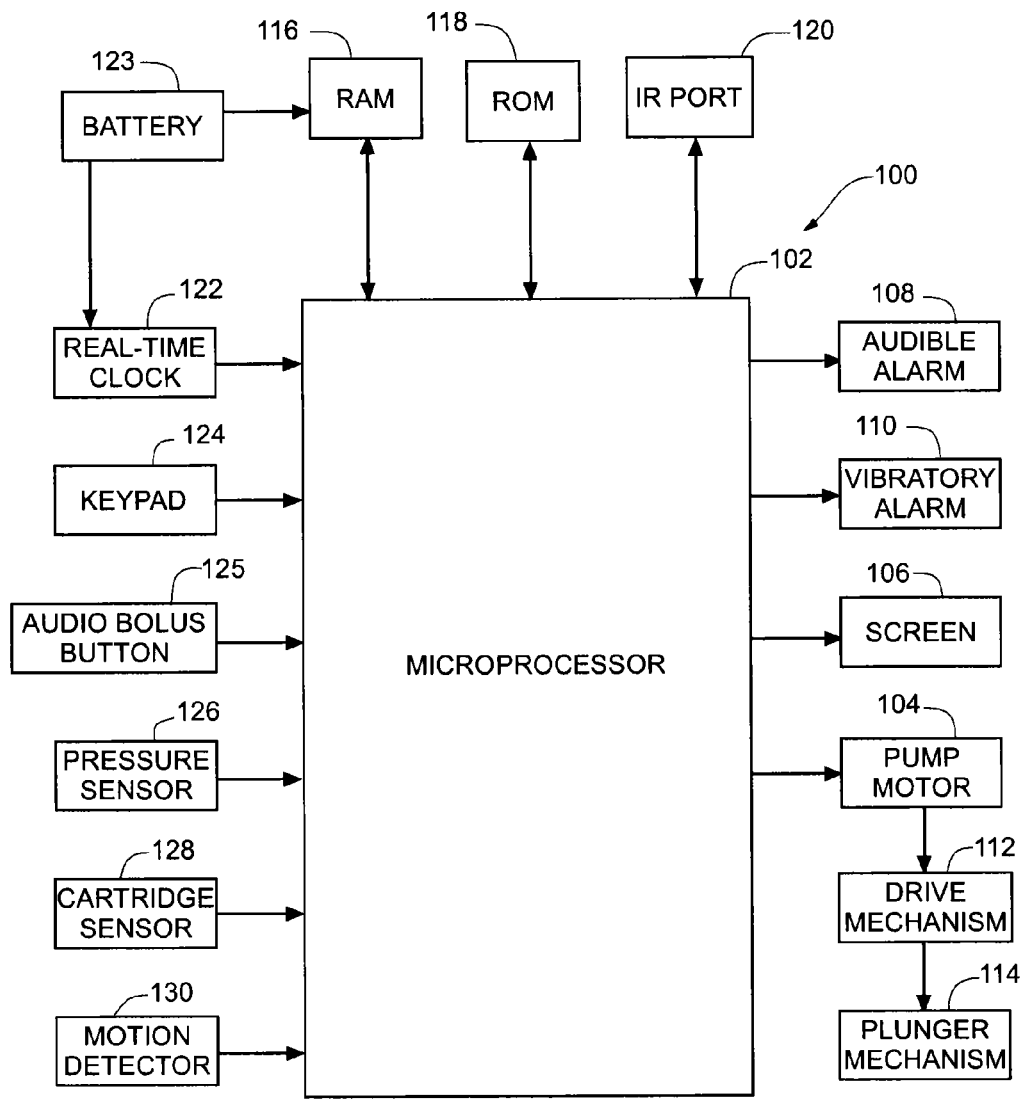
FIG. 1 illustrates the architecture of a pump that embodies the present invention.

Various embodiments of the present invention will be described in detail with reference to the drawings, wherein like reference numerals represent like parts and assemblies throughout the several views. Reference to various embodiments does not limit the scope of the invention, which is limited only by the scope of the claims attached hereto. Additionally, any examples set forth in this specification are not intended to be limiting and merely set forth some of the many possible embodiments for the claimed invention.

The logical operations of the various embodiments of the invention described herein are implemented as: (1) a sequence of computer implemented steps, operations, or procedures running on a programmable circuit within a computer, (2) a sequence of computer implemented steps, operations, or procedures running on a programmable circuit within a pump for delivering insulin; and/or (3) interconnected machine modules or program engines within the programmable circuits.

The various embodiments execute or utilize operating parameters, which customize or personalize operation of the computer implemented steps, machine modules, and programs to meet the requirements of individual pump users. The operating parameters can be numerical values, text strings, flags, argument names, or any other aspect of the insulin pump programming that the user can set to control operation of the pump.

Additionally, the pump generates and presents information and fields in user interfaces, which are also referred to as displays. The user interfaces can include fields, alpha/numeric character strings, times, and dates. The fields, also referred to as cells, prompt users to enter and/or select information. Because there is not an alpha/numeric keyboard on the pump, each of the field is associated with a spin box that includes values the user can enter into the field. The user spins or scrolls through values until the desired value is visible within the field. When the user selects the visible value it is entered into the field. The user selects a value with a Next function, Edit function, or Select function as identified herein. When the pump displays a field and the field has focus, it is said to prompt the user to select a value. Additionally, selecting a value in a field causes the pump to index focus to the next field as defined by the programmed operations or to display the next user interface as defined by the programmed operations. In an alternative embodiment, the pump has an alpha/numeric keyboard from which operating parameters can be typed directly into the pump.

The description set forth herein discusses pumping insulin. One skilled in the art will realize that many of the features, structures, and methods disclosed herein can be used with medical infusion pumps for delivering agents other than insulin. The term "user" generally applies to the person who is receiving insulin from the pump. In many contexts, however, the user could also refer to any other person such as a caregiver that is operating the pump.

A. Pump Architecture

FIG. 1 is a functional block diagram illustrating one of many possible embodiments of an insulin pump, generally identified as 100. A microprocessor 102 is in electrical communication with and controls a pump motor 104, a screen 106, an audible alarm 108, and a vibratory alarm 110. Other embodiments can use a microcomputer, or any other type of programmable circuit, in place of the microprocessor.

The pump motor 104 drives a drive mechanism 112 that pushes a plunger mechanism 114. The plunger mechanism 114 ejects insulin from an insulin cartridge (not shown). The insulin cartridge contains a supply of insulin for delivery to a patient. These mechanical components are illustrated and discussed in commonly assigned U.S. patent application Ser. No. 10/086,646, entitled Cartridge and Pump With Axial Loading, the disclosure of which is hereby incorporated by reference.

The screen 106 can have many different configurations such as an LCD screen. As explained in more detail herein, the screen 106 displays a user interface that presents various items of information useful to a patient or caregiver. The audible alarm 108 is a beeper, and an alarm provides actual alarms, warnings, and reminders. Similar to other portable electronic devices such as a cellular telephone, the vibratory alarm 110 provides an alarm to either supplement the audio alarms or replace the audio alarm when an audible beep would be disruptive or not heard. A user can selectively enable or disable the audible 108 and vibratory 110 alarms. In one possible embodiment, however, both the audible 108 and vibratory 110 alarms cannot be disabled at the same time.

The microprocessor 102 is in electrical communication with both a random access memory (RAM) 116 and a read only memory (ROM) 118, which are onboard the pump 100 but external to the microprocessor 102 itself. The microprocessor 102 can be any programmable circuit configured to execute instructions stored in the memory devices. In one possible embodiment, the microprocessor 102 includes internal memory as well. The RAM 116 is a static RAM stores that data that can change over time such as pump settings and a historical log of events experienced by the insulin pump 100. The ROM 118 stores code for the operating system and the application programs. The ROM 118 can be any type of programmable ROM such as an EPROM. In one possible embodiment, the RAM 116 has 500 kilobytes of memory capacity and the ROM 118 has 2 megabytes of memory capacity.

An infrared (IR) port 120 is in electrical communication with the microprocessor. As explained in more detail below, the IR port 120 provides data communication with an external device such as a computer for programming an application program, programming pump settings, and downloading historical data logs. The insulin pump 100 can include other types of communication ports in place of or in addition to the IR port 120. Examples of other possible communication ports include a radio frequency (RF) port or a port that provides a hard-wired data communication link such as an RS-232 port, a USB port, or the like.

A real-time clock 122 provides a clock signal to the microprocessor 102. An advantage of having a real-time clock 122 is that it provides the program with the actual time in real-time, including day of the week, so that the programs executed by the insulin pump can track and control the actual time of day that insulin delivery and other events occur. Various durations described here are used for alerts, alarms, reminders, and other functions. In one possible embodiment, the timers are formed by the real-time clock 122 and software executed by the microprocessor 102.

A battery 123 electrically connects to the real time clock 122 and the RAM 116. The battery 123 provides an alternate electricity source for the real time clock and the RAM 116 to preserve data stored in the RAM in the case of a power interruption, such as during removal of a primary battery.

A keypad 124 also provides input to the microprocessor 102. Although other possible types of keypads are possible, one type of keypad has four buttons and is a membrane-type of keypad, which provides resistance to water and other environmental conditions. The keypad 124 contains soft keys for which the function of the keys can change as a user executes different menu selections and commands.

An audio bolus button 125 provides a further input to the microprocessor 102. The audio bolus button 125 enables a bolus, such as a correction bolus or meal bolus as described herein, corresponding to a specific audible sound. In a possible embodiment, various potential audio bolus amounts correspond to unique audible sounds configured to allow a user to program the audio bolus without requiring the user to visually reference the pump screen 106.

Other inputs into the microprocessor 102 include a pressure sensor 126, which is sensitive to the pressure within a reservoir of insulin; a cartridge sensor 128, which is sensitive to the presence of an insulin cartridge; and a motion detector 130, which detects motion of a gear (not shown) in the drive mechanism 112. The pressure sensor 126, cartridge sensor 128, and motion detector 130 are described in more detail in U.S. patent application Ser. No. 10/086,646, which is entitled Cartridge and Pump With Axial Loading, the disclosure of which was incorporated by reference above.

Figure 2:
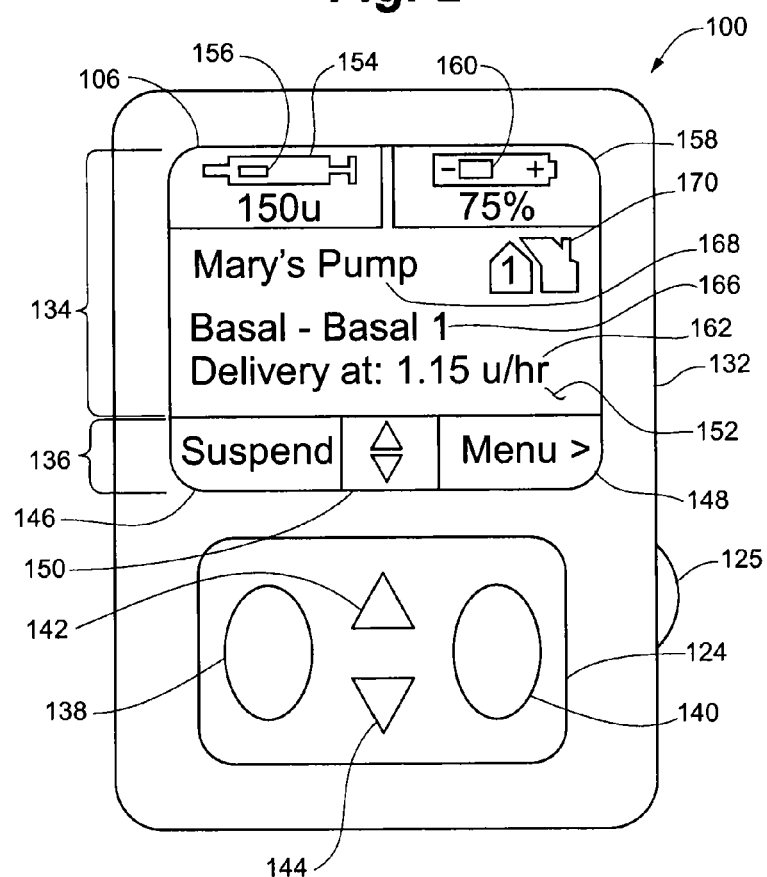
FIG. 2 is a top view of the pump shown in FIG. 1.

Referring to FIG. 2, the pump 100 is packaged in a housing 132. The keypad 124 is positioned on a first portion of the housing 132, and the screen 106 is positioned on a second portion of the housing 132. Additionally, the screen 106 has two portions, a display portion 134 and a template portion 136. A user interface is presented in the display portion 134 of the screen 106.

The template portion 136 provides a template that indicates the function assigned to each of the keys on the keypad. In the embodiment illustrated in the drawings, the keypad 124 has a first function key 138 and a second function key 140, and an up key 142 and a down key 144. The up and down keys 142 and 144 are for scrolling or spinning through operating parameters that are presented in a spin box associated with a field or between pages present within a user interface such as the home pages as described below. Additionally, a first portion 146 in the template identifies the function assigned to the first function key 138, and a second portion 148 identifies the function assigned to the second function key 140. If a variable or menu selection can be scrolled up or down, a corresponding center portion 150 of the template presents one or both of an up arrow corresponding to the scroll direction of the up key 142, and a down arrow corresponding to the scroll direction of the down key 144.

B. Home Page

In one possible embodiment, the insulin pump 100 is controlled by a menu-driven application program that is stored in the ROM 118 and executed by the processor 102. The application program also is parameter-driven in that the outcome or steps executed by the various application programs depend on the operating parameters set by the user. Examples of outcomes and steps that depend on the operating parameters include delivery rates, delivery schedules, delivery amounts, the generation and presentation of menus, and the like.

Referring still to FIG. 2, the application program presents a home page 152 in the display portion 134 of the screen 106. The home page 152 includes a first icon 154 that illustrates the amount of insulin remaining in the insulin cartridge. This first icon 154 has the shape of a syringe and a bar 156 arranged relative to the syringe shape to illustrate the amount of remaining insulin. The amount of remaining insulin also is quantified and listed below the first icon 154. A second icon 158 has the shape of a battery and has a bar 160 arranged relative to the battery-shape to illustrate the amount of remaining battery life. The percentage of remaining life on the battery is positioned below the second icon 158.

In one possible embodiment, the home page 152 presents the current status 162 of the insulin pump's 100 operation. In the example set forth in the illustration, the insulin pump 100 is delivering insulin at a rate of 1.15 units per hour according to a first basal schedule. The home page 152 also presents the name 166 of the active delivery program it is executing and personal information 168 as programmed by the user. In the illustrated example, the personal information it displays is a banner "Mary's Pump," which identifies the owner of the insulin pump 100. Other examples of information that might be included in the personal field includes medical information about the pump user similar to that information included on a medical alert bracelet such as allergies and the fact that the patient is diabetic, more detailed information about the patient including the patient's full name, telephone number, and address, detailed information about the user's caregiver such as the name and telephone number of the user's physician, and a warning that the pump 100 is an insulin pump and should not be removed from the user.

Furthermore, the pump 100 can be configured to present more than one home page. In this embodiment, the user scrolls through the home pages using the up and down keys 142 and 144. For example, other home pages might include the date, time, and amount of the last bolus delivered by the insulin pump; contact information about the patient's caregiver; medical information about the patient such as a list of the user's allergies, a warning that the user is a diabetic, and a warning that the pump is an insulin pump and should not be removed.

The pump 100 displays an icon 170 in the home page 152 to identify the displayed page as the home page. Additionally, the icon 170 can include a page number to indicate which home page is currently being displayed. One possible shape for the home page icon is an icon having the shape of a house.

C. Main Menu

Figure 3:
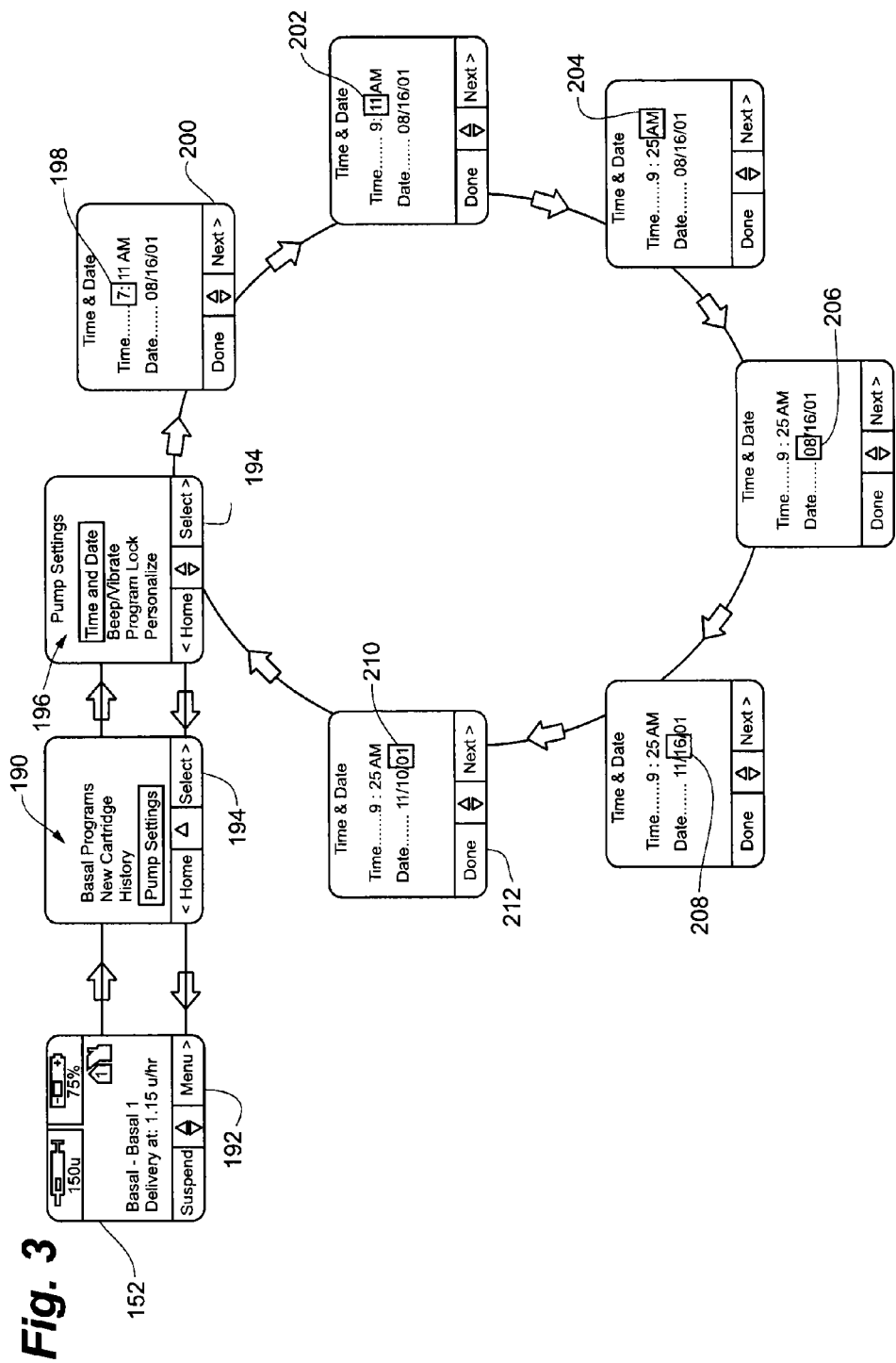
FIG. 3 illustrates setting time and date operating parameters in the pump shown in FIGS. 1 and 2.

Referring to FIG. 3, the user accesses a main menu 190 by activating a menu function 192 assigned to the second function key 140. The insulin pump 100 then displays the main menu 190, which includes a plurality of menu items that the user can select for setting operation parameters and performing various tasks as described herein. In one possible embodiment, the menu items in the main menu are Basal Programs, New Cartridge, History, and Pump Settings. In other possible embodiments, the main menu 190 can be customized to include other menu items such as Correction Bolus, Temporary Rate, Meal Bolus, and others. Furthermore, the user can customize at least some of the labels for various menu items in both the main menu 190 and submenus.

The New Cartridge menu item is selected to access the cartridge or syringe of insulin loaded in the pump 100. In one possible embodiment, selecting the New Cartridge menu item automatically sequences the user through the steps of loading the new cartridge, priming the tubing for the infusion set, priming the cannula, and setting the site reminder, if the display site reminder is enabled. The site reminder is discussed below in more detail. In yet another embodiment the user will affirmatively acknowledge each of these steps by pressing a predetermined key, either the first or second function keys 138 or 140 on the keypad 124, at the conclusion of each step, which causes the pump to index to the next step. After sequencing through each of these steps, the pump 100 prompts the user to enter an instruction whether to resume delivery of insulin.

Accessing the cartridge is discussed in more detail in U.S. patent application Ser. No. 10/086,646, entitled Cartridge and Pump With Axial Loading, the disclosure of which was incorporated by reference above.

The user selects the desired menu item by using the up and down keys 142 and 144 until the desired menu item is highlighted or otherwise marked. The user then activates the highlighted menu item by activating a select function 194 assigned to the second function key 140.

By selecting the Pump Settings menu item, the pump brings up a Pump Settings submenu 196 of several submenu items, including Time and Date, Beep/Vibrate, Program Lock, and Personalize. The Time and Date menu option is selected to set the time and date of the clock. This time and date is set in real time. When the Time and Date menu option is selected, the screen displays the time and date, and focus is placed on the hour field 198. The user scrolls through values for the hour until the desired value is set. The user then activates a next function 200 assigned to the second function key 140 to index through the remaining fields for the time and date (e.g., the minute field 202, the am/pm field 204, the month field 206, the day field 208, and the year field 210) and set the desired values for each of these fields. The user exits the Time and Date function at any time by activating the Done function 212 assigned to the first function key 138. Activating the Done function 212 saves the current time and date settings and returns the pump to the Pump Settings submenu 196.

D. Beep/Vibrate

Figure 4:
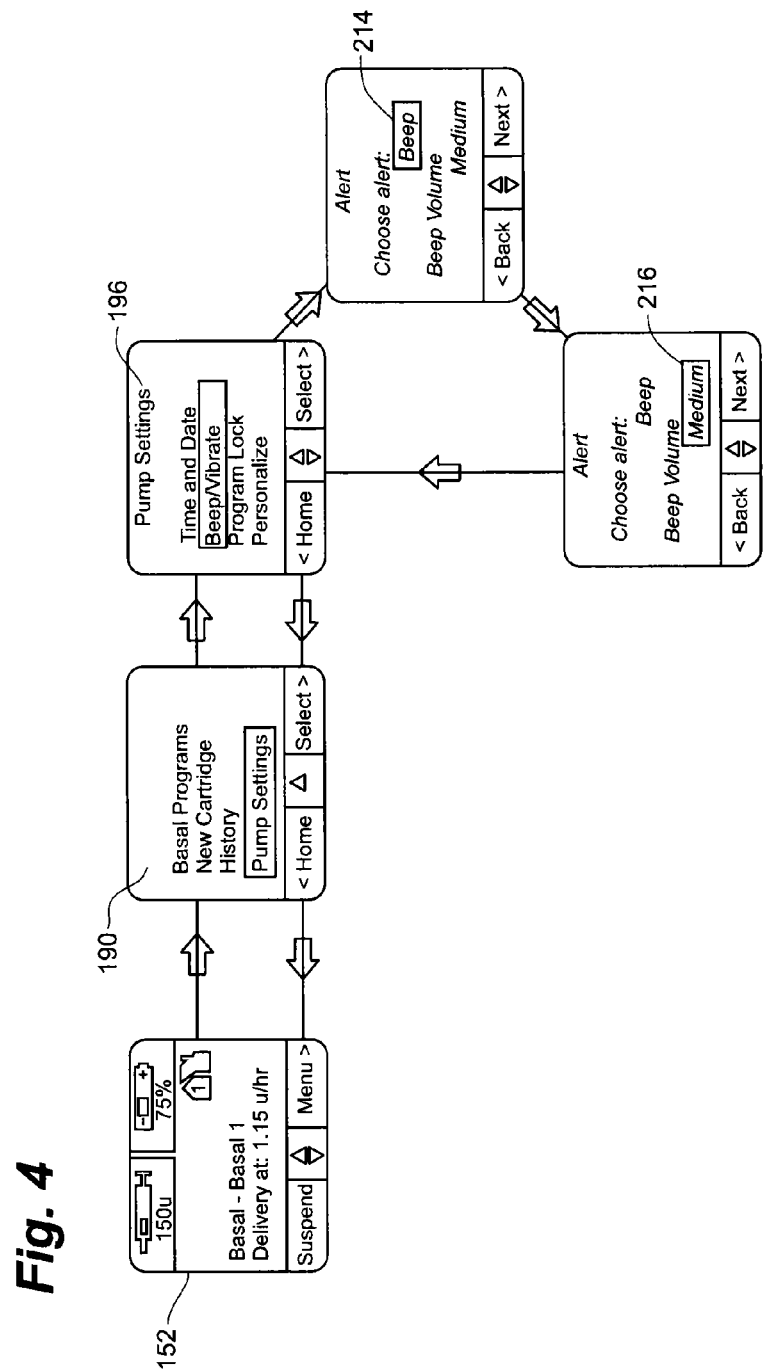
FIG. 4 illustrates setting alert styles in the pump shown in FIGS. 1 and 2.

Referring to FIG. 4, to configure an alarm function to generate either an audible or vibratory signal, the user selects the Beep/Vibrate menu option within the Pump Settings submenu 196. The pump 100 then indexes to the next user interface and places focus on a choose-alert field 214. The user scrolls to the desired beep setting or vibrate setting and selects that setting by activating the Next function 200 to select the desired setting. If the Beep setting is selected, focus changes to a beep-volume field 216 and the user scrolls to and selects the desired volume level. In one possible embodiment, the volume levels from which the user can select are low, medium, and high. Other embodiments use a numbered volume scale, labels such as indoor and outdoor, and the like. Upon selecting the desired volume level, the alert and volume settings are saved and the Pump Setting submenu 196 is displayed on the screen 106. If the user selects vibrate in the choose-alert field 214, the pump 100 will return directly to the Pump Setting submenu 196.

E. Navigation Sounds

Audible sounds generated by the pump 100 provide assistance to the user in navigating through the pump menus. The audible sounds provide a method by which a user need not rely on visually observing the pump screen while programming the pump. Such a feature can be used by visually impaired users, or users who do not wish to otherwise visually confirm the pump settings. In various embodiments of the pump 100, the sounds indicate the current screen displayed by the pump, and also signify buttons depressed on the pump or other pump events.

The pump 100 uses the home screen 152 as a basis for navigating through the pump menus by providing a unique audible sound, such as a beep of a unique pitch as compared with other sounds made by the pump. Additional home screens and menu screens programmed into the pump are associated with beeps of varying pitches. For example, the home screen 152 is associated with a first sound, which is emitted when the pump first displays the home screen, as well as each time a user navigates back to the home screen. The main menu 190 is associated with a second sound different from the first sound, and that second sound is emitted each time a user navigates to the main menu 190. Additional sounds, different from the first and second sounds and also different from each other, are associated with other home pages and menu screens as described herein. In one embodiment, the pump emits a sound of a specific pitch upon display of one or more optional setup screens. Associating a sound with an optional screen notifies the user that they are outside the typical pump programming screens. For example, the pump 100 can emit the sound upon display of a correction bolus screen, a basal rate confirmation screen, or some other unannounced screen displayed by the pump.

Some screens programmed into the pump revert back to a home screen after a predetermined period of time elapses. A user relying on sounds to navigate through the screens will want to know when this occurs. For such screens, the pump 100 can emit a second sound which is either the same as or different from the first sound associated with the screen so as to signify that such a reversion will take place. In one embodiment, the pump 100 emits three sounds thirty seconds before the reversion takes place. In such an embodiment, the pump can also optimally emit a single sound fifteen seconds before the reversion takes place. Additional sounds of varying pitch, length, or occurrence can be used as well. For example, the same sound can be used for multiple screens, but be repeated a different number of times to indicate the occurrence of one screen or the other.

Sounds are also associated with the up and down keys 142, 144 on the pump 100 to assist in setting pump delivery rates, times, and other settings. A first sound, different from the home screen and menu screen sounds described above, is associated with the up key 142. A second sound, different from this first sound and also different from the home screen and menu screen sounds, can be associated with the down key 144. The pump emits the first or second sounds when the up key 142 or down key 144 is depressed, respectively. In one embodiment, the sound associated with the up key is of a higher pitch than the sound associated with the down key. In another possible embodiment, the up key 142 or down key 144 repeats operation when held in a depressed position by a user. In this embodiment, the sound associated with the selected key 142, 144 repeats for each instance in which operation of the key repeats. In a further embodiment, sounds of increasing pitch are associated with numerical values scrolled through using the up and down keys, such that lower values are associated with sounds of a lower pitch, and higher values are associated with sounds of a higher pitch.

When scrolling through a range of values to select a setting in a pump, at least two implementations are possible with respect to the boundaries of each range. In one implementation, pressing the up key 142 at the top of the range will cause the pump value to wrap around, to the lowest value in the range. Likewise, pressing the down key 144 at the bottom of the range will cause the pump value to wrap around to the highest value in the range. In a second implementation, pressing the up key 142 at the top of the range or the down key 144 at the bottom of the range will have no effect, causing the pump setting to remain at that maximum or minimum value. In an embodiment in which the wrap around implementation is used, a sound is emitted by the pump 100 when either one of the up or down keys 142, 144 is depressed and the wrap around condition occurs, which is different from the sound emitted when either of the up or down keys 142, 144 are depressed and the condition does not exist. This sound notifies a user that the wrap around condition has occurred without the need for visual confirmation. In an embodiment in which the "wrap around" implementation is not used, a sound is emitted by the pump 100 when a user presses the up or down key 142, 144 which is different from the normal sound emitted when one of the keys is depressed. This second sound notifies a user that depressing that key had no effect, again, without the need for visual confirmation. In various additional embodiments in which either the wrap around implementation is or is not used, the unique sound which occurs at the boundary of the range can be different if at the top of the range or at the bottom of the range. In other embodiments, additional unique sounds can be used to denote a position within the range scrolled through. For example, the pump 100 can emit a unique sound each time a value is reached that is a multiple of 10. Unique sounds for each multiple of 10, or other notable positions within the range can be used as well.

Sounds are further associated with one or more alerts and/or alarms occurring in the pump 100. These sounds can be customized so that the user hears a familiar sound upon occurrence of a specific event or alarm. For example, a missed meal alarm can be associated with a dinner bell or some other sound. In a possible embodiment, the pump emits sounds, such as numerical values or messages, in Morse code or some other audibly encoded format.

The combination of all of the sounds for the screens, menus, and keys allows a user to program the pump 100 without relying on either visual confirmation using the pump screen or otherwise having to accurately count the number of times which a key is depressed. In a possible embodiment, one or more of these sound features can be disabled. For example, some or all sounds can be disabled if a user selects the vibrate option in the choose-alert field 214 described above.

F. Pump History

Figure 5:
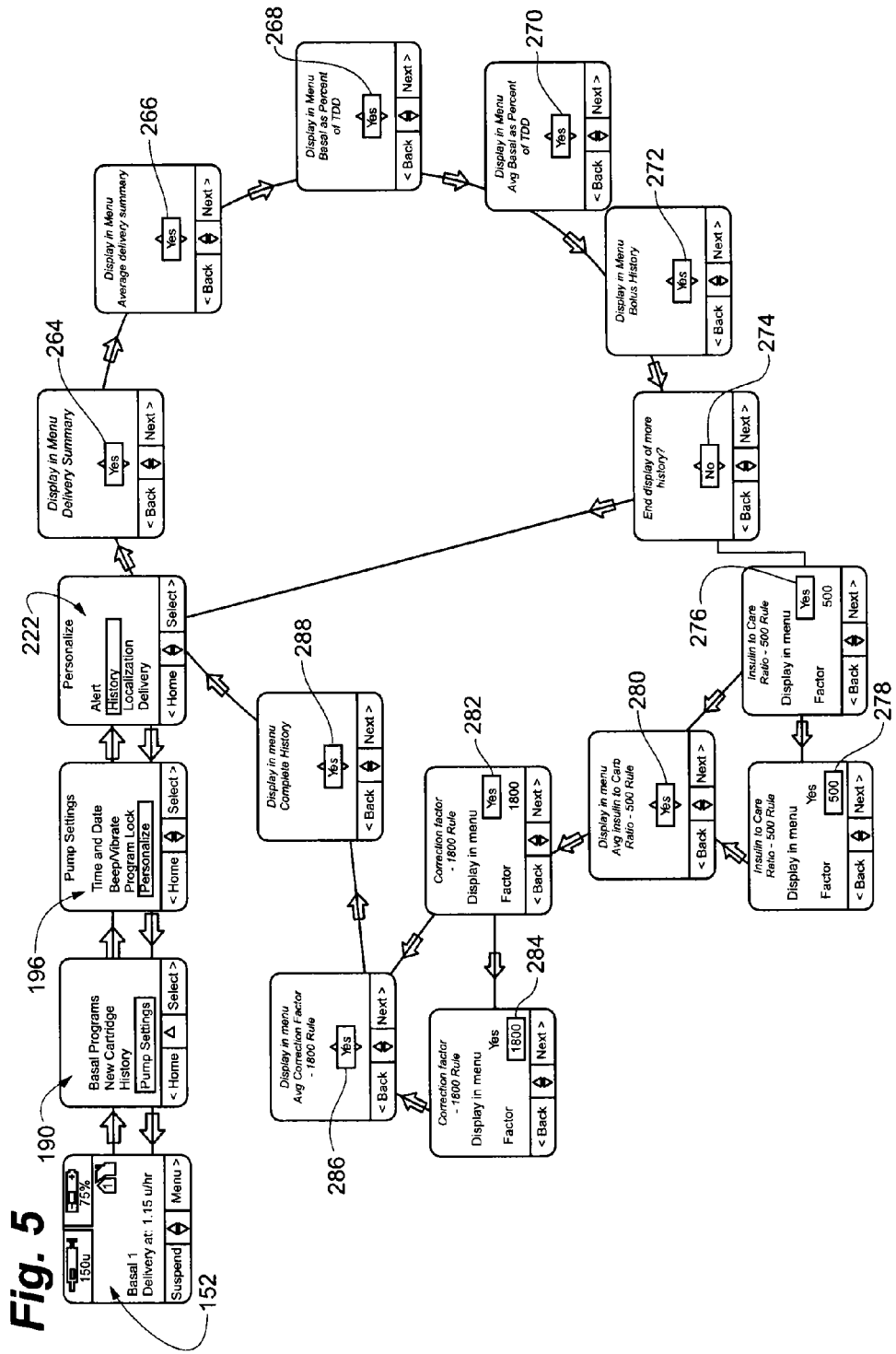
FIGS. 5 and 6 illustrate setting operational parameters related to the pump history for the pump shown in FIGS. 1 and 2.

Referring to FIG. 5, one possible embodiment of the insulin pump 100 tracks historical information related to the pump 100 such as delivery information and other events related to the pump 100. Historical information can be viewed on the screen 106 of the pump 100 or uploaded to a computer as discussed in more detail herein. The pump 100 can be customized to view historical delivery and event information in individual history screens or under the History item of the main menu 190. Additionally, the pump 100 can display delivery information either as individual events or as averages. These alternatives are only some of the possible embodiments.

The pump 100 can be programmed to track many different types of historical information, to present the historical information in many different ways, and to provide different ways to access historical information. In one possible embodiment, the historical information that the pump 100 tracks includes:

(1) The aggregate insulin delivered by the pump 100 as well as the amount of insulin broken down by insulin delivered as a meal bolus, insulin delivered to counteract estimated carbohydrates consumed by the user (if the carbohydrate estimator is used), delivered as a correction bolus, and delivered according to basal delivery protocols. In various embodiments, the pump 100 will record delivery according to basal delivery protocols as a total for all basal delivery protocols, or if the pump 100 is programmed with multiple delivery basal protocols, the delivered insulin can be broken down by each basal protocol used by the pump 100. In one possible embodiment, This data is stored as a daily total and an average daily total for a predetermined number of days. Additionally, in various embodiments, the average data can be recorded as actual average values or the average data can be calculated from the daily totals when requested for display or upon other requests.

(2) The amount of insulin delivered by the pump 100 according to a basal protocol as a percent of the total insulin delivered by the pump 100. In one possible embodiment, this data is stored as a daily percentage and an average daily percentage for a predetermined number of days. Additionally, in various embodiments, the average data can be recorded as actual average values or the average data can be calculated from the daily totals when requested for display or upon other requests.

(3) The date, time, and amount of each bolus delivered.

(4) The 500-Rule factor, which is used to estimate the grams of carbohydrates that are covered by each unit of insulin. To determine the grams of carbohydrates that are covered by each unit of insulin, the 500-Rule factor is divided by the total daily dose of insulin required to maintain the user blood sugar level in an acceptable range. The typical 500-Rule factor is 500, and hence the ratio is called the 500 Rule. However, the factor may vary for different types of insulin and from user to user and the value for the 500-Rule factor is calculated and stored. In one possible embodiment, the 500-Rule factor is stored as a daily value depending on the total delivery dose and an average value for a predetermined number of days. In an alternative embodiment, the 500-Rule factor is not stored but is calculated as the 500-Rule factor is required for a display, calculation, or other function.

(5) The 1800-Rule factor, which is used to estimate the drop in blood glucose for every unit of insulin. To determine the drop in blood glucose for each unit if insulin delivered to the user, the 1800-Rule factor is divided by the total daily dose of insulin required to maintain the user blood sugar level in an acceptable range. The typical 1800-Rule factor is 1800, and hence the ratio is called the 1800 Rule. However, the factor may vary for different types of insulin and from user to user and the value for the 1800-Rule factor is calculated and stored. In one possible embodiment, the 1800-Rule factor is stored as a daily value depending on the total delivery dose and an average value for a predetermined number of days. In an alternative embodiment, the 1800-Rule factor is not stored but is calculated as the 1800-Rule factor is required for a display, calculation, or other function.

(6) The complete history, which in one possible embodiment is the last 2000 events that are experienced by the pump, including all daily delivery totals, all alerts, all errors, all battery changes, all insulin cartridge changes, all changes to the pump program, and the like. Each record of an event includes the date and time that the event occurred. In other embodiments, a predetermined number of events other than 2000 are recorded. In yet another possible embodiment, the pump 100 records the events for a predetermined number of days rather than an absolute quantity, although there might be a limit to the total number of events that are recorded depending on available memory and other factors.

In one possible embodiment, as used herein total daily dose, also referred to as Total Daily Dose or TDD, refers to the total amount of insulin delivered during a single day including the amount of insulin delivered as a correction bolus. Other embodiments might include the amount of insulin delivered as a correction bolus in the total daily dose of insulin.

To customize how the historical information is displayed on the pump 100, the user selects the History menu item from the Personalize submenu 222. The pump 100 indexes to a delivery-summary field 264, which is placed in focus. The user scrolls to and selects the desired yes or no value. The yes value enables the Delivery Summary menu item in the History submenu 290 (FIG. 6), and the no value disables the Delivery Summary menu item in the History submenu 290. Disabled menu items are not displayed as part of the menu. In one possible embodiment, the delivery summary displayed under this menu item includes the total daily dose of insulin delivered by the pump 100 as well as the amount of insulin broken down by insulin delivered as a meal bolus, insulin delivered to counteract estimated carbohydrates consumed by the user (if the carbohydrate estimator is used), delivered as a correction bolus, and delivered according to basal delivery protocols. In an alternative embodiment, the delivery summary includes the total or aggregate amount of insulin, including insulin delivered as a correction bolus.

Upon selecting the yes or no value in the delivery-summary field 264, focus indexes to an average-delivery-summary field 266, in which the user scrolls to and selects either a yes value or a no value. The yes value enables the Average Delivery Summary menu item in the History submenu 290, and the no value disables the Average Delivery Summary menu item in the History submenu 290. In one possible embodiment, the Average Delivery Summary displayed under this menu item includes the average daily total for a predetermined number of days for the aggregate insulin delivered by the pump as well as the amount of insulin broken down by insulin delivered as a meal bolus, insulin delivered to counteract estimated carbohydrates consumed by the user (if the carbohydrate estimator is used), delivered as a correction bolus, and delivered according to basal delivery protocols.

Upon selecting the yes or no value in the average-delivery-summary field 266, focus indexes to a basal-as-percent-of-TDD field 268. In one possible embodiment, basal as a percent of TDD is the amount of insulin delivered by the pump 100 according to a basal protocol as a daily percent of the total insulin delivered by the pump 100. The user selects whether to display the Basal as a Percent of TDD menu item in the History submenu 290 using a procedure similar to that described for the Delivery Summary. Under this menu item, the pump 100 lists the total daily amount of insulin delivered as a basal as a percent of the total daily dose of insulin delivered. In an alternative embodiment, the pump 100 lists the total daily amount of insulin delivered as a bolus as a percent of the total daily dose of insulin delivered. In various embodiments, the bolus as a percent can be listed as the meal bolus as a percent of the total daily dose of insulin delivered, correction bolus as a percent of the total daily dose of insulin delivered, or total bolus as a percent of the total daily dose of insulin delivered. The pump 100 then indexes focus to an average-basal-as-percent-of-TDD field 270. In one possible embodiment, average basal as a percent of total daily delivery (TDD) is the amount of insulin delivered by the pump 100 according to a basal protocol as an average daily percent over a predetermined number of days of the total insulin delivered by the pump 100. The user selects whether to display the Avg Basal as a Percent of TDD menu item in the History submenu 290 using a procedure similar to that described for the Delivery Summary. The pump 100 lists the average basal as a percent of the total daily delivery under this menu item.

The pump 100 then indexes focus to a bolus-history field 272. In one possible embodiment, the Bolus History is the date, time, and amount of each bolus delivered. The user selects whether to display a Bolus History menu item in the History submenu 290 using a procedure similar to that described for the Delivery Summary. The pump 100 lists the pump's 100 Bolus History under the Bolus History menu item.

The pump 100 then indexes focus to an edit-display-of-more-history field 274. The user scrolls to a yes value or a no value as desired and then activates the next function. If the user selects the no value, the pump returns to the Personalize submenu 222. If the user selects the yes value, the focus indexes to a carbohydrate-ratio field 276 in which the user scrolls to a yes value or a no value as desired and activates the Next function. Selecting the yes value causes the pump 100 to display a Calc 500 Rule menu item in the history submenu 290 and to display the calculated carbohydrate ratio. The pump indexes focus to a 500-rule-factor field 278 when the user selects yes in the 500-rule-factor field 276. The user then scrolls to the desired 500-Rule factor to use in various calculations and activates the Next function. In one possible embodiment, the potential factors are in the range from 400 to 600 in increments of 15. The pump 100 then indexes focus from the 500-rule-factor field to an average-carb-ratio field 280. Selecting the no value in the 500-Rule-factor field 276 disables display of the Calc 500 Rule menu item in the History submenu 290 and causes the pump 100 to index directly from the 500-rule-factor field 276 to the average-carb-ratio field 280.

Within the average-carb-ratio field 280, the user scrolls to and selects either a yes value or a no value. If the user selects the yes value, the pump 100 will enable an Avg Calc 500 Rule menu item in the History submenu 290. Under the Avg Calc 500 Rule menu item, the pump displays the average carbohydrate ratio for a predetermined number of days. In one possible embodiment, the pump 100 calculates the average carbohydrate ratio for a 7-day period. Upon selecting the yes or no value, the pump indexes focus to a correction-factor field 282.

In other embodiments, the pump calculates the average carbohydrate ratio for periods other than 7 days. For example, the range could be in the range from 2 to 90 days. In another possible embodiment, the pump 100 calculates the average carbohydrate ratio for however number of days it stores historical data. In yet another embodiment, the user can select a predetermined number of days over which to calculate and average the carbohydrate ratio.

If the user selects the yes value in the correction-factor field 282, the focus indexes to an 1800-rule-factor field 284. The user then scrolls to and selects the desired 1800-Rule factor to use in various calculations. In one possible embodiment, the potential 1800-Rule factors are in the range from 1500 to 2200 in increments of 100. The pump then indexes focus to an average-correction-factor field 286. Selecting the no value in the correction-factor field 282 disables display of the Calc 1800-Rule menu item in the History submenu 290 and causes the pump to index directly from the correction-factor field 282 to the average-correction-factor field 286.

Within the average-correction-factor field 286, the user scrolls to and selects a yes value or a no value. If the user selects the yes value, the pump 100 will enable the Avg. Calc 1800 Rule menu item in the History submenu 290. Under the Avg; Calc 1800 Rule menu item, the pump 100 displays the average correction factor for a predetermined number of days. In one possible embodiment, the pump 100 calculates the average correction factor for a 7-day period. Upon selecting the yes or no value, in the average-correction-factor field 286, the pump indexes focus to a complete-history field 288.

In other embodiments, the pump calculates the average correction factor for periods other than 7 days. For example, the range could be in the range from 2 to 90 days. In another possible embodiment, the pump 100 calculates the average correction factor for however number of days it stores historical data. In yet another embodiment, the user can select a predetermined number of days over which to calculate and average the correction factor.

Within the complete-history field 288, the user scrolls between either a yes value or a no value. The user selects yes to enable a Complete History menu item in the History submenu 290 and selects the no value to disable the Complete History menu item. Upon selecting either the yes or no value, the pump returns to the Personalize submenu. Under the Complete History menu item, the pump displays the complete body of historical information stored in RAM 116.

Figure 6:
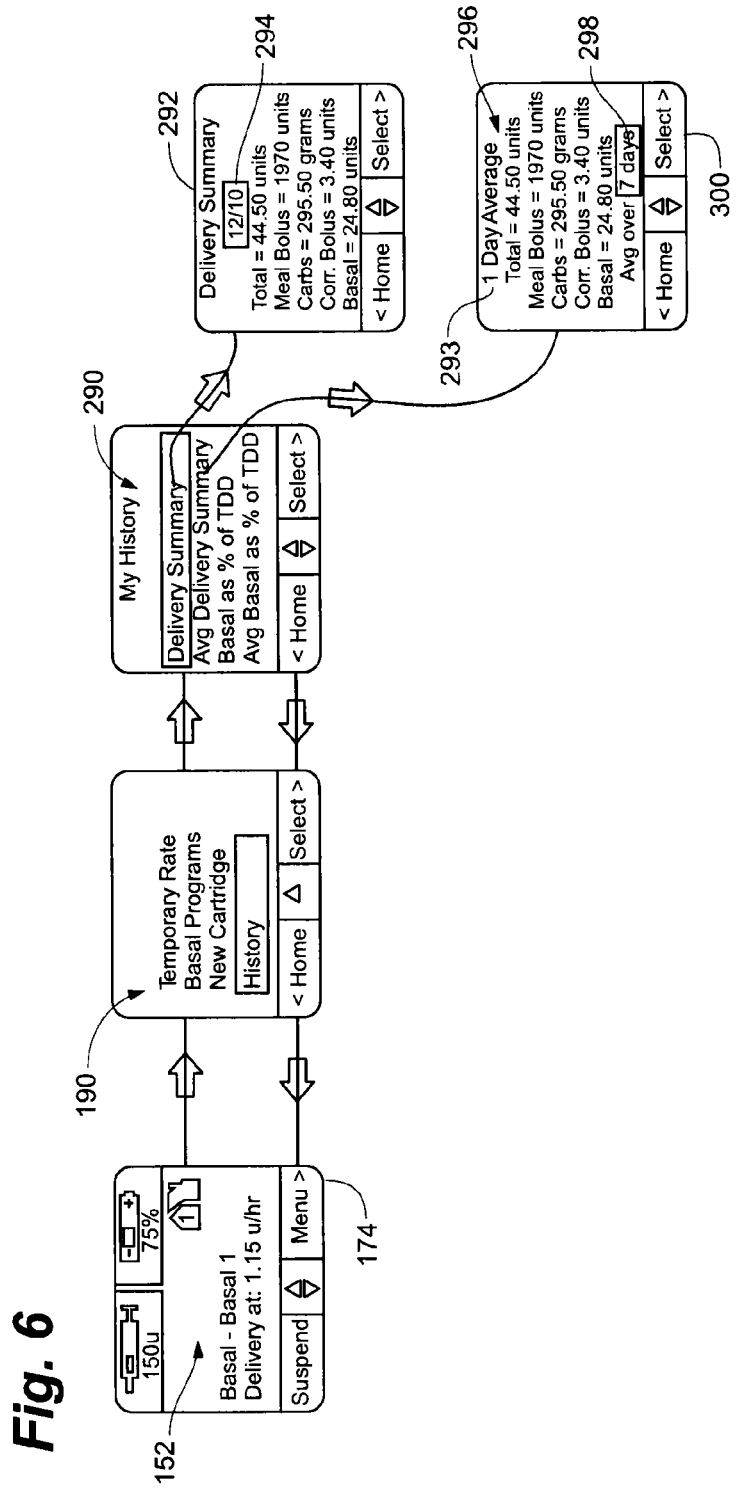

Referring now to FIG. 6, viewing historical information about the pump 100 is accomplished through the main menu 190. The user activates the Menu function 174 to access the main menu 190. Within the Main Menu 190, the user selects and activates the History menu item. The pump then indexes to the History submenu 290 that lists the historical information that is available to view on the pump 100. As described above, the historical information that is available, depending on the setting made within the History item of the Personalize submenu 222 as described above, are Delivery Summary, Avg Delivery Summary, Basal as a Percent of TDD, Avg Basal as a percent of TDD, Calc 500 Rule, Avg Calc 500 Rule, Calc 1800 Rule, and Avg Calc 1800 rule.

If the user selects Delivery Summary, the pump indexes to a Delivery Summary 292 that has a date field 294 in which the current date is listed and a Total field in which the total number of insulin units delivered is listed, a Meal Bolus field in which the number of insulin units delivered as a meal bolus is listed, a Carbs field in which the total number of carbohydrates that the user entered as an estimate of carbohydrate consumption is listed, Corr. Bolus field in which the total number of insulin units delivered as a correction bolus are listed, and a Basal field in which the total number of insulin units delivered according to the basal protocols employed by the pump are listed.

The user can scroll through dates in the date field 294 and see this historical information for dates other than the current date. In one possible embodiment, the user can scroll through the seven different dates, including the current date and the six previous dates. When the user scrolls to a different date, the pump automatically updates the historical delivery information relating to delivery that occurred on the date now listed in the date field. In an alternative embodiment, the user can scroll through the previous 90 days of data. In yet another possible embodiment, the user can scroll through however many days of data are stored on the pump 100.

If the user selects the Avg Delivery Summary menu item in the History submenu 290, the pump 100 indexes to a display 296 entitled "7 Day Average," 293 and displays the same fields (Total field, Meal Bolus field, Carbs field, Corr. Bolus field, Basal field) as the Delivery Summary display 292. However, rather than daily totals, the fields present that average number of insulin units delivered over a predetermined number of days. Additionally, in place of the date field 294, the screen for the Avg Delivery Summary presents an avg-over field 298, which contains the number of days for which the historical data is being averaged. The user can change the number of days by scrolling up or down using the up or down keys, respectively. In one possible embodiment, the number of days that can be averaged are in the range from 2-30. In another possible embodiment, the number of days that can be averaged are in the range from 2-90 days. In yet another possible embodiment, the number of days that can be averaged are in the range from 2 days to however many days of historical data are stored on the pump 100. After scrolling to a new number of days to average, the user activates an Update Function 300 and the pump 100 recalculates the averages.

If the user changes the number of days over which the average data is calculated, the title "7 Day Average" 293 changes to "X Day Average," where X is the selected number of days over which the data is averaged.

If the use selects the Basal as % of TDD item menu from the History submenu 290, the pump 100 will display a "Basal as % of TDD" display (not shown) and present the percent of total insulin delivered by the pump according to the basal delivery protocols on any given day. The Basal as % of TDD display will present a date field in which the user can change the day for which the historical information is presented in a manner similar to the Delivery Summary display 292 as described above.

If the use selects the Avg Basal as % of TDD item menu from the History submenu 290, the pump 100 will display an "Avg Basal as % of TDD" display (not shown) and present the average percent of total insulin delivered by the pump 100 according to the basal delivery protocols for a predefined number of days. The Basal as % of TDD screen will display an avg-over field 298 in which the user can change the number of days for which the historical information averaged in a manner similar to the 7 Day Summary display 296 as described above.

If the user selects Calc 500 Rule, the pump will index to a "Carb Ratio—500 Rule" display and present a table of information. In each row of the table, the pump will list a date and the calculated carbohydrate ratio for that date. The carbohydrate ratio is calculated by dividing the 500-Rule factor by the total number of insulin units delivered for that day. In one possible embodiment, the pump 100 will calculate and list the carbohydrate ratio for 30 days and the user can scroll through those values using the up and down keys. However, other embodiments will calculate and list the carbohydrate ratio for any other number of days.

If the user selects Avg Calc 500 Rule, the pump 100 indexes to an "Avg Carb Ratio—500 Rule" display. The pump 100 calculates and presents the average carbohydrate ratio for a predetermined number of days. The "Avg Carb Ratio—500 Rule" display includes an avg-over field 298 in which the user can change the number of days for which the average carbohydrate ratio is averaged in a manner similar to the "Avg Delivery Summary" display as described above.

If the user selects Calc 1800 Rule, the pump 100 will index to a "Correction Factor—1800 Rule" display and present a table of information. In each row of the table, the pump 100 will list a date and the calculated correction factor for that date. The correction factor is calculated by dividing the 1800-Rule factor by the total daily dose of insulin required to maintain the user blood sugar level in an acceptable range. In one possible embodiment, the pump 100 will calculate and list the correction factor for 30 days and the user can scroll through those values using the up and down keys 142 and 144. However, other embodiments will calculate and list the correction factor for other numbers of days.

If the user selects Avg Calc 1800 Rule, the pump 100 indexes to an "Avg Correction Factor—1800 Rule" display. The pump 100 calculates and presents the average correction factor for a predetermined number of days. The Avg Correction Factor—1800 Rule screen includes an avg-over field 298 in which the user can change the number of days for which the average correction factor is averaged in a manner similar to the "Avg Delivery Summary" display as described above.

G. Basal Rate Test

In an exemplary embodiment, the insulin pump 100 performs basal testing to determine a proper basal rate for a user of the pump. The basal rate for a pump is the rate at which the pump delivers insulin to a user, and in the exemplary embodiment correlates to the rate at which, independent of meals, the user requires insulin for normal metabolism, based on the user's particular metabolic need for insulin. The user's metabolic need for insulin is determined by testing under a controlled set of circumstances. Basal rate testing aborts under a number of circumstances, for example due to delivery of a correction bolus or a meal bolus as described herein. Also, unusual insulin levels, such as levels falling very far outside of a safe range, can cause interruption of a basal rate test or invalidation of test results for user safety reasons. A blood glucose level that is too high or too low is unsafe to the tested user and will cause the pump 100 to abort the basal rate test. Likewise, an initially high or low blood glucose level or high level of insulin on board can prevent the start of a basal rate test. Prior to and during the basal rate tests, the pump 100 notifies a user of proper behaviors for a basal rate test, as well as behaviors which can cause test failure, such as eating or delivering a correction bolus.

As described in more detail herein, the basal rate test is performed by measuring the user's blood glucose level at least at the beginning and end of a defined time period. The data representing the measured blood glucose levels and the time at which they were measured can be presented in different formats such as a table or graph.

If the difference between the beginning and ending blood glucose levels falls outside a predetermined range, the user's body is not using insulin at the same rate at which the pump is delivering it and the user can adjust the basal rate accordingly. Since a user's basal insulin needs can vary from hour to hour, the blood glucose level also can be measured at different points throughout the test and compared to the beginning blood glucose level. A difference between any of these intermediate blood glucose levels and the beginning blood glucose level also can indicate that the basal rate needs adjustment. In possible embodiments, this process can be performed iteratively until the difference between the beginning and ending blood glucose levels are within a desired range.

Since a user's basal insulin needs can change over time (weight gain or loss, change in fitness level, etc), basal rate testing may be performed periodically by users of the pump to ensure that the proper basal rate is programmed into the pump for basal delivery, discussed below. The basal testing, in general, enables four sets of scheduled alarms to define a basal test. Each set of alarms corresponds to a time segment during the day in which a user may want to check their basal delivery. For example, the set of alarms can represent times before or after meals, or at other times during a day, week, or other time period.

Figure 7:
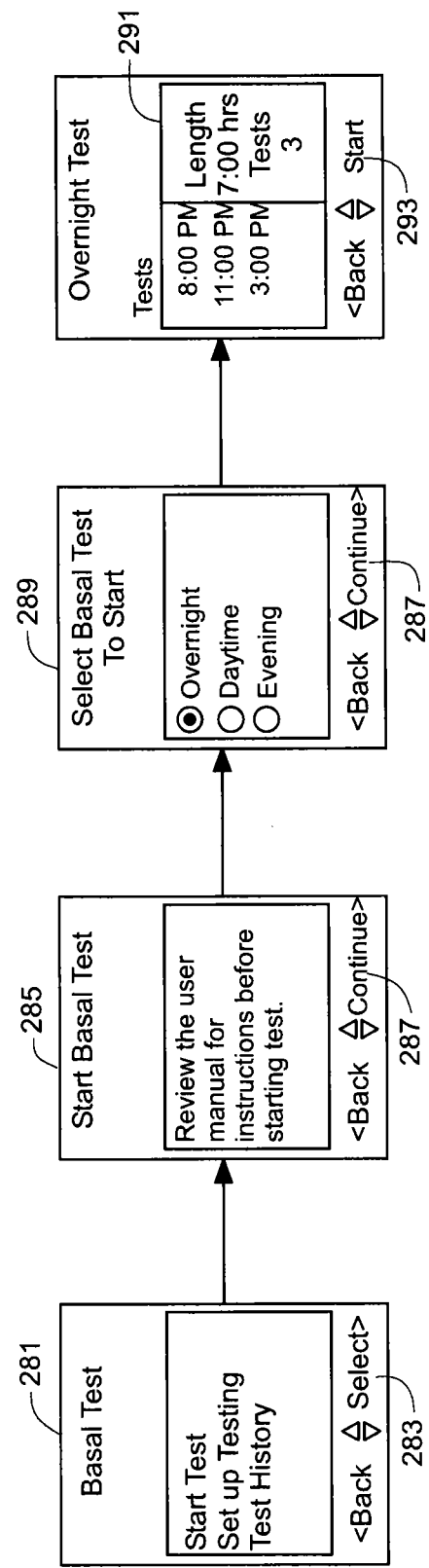
FIGS. 7-9 illustrate basal rate testing executed by the pump shown in FIGS. 1 and 2.

Referring now to FIG. 7, an exemplary implementation initiating a basal test process is shown. The pump 100 displays a basal test submenu 281, which is reached from the main menu 190. The basal test submenu 281 displays a basal test option listing, which includes a "Start Test" option, a "Set up Test" option, and a "Test History" option. The Start Test option allows the user to initiate a basal test according to the current settings in the pump, and is only visible when no other basal test has been started. The Set up Test option allows a user to set up basal test options, and is discussed in greater detail in conjunction with FIG. 8, below. The Test History option displays a test history from a currently executing or formerly executed basal test. An example of a basal test chart generated from basal test history data is shown in FIG. 9. Using the up and down keys 142, 144, the user chooses one of the options displayed on the basal test submenu 281 and chooses a select option 283. In the embodiment shown in FIG. 7, the Start Test option is selected as described.

Upon selection of the Start Test option, the pump 100 displays a start basal test screen 285. The start basal test screen 285 allows the user to confirm that a basal test is intended, and may display one or more messages to the user. The messages can include information about the basal test, about activities to avoid during the basal test, or other related information. The user confirms that a basal test is intended by selecting a continue option 287. If the basal test is not intended, a back option returns focus to the basal test submenu 281.

When the user confirms that a basal test is in fact intended, the pump 100 displays a basal test timing screen 289. The basal test timing screen 289 displays options for various predefined basal tests, such as an overnight basal test, a daytime basal test, or an evening basal test. The daytime basal test can be, for example, a morning basal test or an afternoon basal test. In the example shown, the overnight basal test is selected using the up and down keys 142, 144 and the continue option 287.

Upon selection of the desired basal test, the pump displays a listing 291 of reminder alerts which will be activated to guide the user through the basal testing process associated with that basal test. The reminder alerts represent times during the basal test process at which the user is prompted to enter their current blood glucose level. The reminder alerts can be, for example, times of the day. The listing 291 of reminder alerts can be editable by the user, so as to change the times of the day at which the reminders occur, or to change the number of reminders, as shown below in FIG. 8.

A start option 295 initiates the basal test. In the embodiment shown, a user can start a basal test at any time. However, the pump 100 only enters the basal testing state upon the occurrence of the first programmed reminder alert. Upon initiation of the test, the pump can optionally present one or more prompts or informational screens to the user to assist the user in running the basal rate test. The pump can advise the user as to optimal methods for performing the basal rate test, such as not eating for two hours prior to the test. In one possible embodiment, the one or more prompts includes a series of questions presented to the user prior to initiation of the test. The questions can be related to the user's health or sickness, activity or exercise level, stress levels, and variations of these factors from their normal levels. Other questions can be asked as well. In response to the answers provided by a user, the pump 100 may optionally display guidelines for taking a basal rate test or suggest postponement of the basal rate test. The questions and responsive answers can be included in a report, such as the one discussed below in conjunction with FIG. 9.

When the reminder alert occurs, the pump 100 prompts the user to test their blood glucose and input the blood glucose reading into the pump. Optionally, the user can select a snooze option to delay the blood glucose test by 15 minutes. The user can repeat selection of the snooze option indefinitely.

Figure 8:
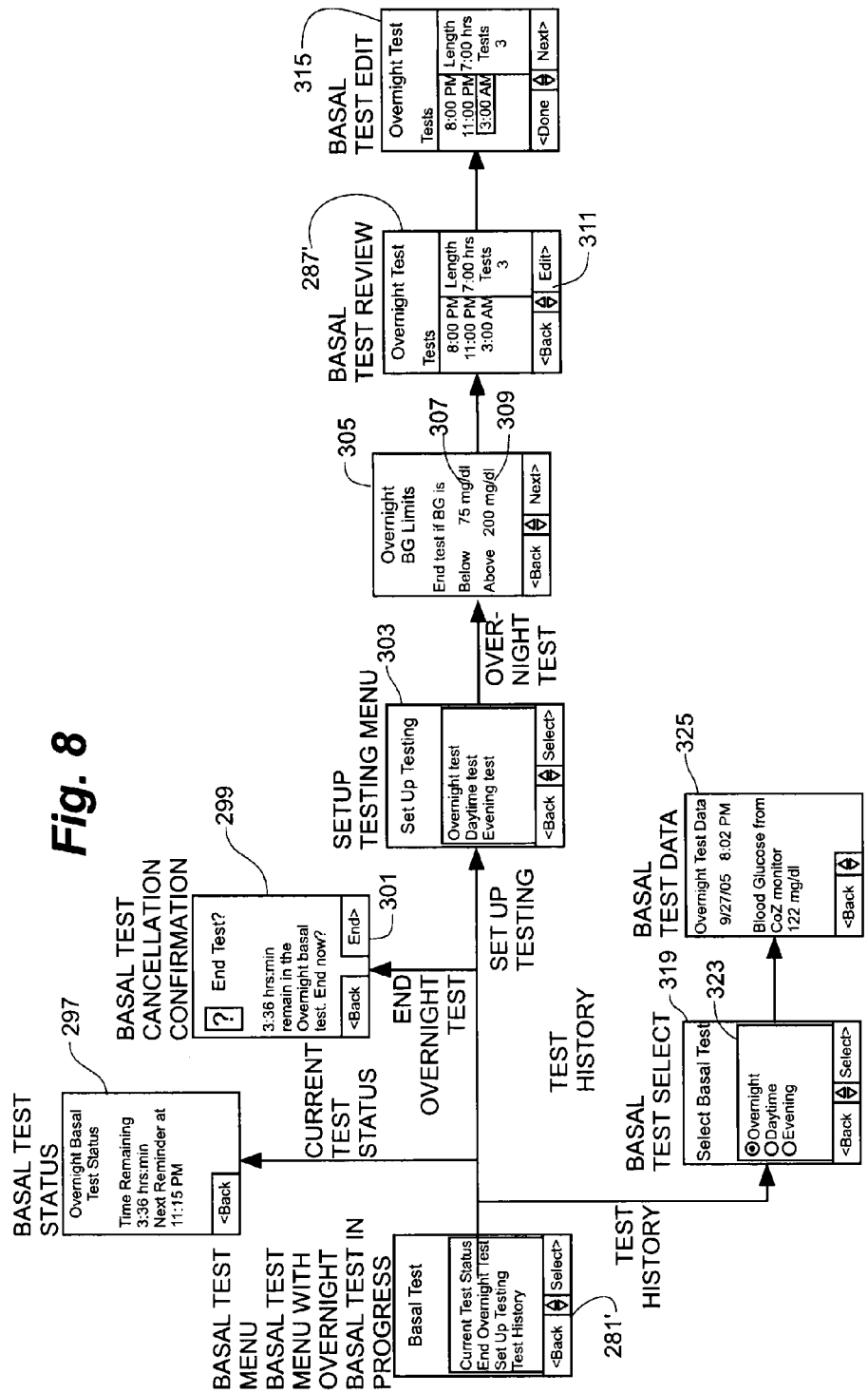
Figure 9:
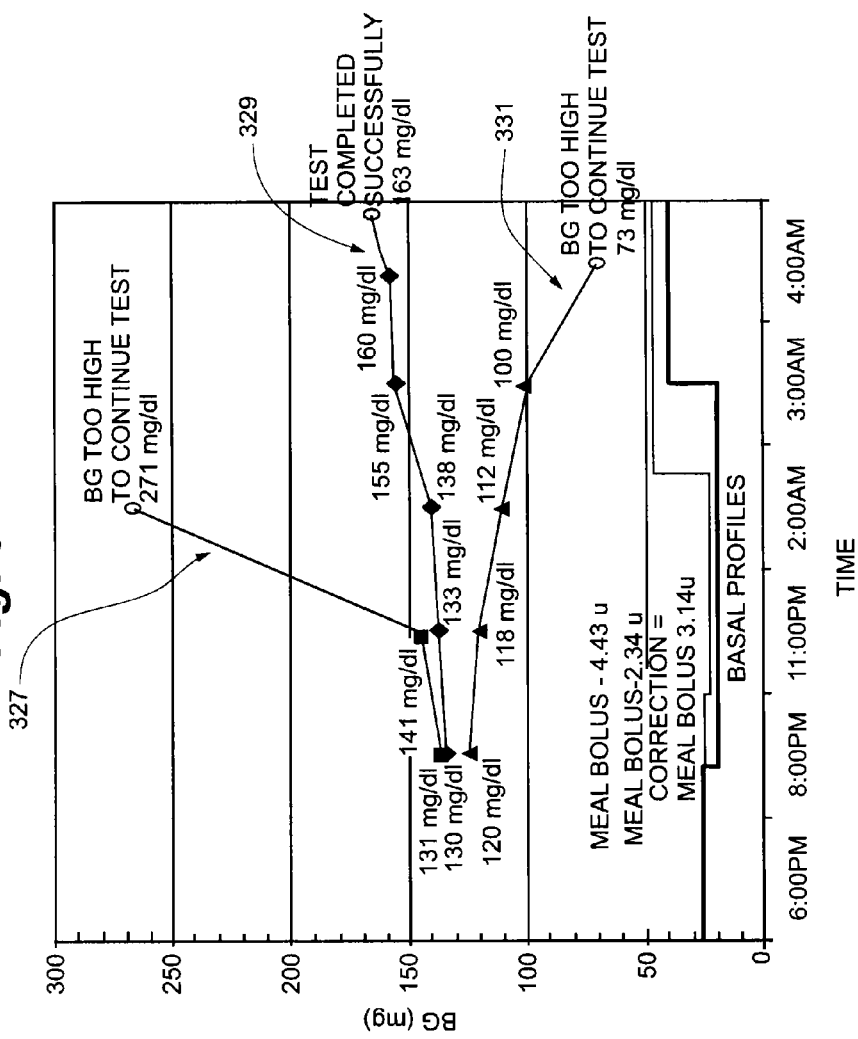

Referring to FIG. 8, the insulin pump 100 provides informational and control features related to a basal test. The screens shown in FIG. 8 are available to a user whether or not a basal test is in operation. In the example shown, the information is relates to an overnight basal test.

A basal test submenu 281' corresponds to the basal test submenu 281 of FIG. 7, but includes options related to the currently executing basal test. Basal test submenu items include the current test status, end the current test, set up testing, and test history. Additional submenu items are possible as well.

If the user selects the current test status option, the pump 100 indexes focus to a test status screen 297. The test status screen 297 displays information related to the currently scheduled test. The information can include the time remaining in the test, the time of the next reminder alarm, and other information. A back option returns focus to the basal test submenu 281'.

If the user selects the end the current test option from the basal test screen 281', the pump 100 indexes focus to an end test screen 299. The end test screen 299 asks the user to confirm that ending the test before its completion is intended. An end option 301 on the end test screen 297 confirms that the test should be aborted. A back option returns focus to the basal test submenu 281'.

If the user selects the set up testing option, the pump 100 indexes focus to a test setup screen 303. The test setup screen 303 includes navigation options to allow the user to set up a basal test and also to allow the user to set threshold blood glucose levels at which the basal test will be aborted. The user selects one of the listed tests, shown in screen 303 as "Overnight test", "Daytime test" and "Evening test". Upon selecting one of the tests, a blood glucose limit screen 305 provides the user with an interface for defining high and low threshold values, 307, 309. The user selects and edits the high and/or low threshold value 307, 309 using the up and down arrow keys 142, 144. A next option confirms the settings of the threshold values 307, 309, and causes the pump 100 to index focus to a basal test timing screen 287'.

The basal test timing screen 287' corresponds to the basal test timing screen 287 of FIG. 7, but relates to the currently selected basal test. The basal test timing screen 287' presents a list of reminder alarms represented by times of the day at which those alarms occur. The basal test timing screen 287' also presents additional information, such as the number of blood glucose tests to be performed over the course of the basal rate test, and the total elapsed time of the test. An edit option 311 allows a user to selectively edit the reminder alarms. Upon selection of the edit option 311, the pump 100 indexes focus to a basal test edit screen 315, which allows the user to edit the blood glucose thresholds included in the basal test. The user selects an existing reminder alarm using the up and down keys 142, 144, and a next option activates the alarm for editing using the up and down keys.

Default tests reside within the pump 100 and are customizable by a user. In one embodiment, the overnight test includes reminder alerts at 8:00 p.m., 11:00 p.m., 3:00 a.m., and 7:00 a.m. The daytime basal test schedule includes reminder alerts at 9:00 a.m., 12:00 p.m., 2:00 p.m., and 4:00 p.m. The evening basal test schedule includes reminder alerts at 3:00 p.m., 6:00 p.m., 9:00 p.m., and 12:00 a.m. Other times are possible as either default or customized tests as well. In one embodiment, the pump 100 does not allow editing of a basal test while the test is in progress.

The basal test terminates upon detection of any of a number of conditions. These conditions include determination that the user's current blood glucose value is outside of the range defined by the high and low threshold values, initiation of a meal bolus, initiation of a correction bolus, changing the insulin cartridge associated with the pump, changing the basal pattern, or initiation of a temporary basal rate.

If the user selects the test history option, the pump 100 indexes focus to a test selection screen 319. The test selection screen 319 prompts the user to select the type of test for which to review the test history. A test listing 323 within the test selection screen 319 displays the programmed tests and corresponding radio buttons, allowing the user to select one of the tests by using the up and down keys 142, 144. The test types include the types of tests executable by the pump, such as an overnight test, daytime test (such as a morning or afternoon test), or evening test. Each test differs by the timing of the set of reminder alerts associated with the test. Upon user selection of one of the types of tests, the pump 100 indexes focus to a test data screen 325 which displays one or more of the tests of that type which have been performed by the pump. In one embodiment, the pump 100 displays data related to the last three instances in which the test was run. In a possible embodiment, the data includes the date, the time, and the user's blood glucose level at the time of the last blood glucose test.

Referring to FIG. 9, an exemplary chart graphically displaying three different hypothetical examples of executed overnight basal tests is shown. The chart displays the time of day along the horizontal axis, and the user's blood glucose level along the vertical axis. First, second, and third data sets 327, 329, and 331 represent separate hypothetical overnight tests, and include data points at alarm times of 8:00 p.m., 11:00 p.m., 2:00 a.m., 3:00 a.m., and 4:00 a.m., which are, for example, set in the basal test timing screen 307 of FIG. 8. First data set 327 includes only the first three data points, because at 2:00 a.m. the pump 100 detected a blood glucose level above the accepted range for the test, and the test aborted. Second data set 329 represents a successfully completed test. Third data set 331 includes five data points, but did not complete operation due to detection of a blood glucose level below the accepted range for the test, resulting in canceling of the test. Upon detection of a blood glucose reading outside the threshold range programmed into the pump 100, the pump displays either an alert indicating that the user's blood glucose is either too high or too low. The pump 100 optionally instructs the user to follow physician's instructions to remedy the abnormal blood glucose value. For example, a user executing a basal rate test resulting in the first data set 327 might be instructed to increase the basal insulin rate for a subsequent test. Conversely, a user executing a basal rate test resulting in the third data set 331 might be instructed to decrease the basal insulin rate for a subsequent test. In a possible embodiment, the pump 100 graphically displays the suggested adjustment to the user's basal profile. Displaying the change in the user's basal profile can show the user the effect of the changed basal rate on blood glucose values.

Referring back to FIGS. 7-9, in one embodiment the basal test process cannot be completed simultaneously with the application of a correction bolus or other non-basal rate effect caused by the pump 100. Events that cause the basal test to terminate include a correction bolus, a meal bolus, changing the insulin cartridge, disabling the threshold values, or editing the basal pattern. Additional options can abort the basal test as well.

In one possible embodiment of pump 100, the basal rate testing is performed by prompting a user to input blood glucose values at scheduled times during the test. In an alternate embodiment, the pump 100 communicatively links to a blood glucose sensor. In such an embodiment, the pump 100 optionally requests blood glucose level information from the blood glucose sensor at various times during the test. The various times during the test can include the scheduled times during which manual or automated blood glucose test result entry would be expected, and can also include a periodic request to a blood glucose sensor. For example, the periodic request can occur every ten minutes or some other period, and may be a user-selectable period. The pump 100 would receive the most recent test result obtained by the blood glucose sensor. In embodiments including a communicative link to a blood glucose sensor, the user need only be interrupted when an abnormal blood glucose level is detected so that appropriate corrective action is taken H. Basal Rate Delivery Referring to FIG. 10, the insulin pump 100 can deliver insulin either according to a basal rate or as a bolus. In one possible embodiment, the pump 100 can deliver insulin according to four different basal delivery programs. To customize the basal delivery programs, the user accesses the Personalize Delivery submenu 222.

Selecting the Delivery menu item in the Personalize submenu 222 causes the pump to index to a Personalize Delivery submenu 302 in which the user can select the type of bolus or basal delivery protocol to edit. Selecting the Basal Program menu item causes the pump 100 to index a maximum-basal-rate field 304, which is placed in focus. Within the maximum-basal-rate field 304, the user scrolls to and selects the desired maximum basal rate. In one possible embodiment, the maximum basal rate values are in the units of u/hr and the user can scroll through values in the range from 0.5 u/hr to 36 u/hr in increments of 0.5 u/hr. When the desired maximum basal rate is selected, focus indexes to a review/edit-basal-programs field 306 in which the user selects either a yes or a no value. If the user selects the no value, the insulin pump 100 returns to the Personalize Delivery submenu 302.

If the user selects the yes value, the pump 100 indexes to a display 308 entitled "Select Program" and lists the name 310 for each of the basal programs, Basal 1, Basal 2, Basal 3, and Basal 4. A check box 312 is also displayed next to each name 310 for the basal delivery programs. If a Basal program is enabled, the check box 312 next to its name is set. If a Basal program is not enabled, the check box 312 next to its name is cleared. The name 310 of each enabled basal-delivery program is displayed as a menu item in the Basal Programs submenu 318 (FIG. 12) and the user can selectively activate the enabled programs.

To enable or disable a basal program, the user scrolls to the desired basal program and activates the Edit function 254. The pump 100 indexes to a display 313 entitled "Basal 1," where "Basal 1" is the name of the basal program being edited. The display has two fields, an enable field 314 and a name field 316. Within the enable field 314, the user selects either a yes value or a no value. If the user selects the no value, the pump 100 disables the basal program associated with the screen 313 (Basal Program 1 in the illustrated example) and returns to the Select Program display 308. The check box 312 for the disabled program is cleared. In one possible embodiment, if the pump 100 is actually executing the basal program that the user attempts to disable, the pump 100 will not disable the program and will present an error message stating, "You may not disable the active program."

If the user selects the yes value in the enable field 314, the pump 100 indexes focus to the name field 316. Within the name field 316, the user can assign a custom name to the basal-delivery program. In one possible embodiment, the user can scroll through names that are preloaded into the pump 100. Examples of names might include Weekday, Weekend, Sick Day, Travel, Monthly, and the generic names such as Basal 1, Basal 2, etc. When the user has scrolled to the desired name, the user activates the Next function and the pump 100 returns to the Select Program display 308. The check box 312 for the program that was just edited is set to indicate that the basal program is enabled. Additionally, the name selected in the name field 316 is displayed in the Select Program display 308 in place of the previously assigned name. The name selected in the name field 316 is also displayed as a menu item in the Basal Programs submenu 318.

The user repeats this procedure from the Select Program display 308 for each basal program 310 for which he or she desires to change the enabled state and/or name. When the user is done changing the enabled states and program names for the various basal programs 310, the user activates the Done function 212. The pump 100 then returns to the Personalize Delivery submenu 302. As described below, the names of the enabled basal delivery programs will then appear the Basal Programs submenu 318.

In an alternative embodiment, within the display entitled "My Program X," the user can access a spin box in which they scroll through a list of optional names and select a custom name for the enabled basal delivery programs. The selected name would then replace the generic name (e.g., Basal 1, Basal 2, Basal 3, and Basal 4 in the illustrated example) for the program associated with the display. Examples of optional names that might be loaded in the pump 100 include weekday, weekend, sick, and monthly (which is to designate a basal delivery program set for a woman's menstrual cycle).

Figure 11:
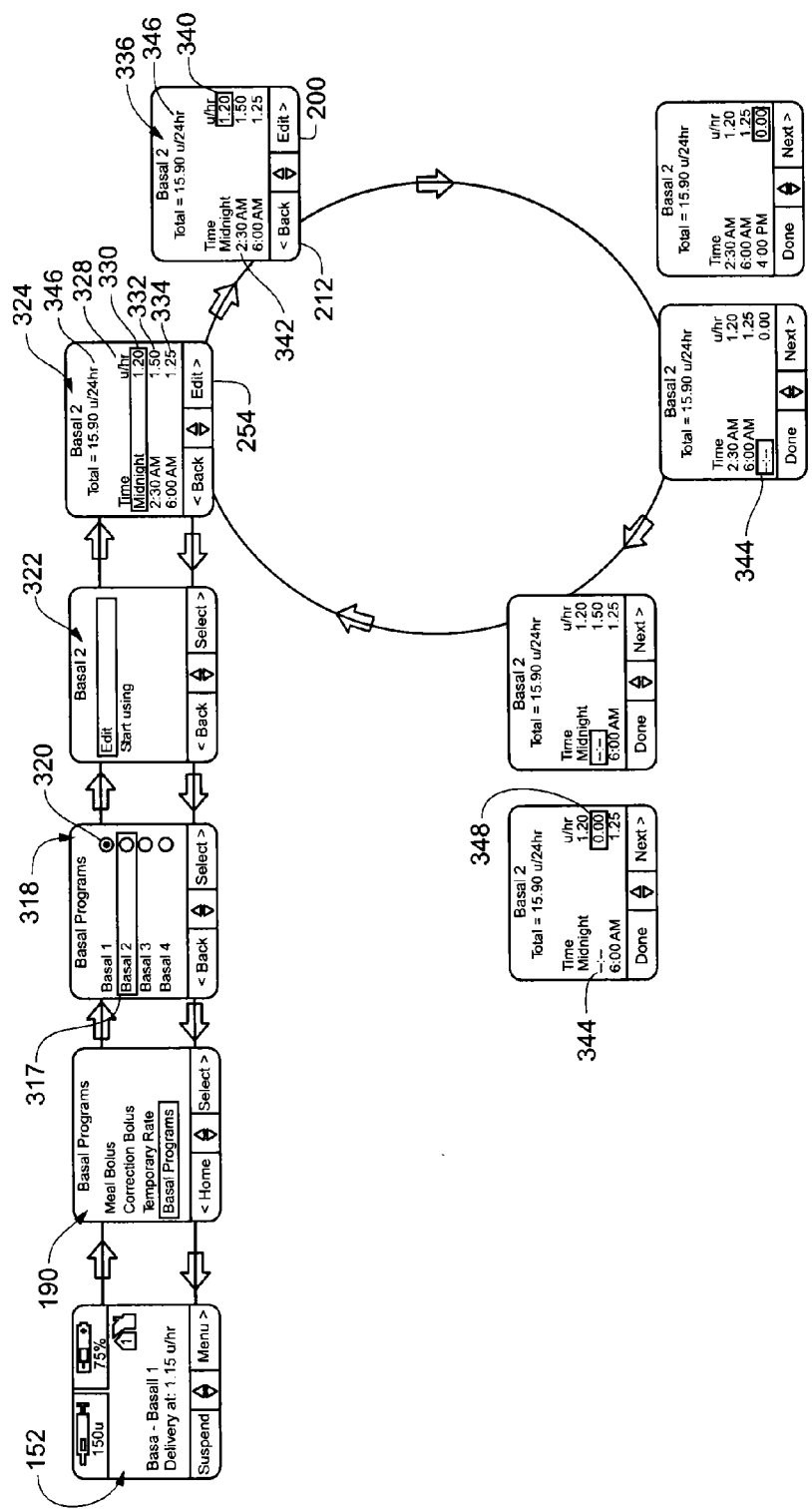

Referring now to FIG. 11, the user can edit the operating parameters for the delivery protocols assigned to each of the enabled basal programs. From the main menu, the user selects the Basal Programs menu item. The pump then indexes to a Basal Programs submenu 318 that lists those basal programs 317 that have been enabled as menu items. Each Basal Delivery program listed in the submenu 318 is identified by the name assigned to that particular program (e.g., Basal X, Weekend, Weekday, Sick Day, Travel, Monthly). In the illustrated example, all four basal programs are enabled and identified by the generic name Basal X. Additionally, there is button 320 next to each of the menu items (names for the enabled basal programs). The buttons 320 associated with the active basal program are set, and the buttons for the other basal delivery programs are cleared.

To edit a basal program, the user scrolls to and selects the desired basal program. The pump 100 indexes to a submenu 322 for which the title is the same name as the selected basal program. The menu has two menu items, an Edit menu item and a Start Using menu item. The user selects the edit menu item and the pump 100 indexes to a Summary user interface 324 that presents a table in which each row identifies a start time 326 and a scheduled delivery rate 328 for each time interval in the basal program. In the illustrated embodiment, there is a first time interval 330 having a start time and a delivery rate, a second time interval 332 having a start time and a delivery rate, and a third time interval having 334 a start time and a delivery rate. The start times are listed in a start-time field, and the delivery rates, are listed in a delivery-rate field.

Figure 10:
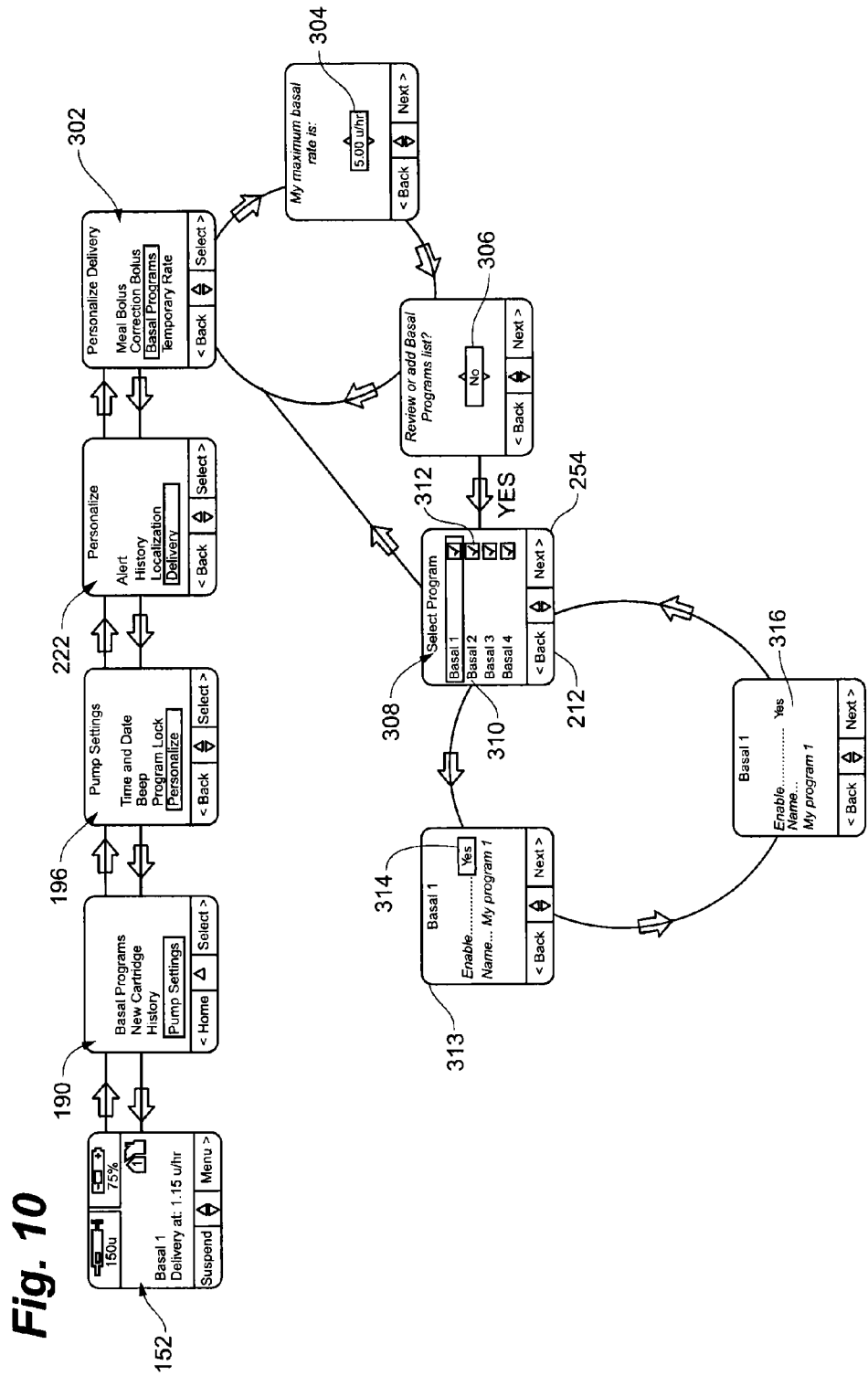
FIGS. 10-12 illustrate setting operational parameters for the basal rate delivery programs executed by the pump shown in FIGS. 1 and 2.

To edit the start times and the delivery rates, the user activates the edit function 254 in the Summary user interface 324 and the pump 100 indexes to an Edit user interface 336 and assigns the Done function 212 to the first function key 138. Additionally, the pump 100 places focus on the delivery-rate field 340 for the first interval 330. The user scrolls to and selects the desired delivery rate. The user selects the desired delivery by scrolling to the desired value and activating the Next function 200. In one possible embodiment, the pump 100 scrolls through delivery rates in the range from 0 u/hr to 2 u/hr in increments of 0.05 units per hour. The delivery rate does not exceed the maximum delivery rate (FIG. 10, Item 304).

When the desired delivery rate is selected, the pump 100 indexes focus to the start-time field 342 for the second time interval 332. The user scrolls to and selects the desired start time. In one possible embodiment, the pump 100 scrolls through start times in increments of 30 minutes. In one possible embodiment, the start time cannot be earlier than or equal to the start time of the previous time interval and cannot be later than or equal to the start time of the next subsequent time interval. Other embodiments will implement different scrolling increments and limitations on the start time that can be selected. In another embodiment, if a selected start time is not in sequence, the pump 100 will automatically reposition the delivery intervals so they are in chronological order.

When the desired start time is selected, pump 100 then indexes focus to the delivery-rate field 340 for the second time interval 332, which the user sets using the procedures described above with respect to the first time interval 330. The user continues this procedure indexing through the start times for each of the time intervals and their associated delivery rates until the start time for each of the delivery intervals and their associated delivery rates are set. When the user is finished setting and/or editing the start times and delivery rates for the various intervals, he or she activates the Done function 212 and the pump 100 returns to the Summary Display 324.

In one possible embodiment, the first time interval 330 always starts at 12:00 midnight. In this embodiment, the last time interval will terminate at 12:00 midnight. If, within the Summary Display 324, the user highlights and selects the first time interval 330 for editing, the pump 100 indexes to the Edit display 336 and initially highlights the delivery rate 328 for the first time interval 330 rather than the start time 326. In another embodiment, however, the user can change the start time 320 for the first time interval 330. The last time interval would then extend until the start time for the first time interval 330. Additionally, within the Summary Display 324, the user can scroll to a delivery interval other than the first interval 330 and activate the Edit function 254. In this situation, the start-time field 342 for the selected interval is initially placed into focus rather than the delivery-rate field 340.

To add a time interval to the basal program, the user continues to index through all of the time intervals and associated fields until the pump generates a new delivery interval and displays the characters "--:--" 344 in the start-time field 342 of the new interval, which occurs after indexing through the delivery-rate field 340 for the last time interval. The user then scrolls through desired start times for the new time interval. After the desired start time is selected, the user activates the Next function 200 and the pump 100 indexes to the delivery-rate field 340 for the new time interval, which the user sets by scrolling through available delivery rate values. The user can then activate the Next function 200 to add yet another new time interval or can activate the Done function 212 to return to the Summary display 324. In one embodiment, the pump 100 can include up to 48 time segments, although other embodiment will include more or fewer time segments.

To delete a time interval from the basal program, the user places the start-time field 342 for the desired interval into focus and scrolls down until the time reads "--:--" 344. The user then activates the Next function and the time interval is deleted and the user either activates the Next function 200 to index to another time interval for editing or activates the Done function 212 to return to the Summary display 324.

Additionally, both the Summary user interface 324 and the Edit user interface 336 include a total field 346 in which the total insulin scheduled to be delivered over a 24-hour period for that basal program is listed. The total insulin scheduled to be delivered is calculated by multiplying the delivery rate by the length of each time interval to calculate the total insulin to be delivered for each time interval by the basal program being edited. The total insulin to be delivered for each time interval is then summed to calculate the total insulin scheduled to be delivered over a 24-hour period.

Figure 12:
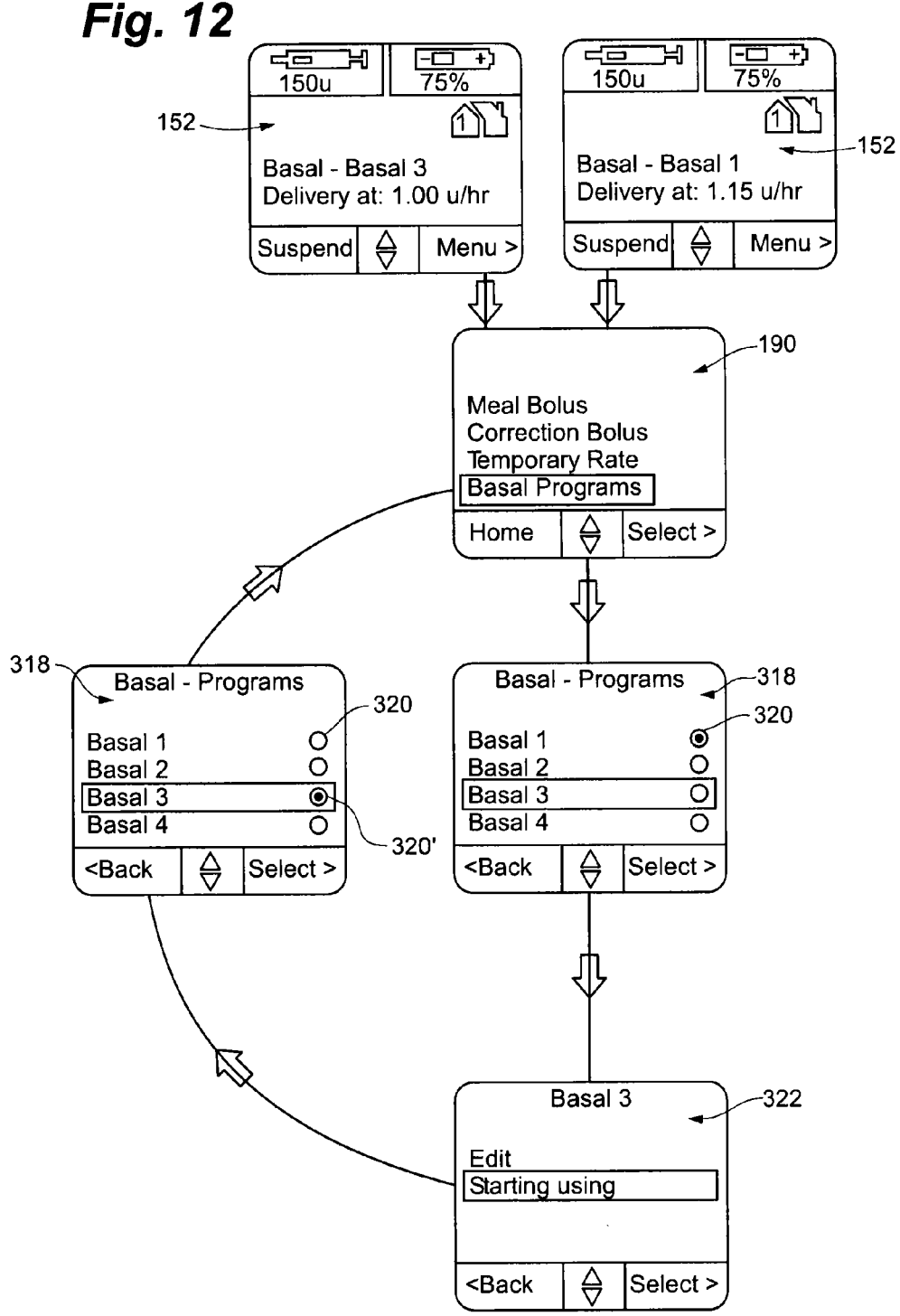

Referring to FIG. 12, to begin a basal program the user indexes to the Basal Programs submenu 318 and selects the name of the desired basal program. The pump indexes to the Basal X submenu 322 and selects the Start Using menu item. The pump returns to the Basal Programs submenu 318 and sets the button 320' for the newly activated basal program. The pump 100 also clears the button 320 for the previously active basal program.

I. Correction Bolus

In addition to delivering a basal rate the pump 100 may administer a bolus to lower the user's blood glucose level. One possible embodiment of the pump 100 can deliver two types of boluses, a correction bolus and a meal bolus. The correction bolus delivers a dose of insulin over and above the basal rate to lower or correct the user's blood glucose level if it becomes too high. A meal bolus is a dose of insulin delivered in anticipation of consuming a meal to counteract the effects that the meal may have on the user's blood glucose.

Figure 13:
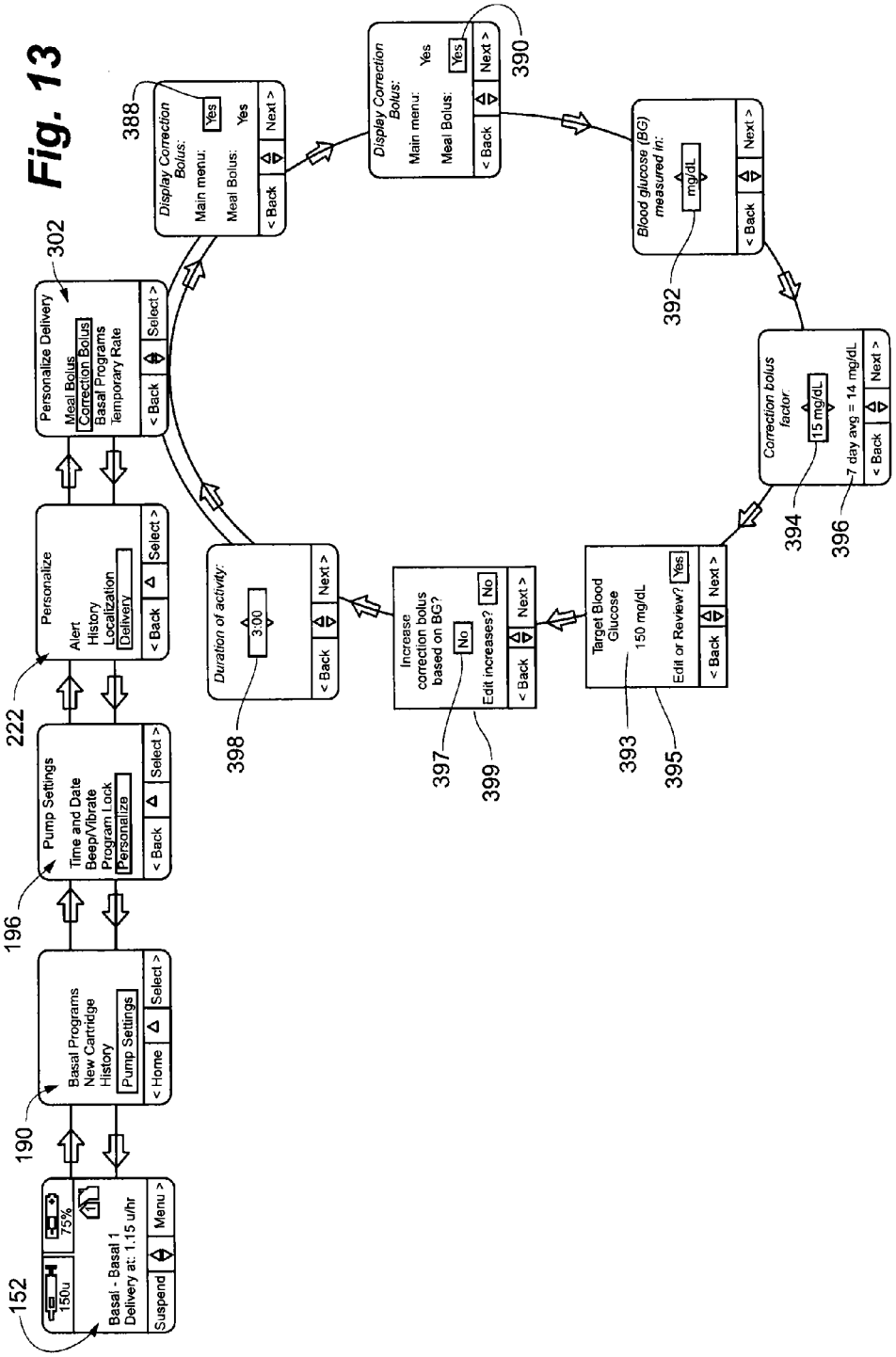
FIG. 13 illustrates setting the operational parameters for the correction bolus delivery programs executed by the pump shown in FIGS. 1 and 2.

Referring to FIG. 13, the user can personalize or customize the correction bolus program and how the program is presented in the user interface. To personalize the temporary rate programs, the user accesses the Personalize Delivery submenu 302.

Selecting the Correction Bolus menu item causes the pump 100 to display a main-menu field 388, and places it in focus. The user scrolls to and selects either a yes value or a no value. The yes value enables a Correction Bolus menu item in the main menu 190, and a no value disables the Correction Bolus menu item in the main menu 190. Upon selecting the yes or no value, focus indexes to a meal-bolus field 390 in which the user scrolls to and selects either a yes value or a no value. A yes value enables the user to set a correction bolus through the meal bolus delivery program as described below. A no value disables the ability to set a correction bolus through the meal bolus delivery program.

Upon selecting a yes or no value in the meal-bolus field 390, focus indexes to a units field 392 in which the user scrolls to and selects units for measuring blood glucose levels in either mg/dL and mmol/L. Upon selecting the units, focus indexes to a correction-bolus-factor field 394 in which the user scrolls to and selects a desired correction factor. The correction factor is the amount that the user's blood glucose drops for each unit of delivered insulin. In one possible embodiment, the user scrolls through values ranging from 5 mg/dL to 200 mg/dL (or 0.2 mmol/L to 12 mmol/L). When the desired correction factor is set, focus indexes to a target blood glucose field 393.

Additionally, the pump 100 calculates the average correction value for a predetermined number of days beginning with the previous day and extending backwards in time, and then displays 396 the average correction factor together with the correction-bolus-factor field 394. In the illustrated example, the pump 100 displays the average correction factor for the previous seven days. As discussed above, other embodiments average the correction factor over other periods of time. In yet other embodiments the user can select the period of time over which to average the correction factor.

The target blood glucose field 393 allows a user to edit or review the correction bolus blood glucose targets. An edit option 395 allows the user to optionally edit the blood glucose target values. If the user chooses to edit the blood glucose target values, they can optionally choose to set a constant target blood glucose value, or a variable target blood glucose value which changes throughout the day based on expected meal consumption, activity levels, or other factors. When the desired blood glucose targets are set or if the user chooses not to edit the blood glucose target values, focus indexes to a correction bolus adder field 397.

The correction bolus adder field 397 sets one or more correction bolus changes within the pump 100. In the field 397 shown, the correction bolus adder field prompts a user to indicate whether to increase the correction bolus delivered by the pump 100 based on the user's current blood glucose level. An edit option 399 allows the user to optionally customize the increase amount for the correction bolus based on blood glucose. The addition of insulin to the correction bolus can be a constant amount over a given threshold, can be a graduated increase based on current blood glucose, or a set of stepped increases in insulin based on blood glucose. Once one or more of the desired correction bolus adders are set, focus indexes to a duration-of-activity field 398. Within the duration-of-activity field 398, the user scrolls to and selects the duration of time over which insulin remains in the user's body. This amount will vary from user to user depending on a variety of factors including physical traits of the user and the type of insulin that is used. In one possible embodiment, the user scrolls through durations in the range from 2 hours to 6 hours. When the duration is set, the pump 100 returns to the Personalize Delivery submenu 302.

In a possible embodiment, a user selects an insulin absorption model from among multiple insulin absorption models for application by the pump 100. Insulin absorption models are used in the pump to determine the remaining insulin in a user's body a period of time after the insulin is delivered to the user, whether by a basal rate, a correction bolus, a meal bolus, or another insulin delivery method described herein. To calculate the user's insulin level, the insulin absorption model uses the programmed duration in the duration-of-activity field 398. The user optionally selects a linear or non-linear absorption model. A linear absorption model assumes a constant absorption rate of insulin into the body. A nonlinear absorption model assumes a faster absorption rate with higher insulin levels, and a lower absorption rate with lower insulin levels. The user optionally also programs a start time and tail time into the pump 100.

FIGS. 14A-14D show graphical representations of four possible insulin absorption models which can be set in the pump. The horizontal axis of the graphs represents the elapsed time since the last measured insulin on board. The vertical axis represents the insulin on board as a percentage of the total delivered insulin at the time represented by the axis.

Figure 14B:
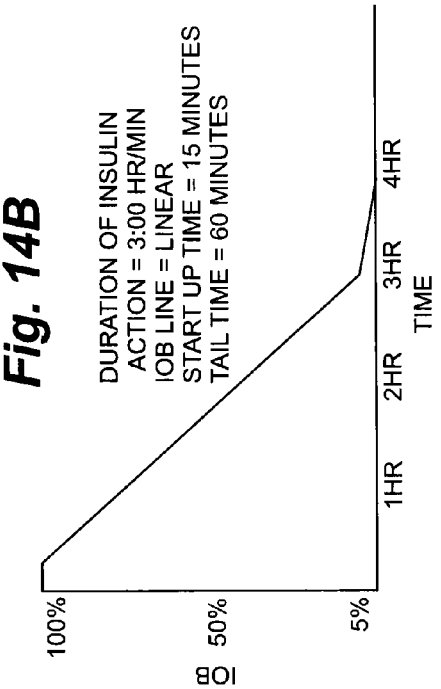
FIGS. 14A-14D illustrate insulin absorption models used in the correction bolus delivery programs executed by the pump shown in FIGS. 1 and 2.
Figure 14A:
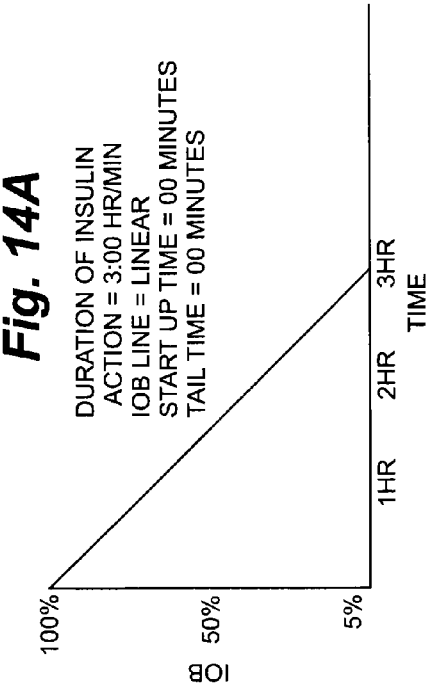

FIG. 14A shows a linear absorption model in which the programmed duration in the duration-of-activity field 398 was set to be 3 hours. The start time and tail time are either not selected or set to be zero. These settings result in a linear decrease in estimated insulin on board over three hours. The equation to be used to determine the current insulin on board (IOB) is:

$$\text{Current } IOB = \frac{\text{Initial Bolus Amount} * (\text{Duration of Activity} - \text{Elapsed Time})}{\text{Duration of Activity}}$$

For example, if a 3 Unit bolus is delivered using this selected model, at a time one and a half hours later the model estimates that the user has 1.5 Unit remaining unabsorbed within their body.

FIG. 14B shows a linear absorption model having a non-zero start time and tail time. In the embodiment shown, the start time is programmed to be 15 minutes and the tail time is programmed to be one hour. Using this model, it is assumed that insulin in a user's body does not decrease for the first 15 minutes after it is introduced. After that start period, insulin levels are assumed to decrease linearly over the set duration to a point at which approximately 5% of the introduced insulin remains. At that point, insulin levels drop to zero (either linearly or non-linearly) over the designated tail time. The equation used to determine current insulin on board using this model is:

$$\text{Current } IOB = \frac{\text{Initial Bolus Amount} * (\text{Duration of Activity} + \text{Start Time} - \text{Elapsed Time})}{\text{Duration of Activity}}$$

Note: During Start up Time, current IOB limited to Initial Bolus Amount until the Current IOB reaches 5% of the Initial Bolus Amount. At that point, the equation used becomes:

$$\text{Current } IOB = \frac{0.05 * \text{Initial Bolus Amount} * (\text{Elapsed Time Since Tail Time Started})}{\text{Total Tail Time}}$$

More generally, the tail can be affected by changing the percentage of insulin on board at which the tail time occurs. In such an instance, the above equation becomes:

$$\text{Current } IOB = \frac{\text{Tail Threshold \%} * \text{Initial Bolus Amount} * (\text{Elapsed Time Since Tail Time Started})}{\text{Total Tail Time}}$$

Figure 14D:
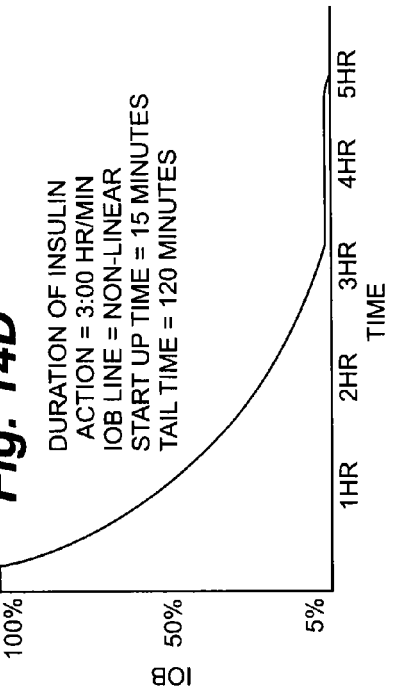
Figure 14C:
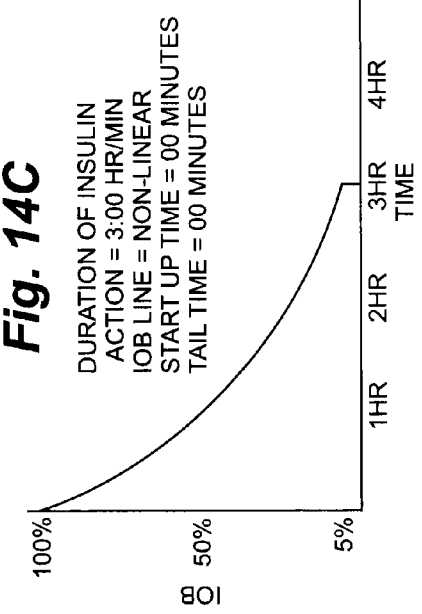

FIG. 14C shows a non-linear absorption model in which the programmed duration in the duration-of-activity field 398 was set to be 3 hours. The start time and tail time are either not selected or set to be zero. A variety of equations can be used to model the non-linear absorption model, such as an exponentially decreasing, hyperbolic, or other equation. The following is an example of one possible equation used to model non-linear insulin absorption:

$$y = e^{-\left(\frac{x^2 \ln(20)}{T^2}\right)}$$

Where
y=Current IOB
x=Elapse time
T=Duration of Activity

The method of calculating the current insulin on board remains the same, by determining the amount of insulin on board based on the model by using the time elapsed since the insulin is delivered into the user's body.

FIG. 14D shows a non-linear absorption model having a non-zero start time and tail time. In the embodiment shown, the start time is programmed to be 15 minutes and the tail time is programmed to be 2 hours. The start time and tail time are implemented similarly to those described in conjunction with FIG. 14B, while using the non-linear model described in conjunction with FIG. 14C.

Additional methods for varying the absorption model can be incorporated into the pump 100 as well. A general method for varying insulin absorption would include incorporation of factors which can affect the rate at which the user would actually absorb insulin, such as due to boluses, activity, or other factors. In one example embodiment, the pump 100 varies the insulin absorption model based on a bolus amount. In a further embodiment, the pump 100 varies the insulin absorption model based on both a bolus amount and the user's body weight. In a further embodiment, the pump 100 varies the insulin absorption model based on the user's anticipated near-future activity level. Other factors can include the user's age, fitness level, body mass index or other user entered health information. In yet a further embodiment, the pump varies the insulin absorption model based on the ambient temperature experienced by the user. In further embodiments, the pump 100 varies the insulin absorption model based on other patient-specific parameters.

Figure 15:
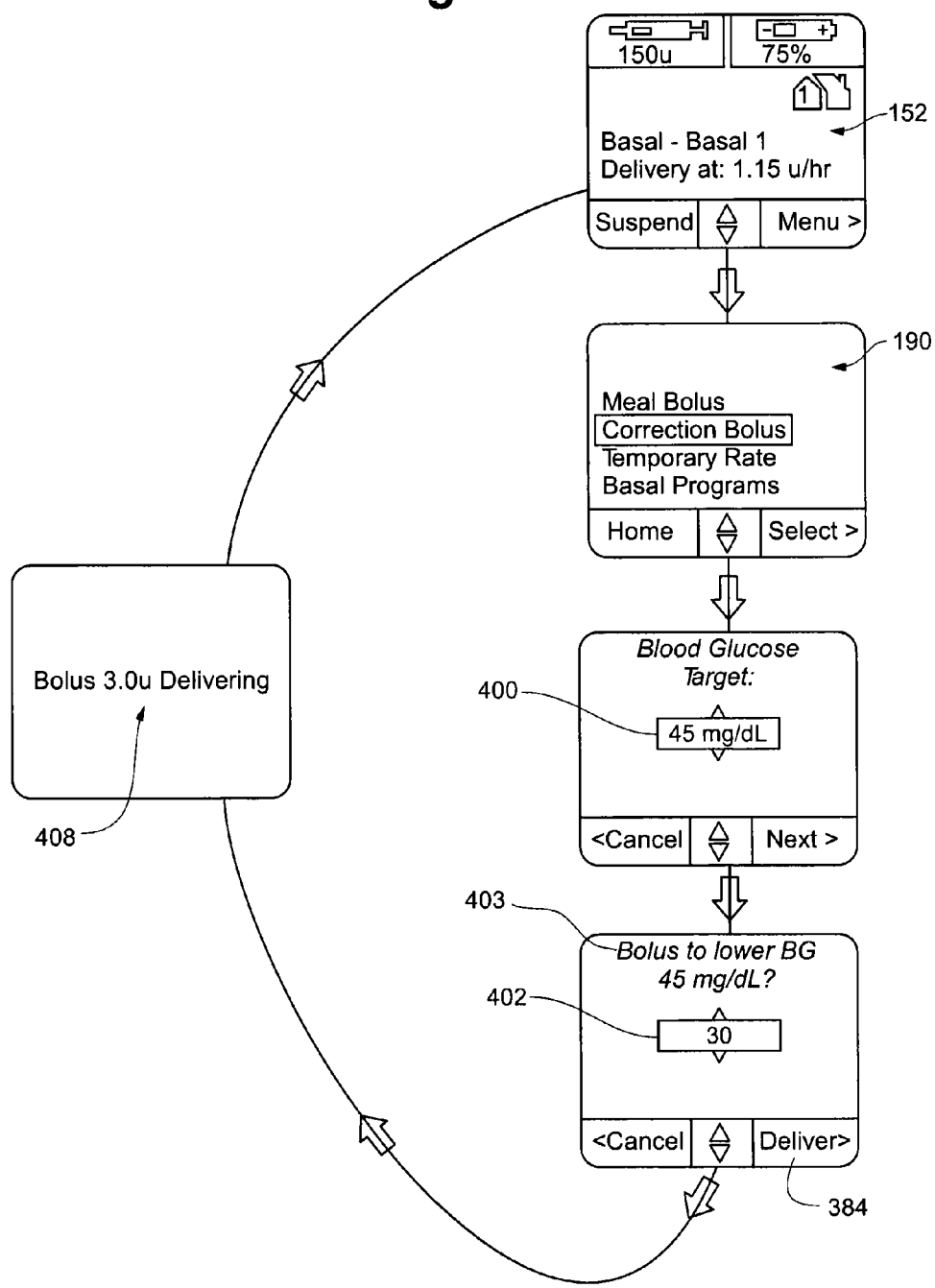
FIG. 15 illustrates setting the operational parameters for the correction bolus delivery programs executed by the pump shown in FIGS. 1 and 2.

Referring now to FIG. 15, the user delivers a correction bolus by selecting the correction bolus menu item from the main menu 190. The pump 100 then displays an amount field 400 in which the user enters the amount by which they would like to lower their blood glucose. The user scrolls to and selects the desired amount. The pump 100 then calculates a recommended bolus and indexes focus to a recommend-bolus field 402. The pump 100 also displays a banner 403 with the recommend-bolus field 402 which reads "Bolus to Lower BG X?" where X is the amount that the user entered to lower his or her blood glucose. The pump 100 calculates the recommended bolus according to the equation:

$$\text{Correction Bolus} = \frac{\text{Drop in Glucose Level}}{\text{Correction Factor}} \quad (1)$$

and displays the recommended correction bolus in the recommend-bolus field 402. The user can adjust the recommended correction bolus by incrementing the recommend amount up or down using the up and down keys 142 and 144, respectively.

When the desired correction bolus is displayed in the recommend-bolus field 402, the user activates the Deliver function 384 and the pump 100 displays a banner 408 in the screen stating the bolus is delivering and the amount of the bolus. The pump 100 then returns to the home page 152 after delivery of the bolus is complete.

Additionally, the pump 100 has a duration of activity program that determines whether any bolus that was previously delivered is still active. If a previous bolus is still active, the pump 100 calculates the estimated amount of insulin that is still active in the patient's body. In a linear system the pump uses an equation analogous to the Insulin on Board equations above:

$$\text{Residual Insulin} = \frac{\text{Last Bolus Amount} \times (\text{Duration} - \text{Time Since Last Bolus})}{\text{Duration}} \quad (2)$$

if (Duration–Time Since Last Bolus)≤0,
otherwise Residual Insulin=0.

where Residual Insulin is the amount of insulin from a previous bolus still active within the user's body, Last Bolus Amount is the amount of the last bolus, Duration is the duration of insulin, which is set as described in conjunction with FIG. 13, and Time Since Last Bolus is the amount of time lapsed since the last bolus was delivered. Additionally, there could be more than one boluses still active within the user's body. In this situation, equation 2 is used to calculate the residual insulin from each of the still active boluses and the amount of residual insulin for each of the previous boluses is summed to determine Residual Insulin. Alternately, a modified version of equation 2 may be used based on a non-linear insulin absorption model, if selected.

The pump 100 then calculates an adjusted correction bolus according to the equation:

Reduced Correction Bolus=Correction Bolus−Residual Insulin (3)

The pump 100 then displays the reduced recommended corrected bolus in the correction-bolus field 402 rather than the recommended correction bolus. The display also presents a banner (not shown) with the recommended-bolus field that indicates that the recommended bolus is reduced to accommodate residual bolus insulin that is still working in the user's body. An example of such a banner is "*reduced for insulin on-board".

In an alternative embodiment, when the user selects the Correction Bolus menu item from the main menu 190, the pump 100 indexes to a display that presents the correction factor, displays the user's target blood glucose level, and displays a current-blood-glucose field that prompts the user to enter the user's current blood glucose level. The user scrolls to and selects their current blood glucose level. The pump 100 then calculates the appropriate amount of the bolus to lower the user's blood glucose level to the target value and then presents the verification display. In this embodiment, the pump 100 calculates the desired drop in the glucose level, and the pump 100 calculates the correction bolus according to the equation:

$$\text{Correction Bolus} = \frac{\text{Current Glucose Level} - \text{Target Glucose Level}}{\text{Correction Factor}} \quad (4)$$

In one possible embodiment, the pump 100 varies the correction bolus amount based not only upon the time of day, but also the current blood glucose of the user. The user can set one or more rules in the pump 100 to change the correction factor applied. These rules can be based on a rules framework programmed into the pump 100. For example, the pump can include an additive rule framework of the form "If blood glucose is above X, add Y %". The user could create a number of personalized rules of the same form, by entering a blood glucose setting and a percentage value. For example, by entering 250 and 20%, respectively, the user tells the pump 100 to add 20% to the bolus if the user's blood glucose level is over 250. In a possible embodiment, the effect of these defined rules can be added to the correction bolus after it is initially calculated using equation (4), above. In a second possible embodiment, the correction factor is altered to take into account whether or not a rule applies at the time the correction bolus is calculated.

A plurality of rules can be created in the pump 100 with differing glucose values and percentages. In one possible embodiment, up to four rules can be programmed into the pump 100. Additionally, the added insulin delivered by the pump 100 can be displayed on the pump screen, such as upon selection of the Correction Bolus menu item in the main menu 190. These equations can change based on the insulin absorption model selected.

J. Negative Meal Bolus

Similar to the correction bolus, the pump 100 can suggest a negative meal bolus, which is a suggested amount of carbohydrates for the user to consume. A negative meal bolus is suggested by the pump when the user's blood glucose level is too low or potentially will become too low due to the current level of insulin on board. The negative meal bolus is complementary to the correction bolus, and the two operate to maintain the user's blood glucose level within a safe range.

In a possible embodiment, when the user selects the Correction Bolus menu item from the main menu 190 and the pump 100 determines that the user's blood glucose is below the target level, the pump indexes to a display that includes a notification message indicating to a user that their blood glucose level is below their target blood glucose level. In a further embodiment, the pump 100 includes a negative meal bolus target analogous to the correction bolus target, which is a target level to which the negative meal bolus is configured to aim. The negative meal bolus target can be a different value from the correction bolus target. For example, the correction bolus target can represent a higher level within a range of safe blood glucose levels, such as 130 mg/dl, and the negative meal bolus target can represent a lower level within the range, such as 90 mg/dl. In a possible embodiment, the correction bolus target and negative meal bolus target are user-selectable.

In a possible embodiment, the pump 100 deactivates the negative bolus feature based on the occurrence of other events within the pump. For example, the negative bolus feature can be disabled during an extended bolus, or for a predetermined or customizable period of time after delivery of a meal bolus, as described below.

The negative meal bolus feature allows the pump 100 to optionally display the amount of carbohydrates necessary to bring the user's low blood glucose back to the target level, consistent with the equations described above. In an embodiment of the pump 100 incorporating a food database as described below, the pump optionally displays one or more foods appropriate for treating low blood glucose which contain at least the required number of carbohydrates. In such an embodiment, the pump also optionally displays a minimum serving size to be consumed to reach the required number of carbohydrates.

The pump 100 also optionally displays the user's current blood glucose level or the user's target blood glucose level. The pump 100 optionally executes a meal bolus program which, in one aspect, can calculate and display the number of carbohydrates to bring the user's blood glucose from its current level to the user's target level. The calculated number of carbohydrates is editable by the user, although the number entered by the user may be replaced by the number calculated by the pump 100 if the user-entered value is lower.

Once the number of carbohydrates is accepted, raised, or lowered by the user, one of three things may happen. If the user accepts the calculated bolus, the pump 100 applies a "zero" bolus. If the user lowers the number of carbohydrates, the pump 100 displays a message indicating that the user's blood glucose would still be below target. If the user raises the number of carbohydrates, a meal bolus program, such as those discussed below, calculates the amount of insulin necessary to counteract the extra carbohydrates. This insulin can be delivered to the user at the time the user selects the number of carbohydrates to consume, or can optionally delay the insulin bolus for an amount of time sufficient to ensure that the user's blood glucose level increases quickly back to a normal level. In a possible embodiment, the pump 100 delays 15 minutes before delivering additional insulin to allow the user a chance to consume some carbohydrates and raise their blood glucose level. In a further possible embodiment, the software prompts the user to perform a blood glucose test to confirm that the bolus is needed. In such an embodiment, the software allows the user to confirm or cancel the bolus as appropriate.

In an embodiment of the pump 100 including a food database, as described below, the pump 100 can display one or more foods that are good to eat when blood glucose is abnormal, i.e. too high or too low. Additionally, foods which are well-suited for consumption in anticipation of exercise or on sick days can be displayed as well. The pump 100 can present to a user a list of foods which are appropriate under other circumstances as well.

K. Meal Bolus Programs

A meal bolus is a bolus that the pump delivers in anticipation of a meal that the user plans to consume. In one possible embodiment, the amount of the meal bolus is based on how much insulin is required to work against the carbohydrates that the user plans to consume. There are several types of meal bolus programs that the pump 100 may include. One type is a standard bolus in which the pump 100 delivers the meal bolus a predetermined time prior to when the user consumes the meal or snack. The standard program delivers the bolus at the maximum rate that the pump 100 is able to deliver it. As explained below, the standard program can be set for programming in either units of insulin or number of carbohydrates. Another type of meal bolus that the pump 100 can be programmed to deliver is an extended bolus in which the pump 100 delivers the meal bolus over an extended period. Yet another type of meal bolus that the pump 100 can be programmed to deliver is a combination bolus in which the pump 100 immediately delivers a portion of the meal bolus and the balance of the meal bolus over an extended period of time.

Figure 16:
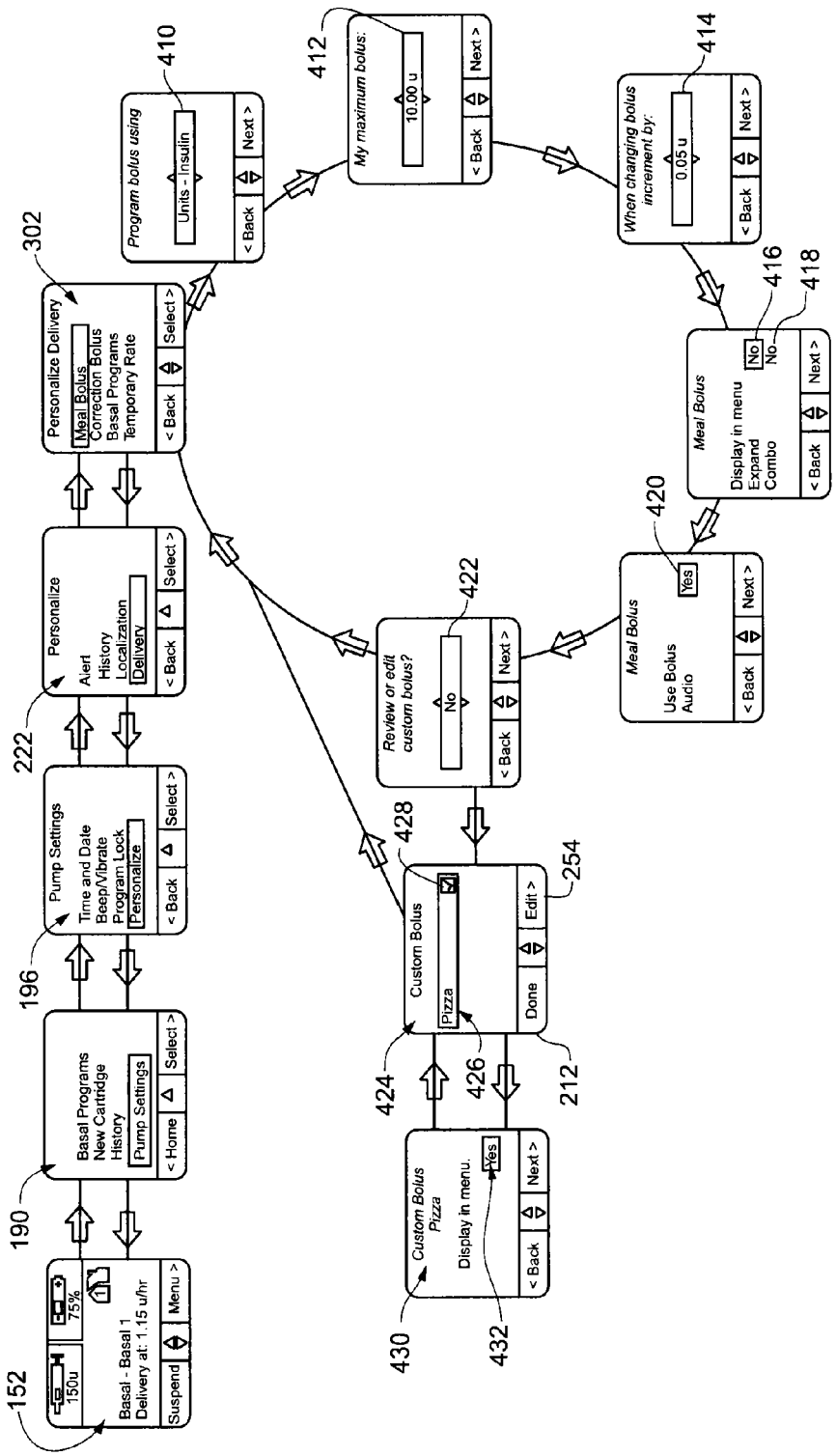
FIGS. 16-24 illustrate setting the operational parameters for the meal bolus delivery programs executed by the pump shown in FIGS. 1 and 2.

Referring to FIG. 16, to instruct the pump 100 to program the standard meal bolus in units of insulin and to otherwise personalize the meal bolus program, the user accesses the Personalize Delivery submenu 302. From the Personalize Delivery submenu 302, the user selects the Meal Bolus menu item and the pump 100 prompts 410 the user to select whether to program in units of insulin or carbohydrates. The user selects units of insulin. The pump 100 then prompts 412 the user to select the maximum bolus that can be delivered. In one possible embodiment, the user scrolls through values in the range between 0 units and 40 units of insulin in increments of 1 until the desired value is highlighted. Next, the pump 100 prompts 414 the user to select the increments in which the user can select the actual bolus to be delivered. In one possible embodiment, the user scrolls between 0.05 units, 0.10 units, 0.50 units, and 1.00 units.

Figure 18:
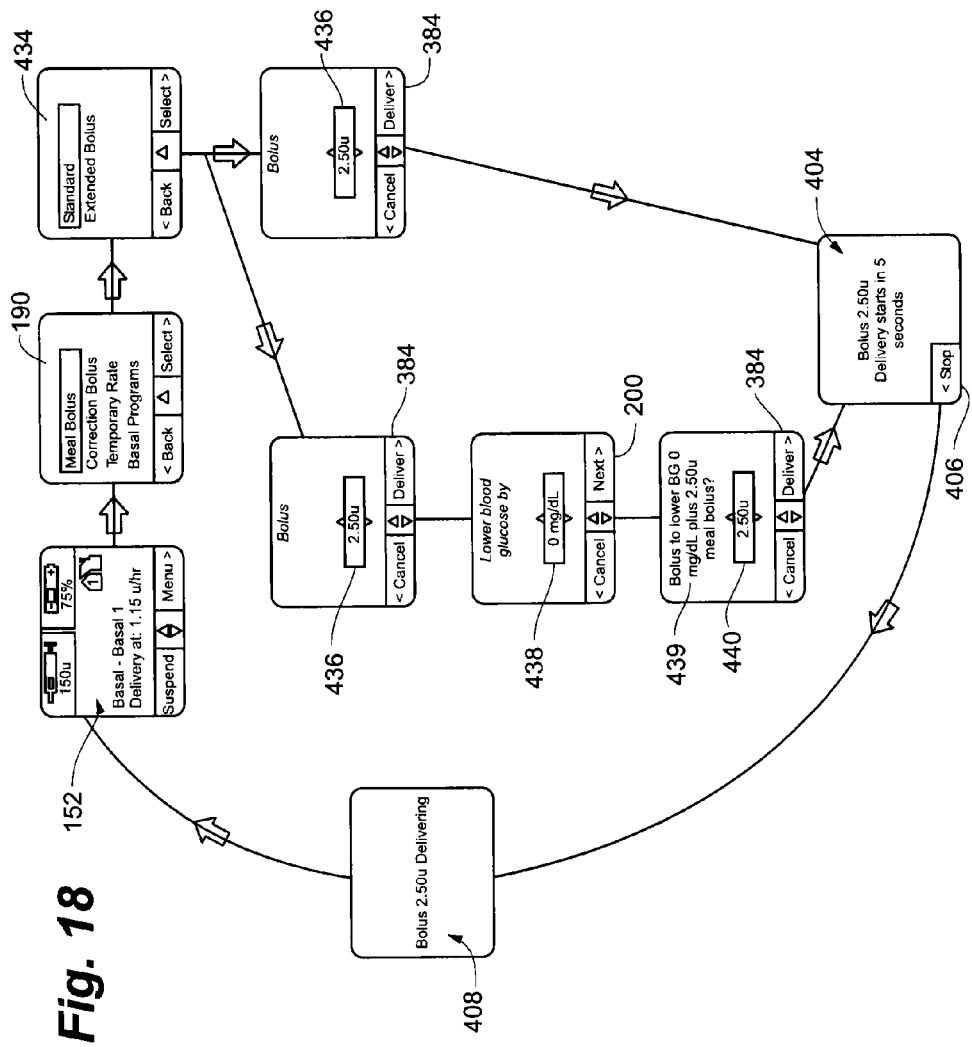

The pump 100 then prompts 416 the user to select whether to enable an extended bolus program and to display an Extended Bolus menu item within a Meal Bolus submenu 434 (FIG. 18). The extended bolus program is selected by selecting a yes value and disabled by selecting a no value. The pump 100 also prompts 418 the user to select whether to enable a combination bolus program and to display a Combo Bolus menu item within the Meal Bolus submenu 434. The combination bolus program is activated by selecting a yes value and is disabled by selecting a no value. The pump 100 then prompts 420 the user to choose whether to enable an audio bolus program. The user selects a yes value to enable the audio bolus program and selects a no value to disable the audio bolus program.

If the pump 100 is preprogrammed with one or more custom meal boluses, the pump prompts 422 the user to select whether to review or edit a custom bolus. If the user does not want to review or edit a custom bolus, the user selects no and the pump 100 returns to the Personalize Delivery submenu 302. If the user selects yes, the pump 100 presents a display 424 entitled "Custom Bolus," which lists the names 426 of the available custom meal bolus programs. The display 424 also presents a check box 428 for each of the custom meal bolus programs 426. If a custom meal bolus program 426 is enabled, the check box 428 is set. If a custom meal bolus program 426 is not enabled, the check box 428 is cleared. When a custom meal bolus is enabled, it is displayed in the Meal Bolus submenu 434 as a separate menu item. If the custom meal bolus program is not enabled, it is not displayed in the Meal Bolus submenu 434 and the user cannot execute the program.

To enable or disable a meal bolus program, the user scrolls to the desired custom meal bolus program and activates the Edit function 254. The pump 100 presents a display 430 entitled "Custom Bolus: X," where X is the name of the selected custom meal bolus program. In the illustrated example, the title of the display is Custom Meal Bolus: Pizza". Upon activating the Edit function 254, the pump 100 prompts 432 the user to select either a yes value or no value. If the user selects the yes value, the pump 100 enables the custom meal bolus program 426 and displays the name of the program as a menu item in the Meal Bolus submenu 434. If the user selects the no value, the pump 100 disables the custom meal bolus program 426 and does not display the name of the program as menu item in the Meal Bolus submenu 434. After the yes or no value is selected, the pump 100 returns to the "Custom Bolus" display 424.

The user repeats this procedure from the "Custom Bolus" display 424 for each custom meal bolus program 426 for which they desire to change the enabled state. When the user is done changing the enabled states for the available custom meal bolus programs 426, the user activates the Done function 212 in the "Custom Bolus" display 424. The pump 100 then returns to the Personalize Delivery submenu 302.

Additionally, in one possible embodiment, if there are no custom meal bolus programs available for the user to enable, the pump 100 automatically returns to the Personalize Delivery submenu 302 after the user instructs 420 the pump 100 whether to enable an Audio Bolus.

In one possible embodiment, a user can program the pump 100 to include a database of foods for which to configure delivery of a custom bolus. A user of the pump 100 selects one or more foods from the database of foods to form a meal from which the user's carbohydrate intake is calculated. The database of foods can include a number of records associated with food entries. The food entries each represent a food or a combination of foods. The record includes fields for a name of the food entry, the amount of carbohydrates contained in the food or foods represented by the food entry, and a default serving size for the food entry.

Each entry in the food database is a food entry. The food entry has a number of fields within it. One field can be a name field, and will be the information displayed to the user representing the name or names of the food displayed. The food entries can represent specific foods tracked by a user of the pump. The food entries can also represent meals including a variety of foods typically eaten by the user, and would include combinations of types of foods. Examples of foods displayed could be "pizza" or "apple", or could also be "Chicken, Potato, and Green Beans" or some other combination commonly consumed by the user, who may wish to store the combination so that they do not have to select each food and serving size each time they consume the common meal.

Additional fields include a carbohydrate field and a serving size field related to the foods displayed. The carbohydrate field contains information related to the number of carbohydrates are contained in the foods, given a default serving size stored in the serving size field. The carbohydrate field and the serving size field are customizable by a user, and can be set independently of each other as well.

In a possible embodiment of the food database, nutritional information is stored in the food database and associated with the one or more food items. The additional nutritional information can be stored in additional fields associated with the food entry, or can be stored separately and referenced by the food entry. The nutritional information includes, for example, additional carbohydrate information, fat information, or protein information. Other nutritional information can be stored as well.

In a further possible embodiment of the food database, the pump 100 stores metadata related to one or more user conditions in conjunction with one or more of the foods in the food database. The pump can be configured to display specific foods upon occurrence of the conditions. These conditions include, for example, such as activity levels, sickness, high or low blood glucose levels; or other conditions. For example, in the case of a low blood glucose level, a metadata tag may be associated with a food entry in the food database "orange juice" which will be displayed to the user upon detection of a low blood glucose level. Optionally, the pump 100 displays a specific amount of orange juice to consume, as calculated using the negative meal bolus feature, described herein.

In one embodiment, the food database includes 500 or more foods, categories of foods, and/or meals. In a possible embodiment, the food database is a subset of a larger food database that is stored on a computing system that can be interfaced with the pump 100, such as the system shown below in FIG. 26.

Figure 17:
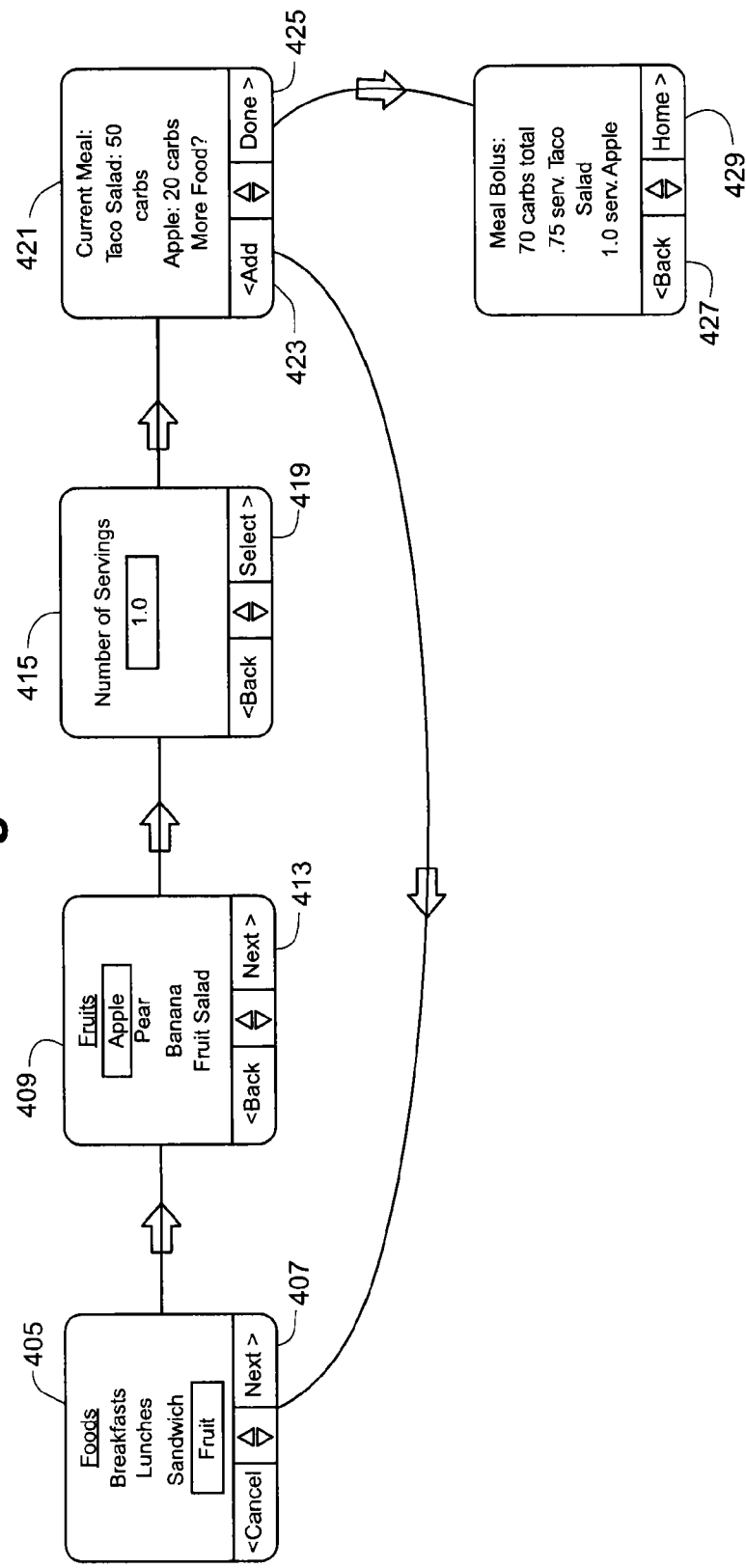

Referring now to FIG. 17, a meal maker function allows the user to select one or more food entries from the food database to form meals. Meals refer to combinations of one or more food entries selected using the pump which indicate the food or foods which the user plans to consume. In one embodiment, up to 10 food entries are selectable from the food database to form a meal. The food entries in the food database are categorized into one or more hierarchical levels for ease of navigation, and food categories screen 405 displays one or more food categories in a category listing 407, allowing the user to navigate to a food or meal to be consumed using the up and down keys 142, 144. The user selects a food or meal category from the overall food listing 407, and confirms the choice using a next option 409. Upon activation of the next option, the pump 100 indexes focus to a food entries screen 411. The food entries screen 411 presents a number of foods within the category selected using the food categories screen 405. In the example shown, a fruits category includes single fruits as well as a fruit salad option, which corresponds to a variety of fruits. The user selects at least one food using the up and down keys 142, 144 and uses a next option 413 to confirm selection of one of the food entries.

Upon activation of the next option 413, the pump 100 indexes focus to a servings screen 409. The user selects the number of servings, or "serving size" of the selected food entry that will be consumed, using a servings field 417 and the up and down keys 142, 144. The user optionally also defines the default amount of food referred to as the "serving size", such that a single serving of the food represents the amount of the food that user eats in a single meal. In one particular implementation, the selectable number of servings of the food can be between 0.5 and 3 servings, based on the default food amount. Upon selection of a serving size using a select option 419, the pump calculates the number of carbohydrates to be consumed for the selected food entry, and indexes focus to a confirmation screen 421. The confirmation screen 421 displays the food or foods selected, as well as a number of informational items related to nutritional aspects of the food, including the serving size of the food, the number of carbohydrates, and the amount of fiber, protein, and fat included in the food. The informational items correspond to the information stored in the food database and associated with the food entry. Other information can be displayed as well, such as by incorporating additional fields into each food entry in the food database. The user can select an add option 423 to add additional food entries to the current meal using the food database, or confirm that the food entries selected represent the meal desired using a set option 425. Upon user confirmation using the set option 425, the pump 100 indexes focus to a delivery screen 427. The delivery screen 427 displays overall meal information, including a total number of carbohydrates consumed, a listing of the foods to be consumed, and other optional nutritional or serving size information. Upon selection of a home option 429 the pump indexes focus to a carbohydrate delivery screen 200, such as are shown below in FIG. 20. Using the appropriate screens as described below, the pump delivers an appropriate meal bolus based on the total number of carbohydrates to be consumed in the meal. A back option returns to the confirmation screen 421 allowing the user to add additional foods to the meal.

Figure 20:
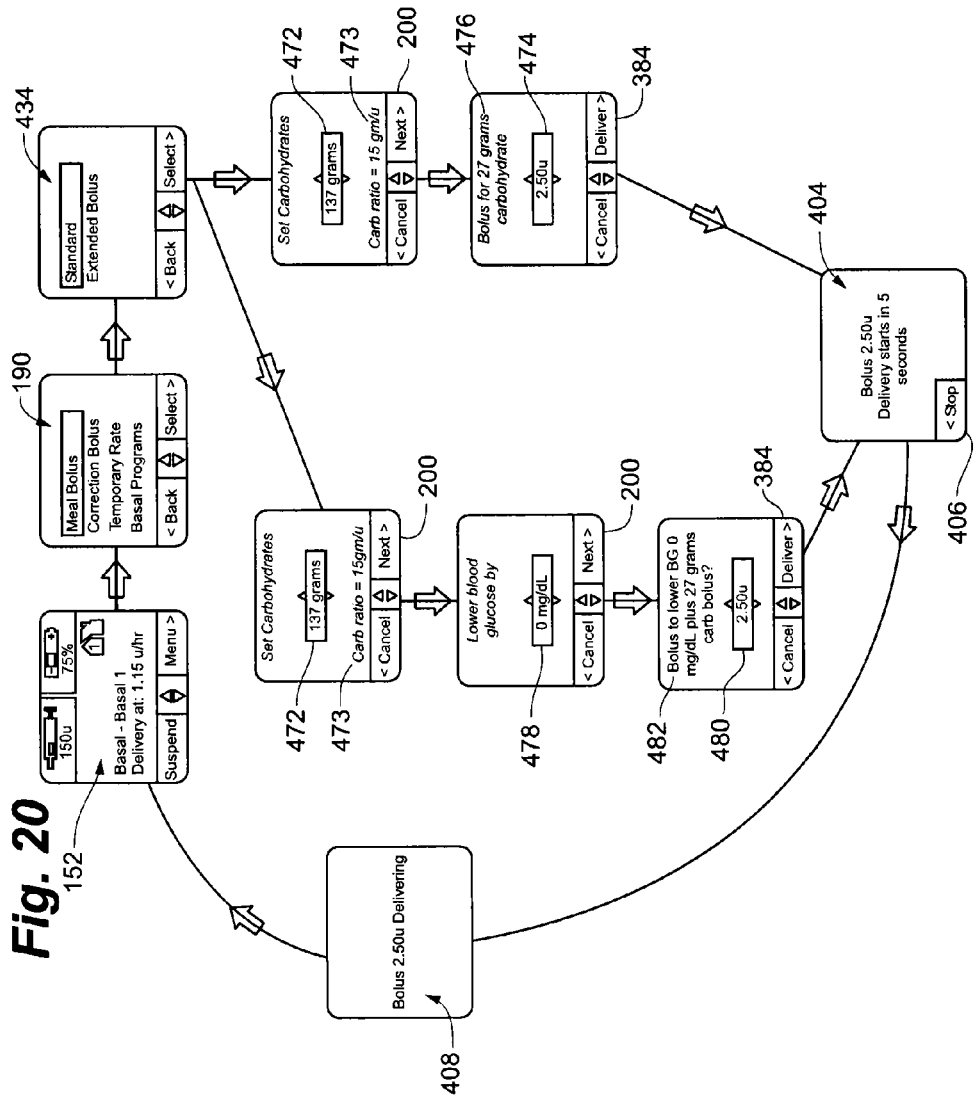

If a food is not selected from the food database, the user can directly enter a number of carbohydrates, as illustrated in FIG. 20 below. However, in any event the pump prevents the user from specifying a serving size for the food item which would cause the total insulin bolus to be greater than the programmed maximum insulin dose, as set using the prompt 412.

In the embodiment shown in FIG. 17, the meal maker function provides a hierarchy of menu-based screens configured to organize the foods listed in the food database. The hierarchy of menus includes one or more levels of menus, each menu representing foods, meals, types of foods, types of meals, or other user-selectable navigation or selection criteria. In another embodiment, all foods are displayed in a non-hierarchical listing.

FIG. 18 illustrates administration of a standard meal bolus when the pump 100 is set to program meal boluses using units of insulin. The user selects the meal bolus menu item from the main menu, and the pump indexes to a Meal Bolus submenu 434. The meal bolus submenu 434 lists the available meal bolus programs. Examples include the standard meal bolus program, the extended meal bolus program, the combination meal bolus program, and any enabled custom meal bolus programs. In the illustrated example, only the extended meal bolus program is enabled and the Meal Bolus submenu 434 includes a Standard Bolus and an Extended Bolus. The user highlights the Standard Menu item and the pump 100 prompts 436 the user to enter the number of units to deliver. In one possible embodiment, the user can scroll through values in the range from 0 units to 17 units in increments of 0.5 units.

If the pump 100 is programmed to enable administration of a correction bolus through the Meal Bolus program, the pump 100 prompts 436 the user to enter the number of units to deliver as a meal bolus. The user then activates the Deliver function 384 and the pump 100 prompts 438 the user to enter the amount by which they want to lower their blood glucose level. In one possible embodiment, the user enters the amount by scrolling through values in units of either mg/dL or mmol/L. When the desired drop in blood glucose is entered, the user activates the Next function 200, which causes the pump 100 to calculate a recommended bolus amount and to display a user interface with the banner 439 stating "Bolus to Lower BG X plus Y meal bolus." X is the amount the user entered to lower the blood glucose level, and Y is the amount of the meal bolus entered by the user.

The user interface also displays the recommended bolus amount 440 to deliver. The recommended bolus amount 440 is the recommended correction bolus as calculated above, plus the amount of the meal bolus. This feature allows the user to correct a high blood glucose level and deliver additional insulin to work against carbohydrates that they plan to consume. The user can adjust the recommended bolus amount by increasing or decreasing the recommended bolus amount by scrolling up or down. In one possible embodiment, the user scrolls in increments of 0.5 units. Once the desired bolus amount is set, the user activates the Deliver function 384.

Activating the Deliver function 384 causes the pump 100 to deliver the correction bolus. The pump 100 will begin to deliver the bolus and display a banner 408 stating that the bolus is being delivered. An example of such a banner is "Bolus X is Delivering", where X is the bolus amount. When delivery of the bolus is complete, the pump 100 returns to the home page 152.

In an alternative embodiment, when the pump 100 is programmed to enable administration of a correction bolus through a Meal Bolus, the pump 100 displays a user interface entitled Current Blood Glucose." The pump 100 calculates the current correction factor and displays the correction factor in the user interface. The pump 100 also displays the target blood glucose level. The user then enters his or her current blood glucose level in units of either mg/dL or mmol/L, by scrolling through a range of values until the current blood glucose level is displayed. In this embodiment, the target blood glucose level and the appropriate units are programmed into the pump 100 when personalizing the correction bolus program as described herein. After the user enters the current blood glucose level, the user activates the Next function 200 and the pump 100 calculates a recommended bolus amount, using the equations set forth above, and adds it to the meal bolus. The pump 100 displays the user interface with the banner "Bolus to Lower BG X plus Y Meal Bolus" 439. The user can then change the amount 440 and activate the Deliver function 384 to begin delivery of the bolus as described above.

Additionally, in one possible embodiment, the pump 100 adjusts the recommended bolus based on the meal bolus or the meal bolus plus the correction bolus to accommodate insulin on board or residual insulin that is still working within the user's body. In this embodiment, the amount of the adjusted correction bolus is adjusted using the equations described above in conjunction with the duration-of-activity function. The methods of adjusting the bolus amount for insulin on board are described above.

Figure 19:
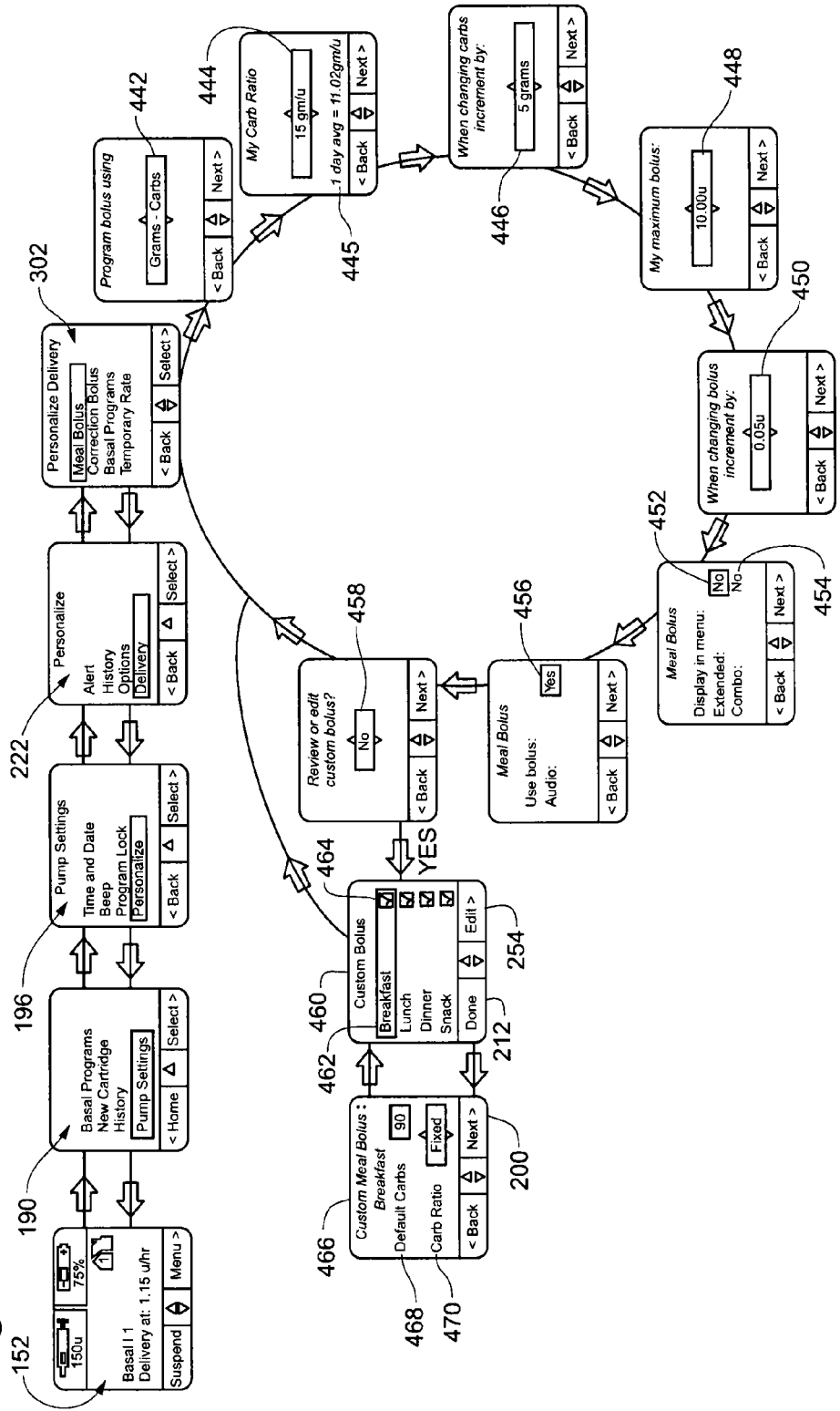

Referring to FIG. 19, to instruct the pump 100 to program the standard meal bolus in number of carbohydrates consumed and to otherwise personalize the meal bolus program, the user accesses the Personalize Delivery submenu 302. From the Personalize Delivery submenu 302, the user selects the Meal Bolus menu item and the pump 100 then prompts 442 the user to select whether to program in units of insulin or carbohydrates. The user highlights units of carbohydrates and activates the Next function 200. The pump 100 prompts 444 the user to enter one or more carbohydrate ratios, which is the number of grams of carbohydrates that each unit of insulin will counteract. The pump 100 optionally accepts a schedule of carbohydrate ratios as well, allowing the carbohydrate ratio to change based on the time of day. The pump 100 also calculates the historical average carbohydrate ratio 445 for a predetermined time-period and displays that historical average with the prompt 444. In one possible embodiment, the historical average is for the previous 7-day period. As discussed above, other embodiments average the carbohydrate ratio over other periods of time. In yet other embodiments the user can select the period of time over which to average the carbohydrate ratio.

The user enters the carbohydrate ratio by scrolling through values in a predetermined range such as from 0 gm/u to 50 gm/u in increments of 1. When the desired number of carbohydrates is set, the user activates the Next function 200 and the pump 100 prompts 446 the user to set the increment by which the user would like to be able to scroll through the number of carbohydrates when programming the pump 100 to deliver a meal bolus. In one possible embodiment, the user can set the desired increment between 1 and 15 grams.

The pump 100 prompts 448 the user to enter the maximum bolus that can be delivered. In one possible embodiment, the user scrolls through values in the range between 0 units and 40 units of insulin in increments of 1 until the desired value is highlighted. The pump 100 then prompts 450 the user to enter the increments in which the user can select the actual bolus to be delivered. In one possible embodiment, the user scrolls between 0.05 units, 0.10 units, 0.50 units, and 1.00 units and activates the Next function 200.

The pump prompts 452 the user to select whether to enable an extended bolus program and to display an Extended Bolus menu item within the Meal Bolus submenu 434. The extended bolus program is enabled by highlighting and activating a yes value and not enabled by highlighting and selecting a no value. The pump 100 also prompts 454 the user to select whether to enable a combination bolus program and to display a Combo Bolus menu item within a Meal Bolus submenu 434. The combination bolus program is enabled by highlighting and activating a yes value and not enabled by highlighting and selecting a no value. The user activates the Next function 200 to index through these prompts 452 and 454. The pump 100 then prompts 456 the user to choose whether to enable an audio bolus program. The user selects a yes value to enable the audio bolus program and selects a no value to not enable the audio bolus program and then activates the next function 200.

If the pump 100 is preprogrammed with one or more custom meal boluses, the pump 100 then prompts 458 the user to select whether to review or edit a custom bolus. If the user does not want to review or edit a custom bolus, the user selects no and the pump 100 returns to the Personalize Delivery submenu 302. If the user selects yes, the pump indexes to a display 460 entitled "Custom Bolus," which lists the names 462 of the available custom programs. In the illustrated example, there are four custom boluses available on the pump, Breakfast, Lunch, Dinner, and Snack.

The screen also presents a check box 464 for each of the custom meal bolus programs 462. If a custom meal bolus program is enabled, the pump 100 sets the check box 464. If a custom meal bolus program is not enabled, the pump 100 clears the check box 464. When a custom meal bolus program is enabled, it is displayed in the Meal Bolus submenu 434 as a separate menu item. If the custom meal bolus program is not enabled, it is not displayed in the Meal Bolus submenu 434 and the user cannot execute the custom meal bolus program.

To enable or disable a custom meal bolus program, the user selects the desired custom meal bolus program and activates the Edit function 254. The pump 100 indexes to a display 466 entitled "Custom Bolus: X," where X is the name 462 of the selected custom meal bolus program. In the illustrated example, the title of the display 466 is Custom Meal Bolus: Breakfast". The user interface 466 displays 468 a default number of carbohydrates for the custom bolus. For example, the user can create a custom breakfast meal bolus that would have a default value of 90 carbohydrates, equal to the number of carbohydrates in a bowl of cereal and milk normally consumed by the user at breakfast. The pump also prompts 470 the user to select either a fixed carbohydrate ratio or the previously entered carbohydrate ratio schedule. If the user selects a fixed carbohydrate ratio, the fixed carbohydrate ratio is used with the custom meal bolus program. The value of the carbohydrate ratio 468 may or may not be the same value as the carbohydrate ratio 444. The user enters the carbohydrate ratio by scrolling through values in a predetermined range such as from 0 gm/u to 50 gm/u in increments of 1. When the desired number of carbohydrate ratio is set, the user activates the Next function 200 and the pump 100 returns to the "Custom Bolus" submenu 434.

The user repeats this procedure from the "Custom Bolus" display 460 for each custom bolus program for which they desire to change the enabled state. When the user is done changing the enabled states for the available custom meal bolus programs, the user activates the Done function 212. The pump 100 then returns to the Personalize Delivery submenu 302.

Additionally, in one possible embodiment, if there are no custom meal bolus programs available for the user to enable, the pump 100 automatically returns to the Personalize Delivery submenu 302 after the user instructs 456 the pump 100 whether to enable an Audio Bolus.

FIG. 20 illustrates administration of a standard meal bolus when the pump 100 is set to program meal boluses using grams of carbohydrates. The user selects the meal bolus menu item from the main menu 190, and the pump indexes to the Meal Bolus submenu 434. The meal bolus submenu 434 lists the available meal bolus programs. Examples include the standard meal bolus program, the extended meal bolus program, the combination meal bolus program, and any enabled custom meal bolus programs. In the illustrated example, only the extended meal bolus program is enabled and the meal bolus submenu includes a Standard Bolus and an Extended Bolus.

The user selects the Standard Menu item and the pump 100 prompts 472 the user to enter the number of carbohydrates that the user plans to consume. The user interface also displays the current carbohydrate ratio 473. The user sets the desired number of carbohydrates. In one possible embodiment, the user scrolls through carbohydrates in the range from 0 grams to 225 grams.

The user then activates the Next function 200 and the pump 100 calculates a recommended size for the meal bolus using the equation:

$$\text{Recommended Meal Bolus} = \frac{\text{Grams of Carbohydrates}}{\text{Carbohydrate Ratio}} \qquad (5)$$

The pump 100 displays 474 the recommended meal bolus. The user can then adjust the size of the meal bolus by scrolling up or down. In one possible embodiment, the pump 100 scrolls in increments of 1. Once the desired bolus amount is set the user activates the Deliver function 384.

In a further possible embodiment, the recommended meal bolus is altered based on other nutritional information associated with the selected food entries from the food database. For example, the meal bolus can be increased for foods with a large number of proteins and/or fats in addition to the carbohydrates in the food.

In yet another embodiment, the meal bolus is altered based on other nutritional information associated with the selected food entries from the food database. For example, a combination or extended bolus is optionally recommended for foods having a large number of fats in addition to the carbohydrates in the food.

When the pump 100 is programmed to enable administration of a correction bolus through a Meal Bolus, the pump 100 prompts 472 the user to enter the number of carbohydrates to be consumed. The user then activates the Next function 200, and the pump 100 prompts 478 the user to enter the amount by which they want to lower their blood glucose level. The user then activates the Next function 200, which causes the pump 100 to calculate a recommended bolus amount and to display a user interface with a banner 482 stating "Bolus to Lower BG X plus Y grams of carbohydrates." X is the amount by which the user entered to lower the blood glucose level, and Y is the number of carbohydrates that the user entered.

The pump 100 also displays the recommended bolus amount 480 to deliver. The recommended bolus amount 480 is the recommended correction bolus plus the amount of the meal bolus. This feature allows the user to correct a high blood glucose level and deliver additional insulin to work against carbohydrates that they plan to consume. The user can adjust the recommended bolus amount by increasing or decreasing the recommended bolus amount by scrolling up or down. In one possible embodiment, the user scrolls in increments of 0.5 units. Once the desired bolus amount is set, the user activates the Deliver function 384.

Activating the Deliver function 384 causes the pump 100 to start the countdown timer and display the banner 404 that states a bolus will be delivered in predetermined time. In one possible embodiment, that time is 5 seconds and the banner 404 also states the bolus amount. An example of a possible banner 404 states "Bolus X Delivery Starts in 5 Seconds," where X is the bolus amount. The pump 100 also assigns a Stop function 406 to the first function key 138.

If the user activates the Stop function 406 before the countdown timer times out, the pump 100 will terminate delivery of the bolus and return to the home page 152. If the user does not activate the Stop function 406, when the timer times out, the pump 100 will begin to deliver the bolus and display the banner 408 stating that the bolus is being delivered. An example of such a banner is "Bolus X is Delivering", where X is the bolus amount. When delivery of the bolus is complete, the pump returns to the home page 152.

In an alternative embodiment, when the pump 100 is programmed to enable administration of a correction bolus through a Meal Bolus, the pump 100 prompts the user to enter their current blood glucose measurement. The pump 100 calculates the current correction factor and also displays the correction factor and the target blood glucose level with the prompt. The user then enters his or her current blood glucose level in units of either mg/dL or mmol/L, by scrolling through a range of values until the current blood glucose level is displayed. In this embodiment, the target blood glucose level and the appropriate units are programmed into the pump when personalizing or customizing the correction bolus program. Once the user enters the current blood glucose level, the user activates the Next function 200 and the pump 100 calculates a recommended bolus amount and adds it to the meal bolus. The pump 100 displays the user interface with the banner 482 "Bolus to Lower BG X plus Y grams of carbohydrates." The user can then change the amount and activate the Deliver function 384 to begin delivery of the bolus as described above.

Additionally, in one possible embodiment, the pump 100 adjusts the recommended bolus based on the meal bolus or the meal bolus plus the correction bolus to accommodate insulin on board or residual insulin that is still working within the user's body. In this embodiment, the amount of the adjusted correction bolus is adjusted using the equations described above in conjunction with the duration-of-activity function. The methods of adjusting the bolus amount for insulin on board is described herein.

In a further possible embodiment, the pump 100 logs the meals selected by the user and for which meal boluses are delivered. The pump optionally logs nutritional information related to the meals, such as information related to carbohydrates, fats, or proteins. Other nutritional information can be logged as well.

In yet another embodiment the pump 100 generates and presents reports to the user. The reports can include historical food intake, as well as cumulative nutritional information of the foods consumed.

Figure 21:
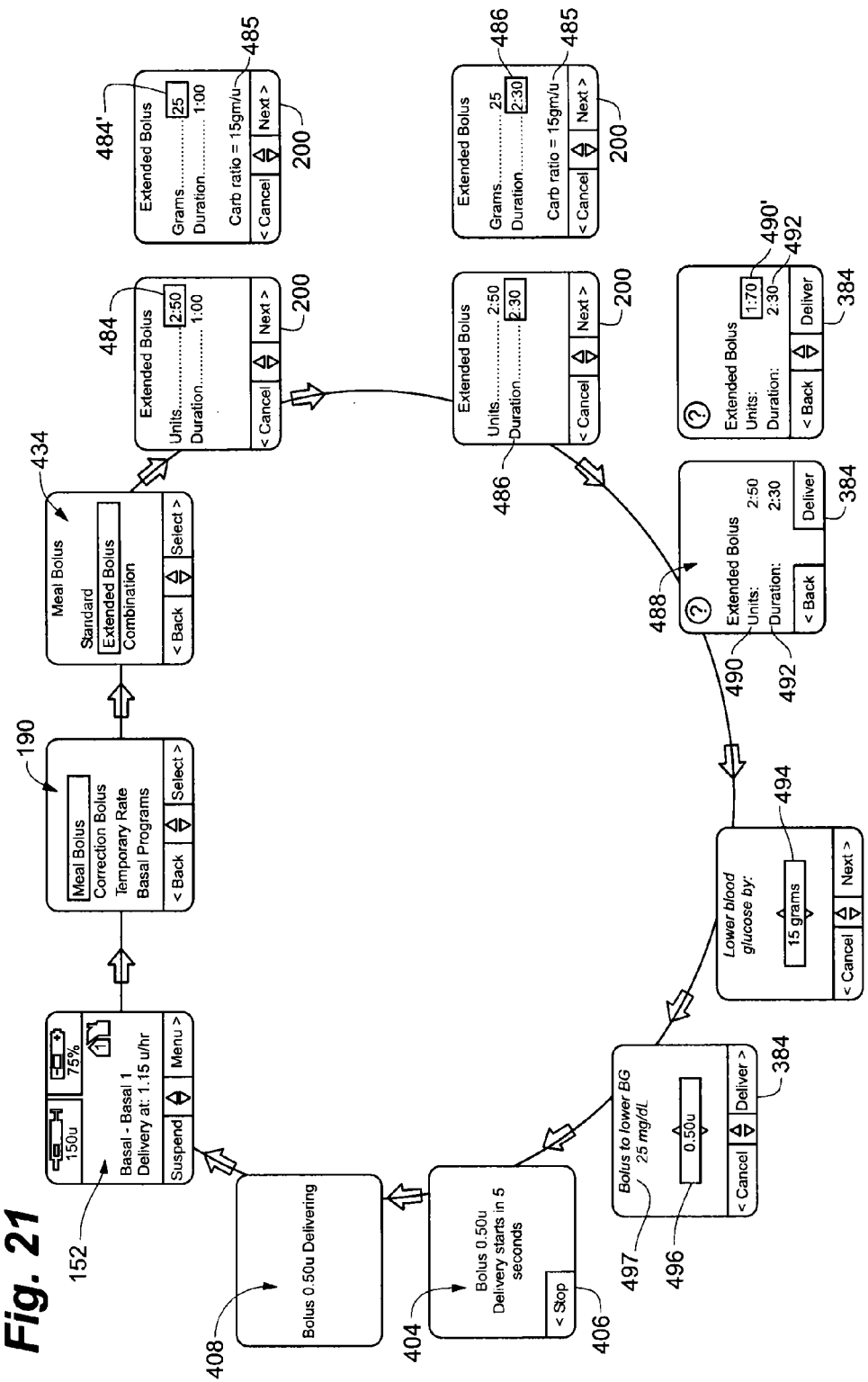

FIG. 21 illustrates administration of an extended bolus. The user selects the meal bolus menu item from the main menu 190, and the pump 100 indexes to a Meal Bolus submenu 434. The meal bolus submenu 434 lists the available meal bolus programs including the extended bolus program.

In the illustrated example, the extended meal bolus program and the combination bolus program are enabled and the meal bolus submenu includes menu items for a standard bolus, an extended bolus, and a combination bolus.

The user selects the Extended Bolus menu item and, when the pump 100 is set to program in units of insulin, the pump prompts 484 the user to enter the number of units to deliver. In one possible embodiment, the user can scroll through values in the range from 0 units to 17 units in increments of 0.5 units. When the number of units for delivery are entered, the user activates the Next function 200 and the pump 100 prompts 486 the user to enter the duration of length of time over which the extended bolus is to be delivered. In one possible embodiment, the user enters a duration in the range of 0 minutes to 6 hours in increments of 30 minutes.

When the duration is set, the pump 100 displays a user interface 488 that presents the programmed amount 490 of the extended bolus and the duration 492 over which it is to be delivered. To begin delivery of the extended bolus, the user activates the Deliver function 384. The pump 100 then begins delivering the extended bolus and will complete delivery upon expiration of the duration.

Alternatively, when the pump 100 is set to program in grams of carbohydrates, the pump 100 prompts 484' the user to enter the grams of carbohydrates that the user plans to consume rather than the units of insulin to deliver as an extended bolus. The pump 100 also prompts 486 the user to enter the duration for the extended bolus. The pump 100 displays 485 the carbohydrate ratio while prompting the user to enter the grams of carbohydrates 484' and the duration 486. The pump 100 then calculates a recommended bolus amount 490' using the carbohydrate ratio as described above and displays the recommended bolus amount 490', together with the duration 492 in a user interface that confirms the parameters for delivery of the extended bolus. The user can adjust the recommended amount 490' for the extended bolus by scrolling with the up and down keys 142 and 144. The user activates the Deliver function 384 to begin delivery of the extended bolus using the parameters displayed in the user interface.

After delivery of the extended bolus begins, if the pump 100 is programmed to enable administration of a correction bolus through the Meal Bolus program, the pump 100 prompts 494 the user to enter the amount by which they want to lower their blood glucose level. The user then activates the Next function 200 and the pump 100 prompts 496 the user to enter the number of units to deliver as a meal bolus. In one possible embodiment, the user enters the amount by scrolling through values in units of either mg/dL or mmol/L. When the desired drop in blood glucose is entered, the user activates the Next function 200, which causes the pump 100 to calculate a recommended bolus amount and to display the banner 497 "Bolus to Lower BG X." X is the amount by which the user entered to lower the blood glucose level.

The prompt 496 initially displays the recommended bolus amount to deliver. The recommended bolus amount is the recommended correction bolus 490 or 490', which the pump 100 calculates using the correction factor as discussed above. This feature allows the user to correct a high blood glucose level and deliver additional insulin to work against carbohydrates that they plan to consume. The user can adjust the recommended bolus amount 496 by increasing or decreasing the recommended bolus amount 496 by using the up and down keys 142 and 144. In one possible embodiment, the user scrolls in increments of 0.5 units. Once the desired bolus amount is set, the user activates the Deliver function 384.

Activating the Deliver function 384 causes the pump 100 to display the banner 404 that states a bolus will be delivered in predetermined time. In one possible embodiment, that time is 5 seconds and the pump 100 displays the bolus amount 496 in the banner. An example of a possible user interface states "Bolus X Delivery Starts in 5 Seconds," where X is the amount of the correction bolus. The pump 100 also assigns the Stop function 406 to the first function key 138.

If the user activates the Stop function 406 before the countdown timer times out, the pump 100 will terminate delivery of the correction bolus and return to the home page 152. In one possible embodiment, activating the Stop function 406 will terminate delivery of the correction bolus, but not the extended bolus. If the user does not activate the Stop function 406, when the timer times out, the pump 100 will begin to deliver the bolus and display the banner 408 stating that the bolus is being delivered. An example of such a banner is "Bolus X is Delivering", where X is the bolus amount. When delivery of the bolus is complete, the pump 100 returns to the home page 152. In an alternative embodiment, no timer is included in the pump and the pump 100 begins delivering the correction bolus immediately.

In an alternative embodiment, when the pump 100 is programmed to enable administration of a correction bolus through a Meal Bolus, the pump 100 prompts the user to enter their current blood glucose measurement. The pump 100 calculates the current correction factor and displays the correction factor in the user interface. The pump 100 also displays the target blood glucose level. The user then enters his or her current blood glucose level in units of either mg/dL or mmol/L, by scrolling through a range of values until the current blood glucose level is displayed. In this embodiment, the target blood glucose level and the appropriate units are programmed into the pump 100 when personalizing the correction bolus program. Once the user enters the current blood glucose level, the user activates the Next function 200 and the pump 100 calculates a recommended bolus amount and adds it to the meal bolus. The pump 100 displays the user interface with the banner "Bolus to Lower BG X plus Y Meal Bolus." The user can then change the amount and activate the Deliver function 384 to begin delivery of the bolus as described above.

Additionally, in one possible embodiment, the pump 100 adjusts the recommended correction bolus based on the meal bolus or the meal bolus plus the correction bolus to accommodate insulin on board or residual insulin that is still working within the user's body. In this embodiment, the amount of the adjusted correction bolus is adjusted using the equations described above in conjunction with the duration-of-activity function. The methods of adjusting the bolus amount for insulin on board is described herein.

Figure 22:
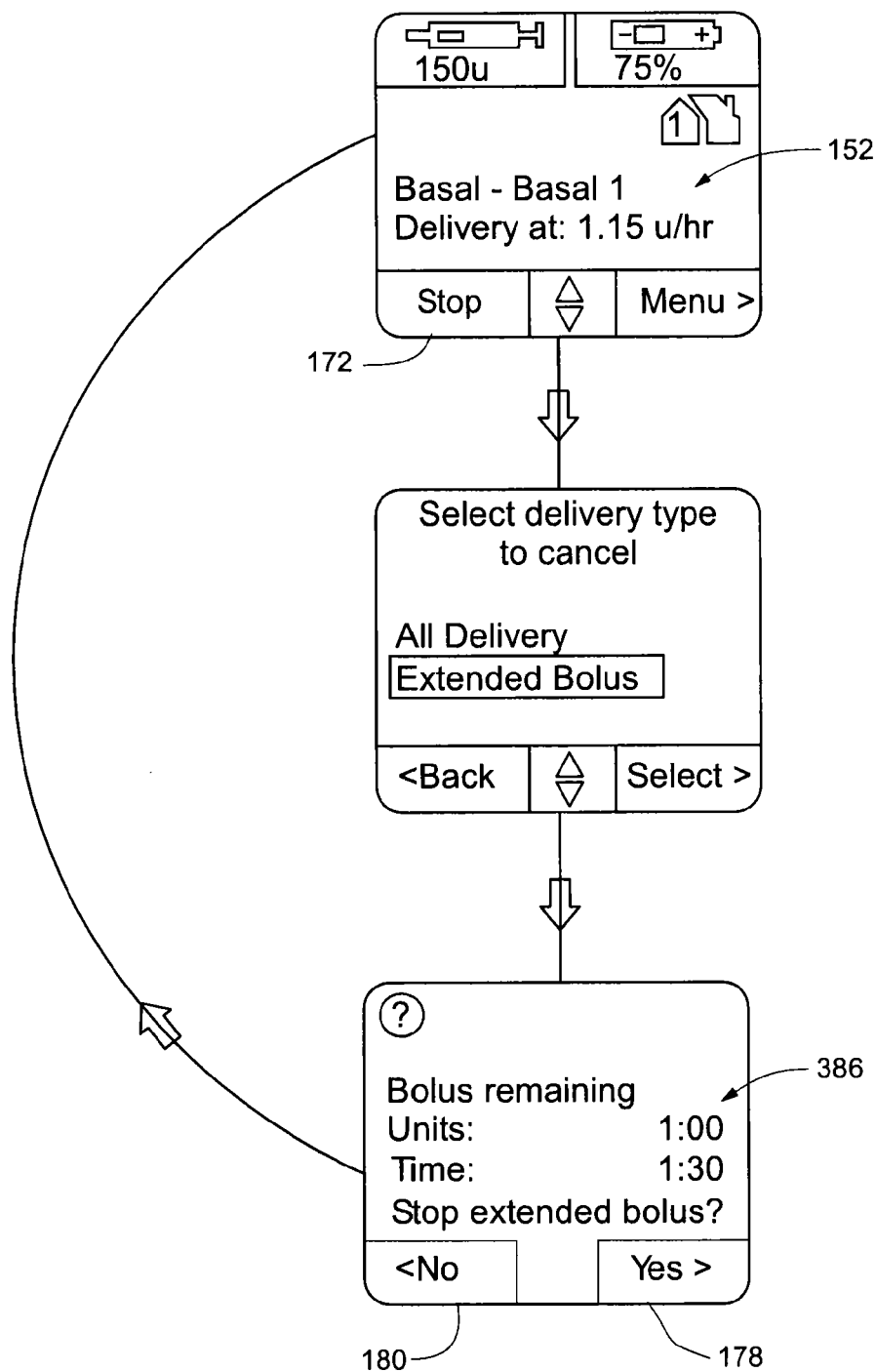

Referring to FIG. 22, the user can halt delivery of an extended bolus by activating the Stop function 172 on the home page 152. As described above, the pump 100 prompts the user to halt all delivery or just the extended bolus. The user selects the extended bolus. The pump 100 then prints the banner 386 indicating how much time remains in the duration for the extended bolus and how much of the extended bolus remains to be delivered. The pump 100 also prompts the user to confirm that insulin delivery is to be stopped. The user confirms by activating the Yes function 178. The pump 100 then stops delivery of the extended bolus and returns to pumping according to the normal basal rate. If the user activates the No function 180, the pump 100 will continue delivering according to the extended bolus and will return to the home page 152. The user optionally stops all delivery of insulin from the pump 100 using the All Delivery option.

Figure 23:
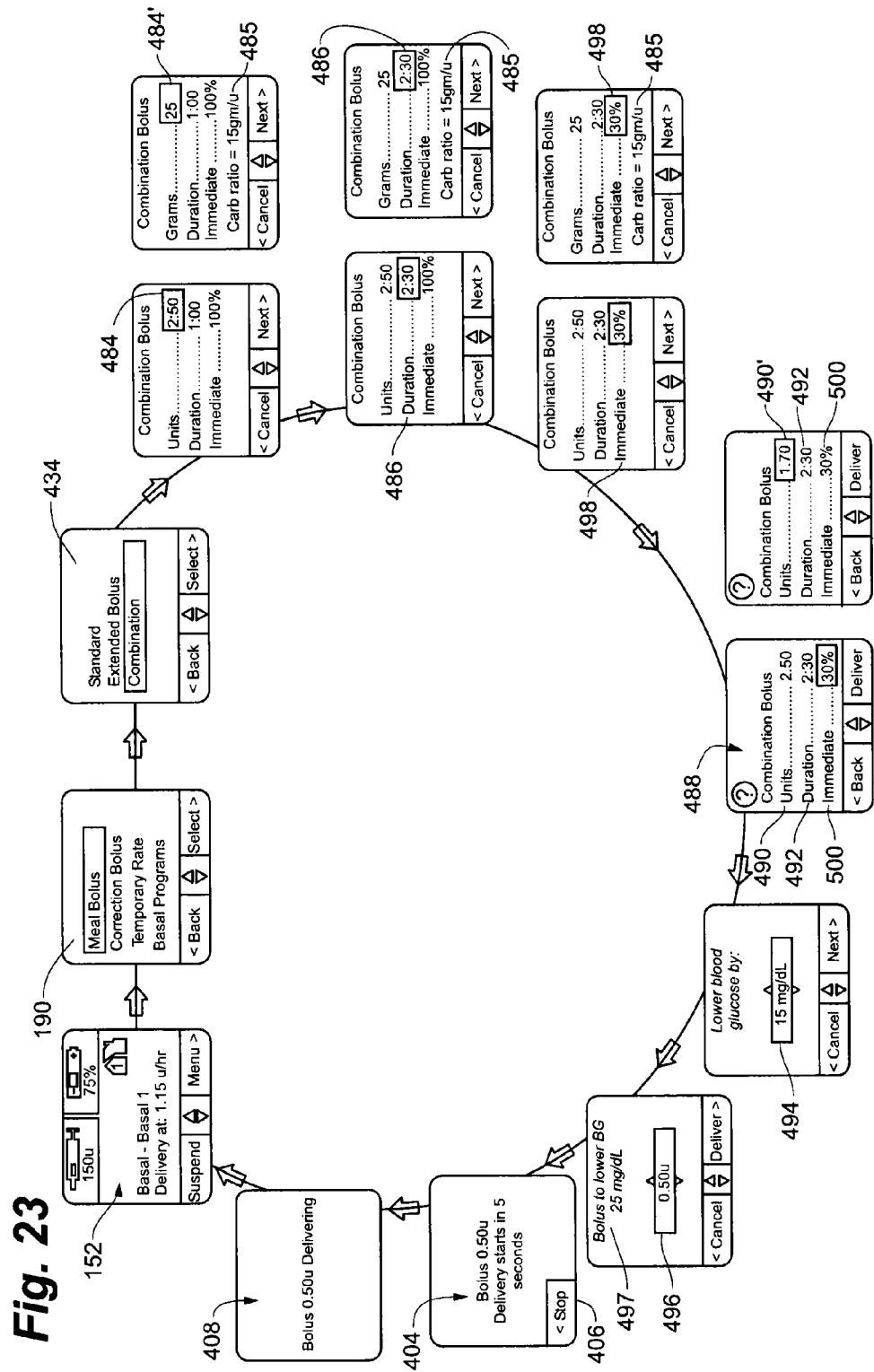

Referring to FIG. 23, delivery of a combination bolus is programmed into the pump in a manner similar to that of an extended bolus. However, the pump also prompts 498 the user to enter the proportion or percent of the bolus that the pump 100 delivers immediately upon activation of the Deliver function 384. To enter the proportion of the amount that is delivered immediately, the user scrolls through percentages until the desired percentage of the bolus for immediate delivery is set. In one possible embodiment, the user scrolls through percentages in the range from 0% to 100% in increments of 1. Additionally when programming the pump to deliver a combination bolus, the pump 100 displays 500 the percentage of the bolus that is to be delivered immediately in the confirmation user interface 488. In an alternative embodiment, the user enters the proportion or percent of the bolus that the pump 100 delivers over an extended period.

Figure 24:
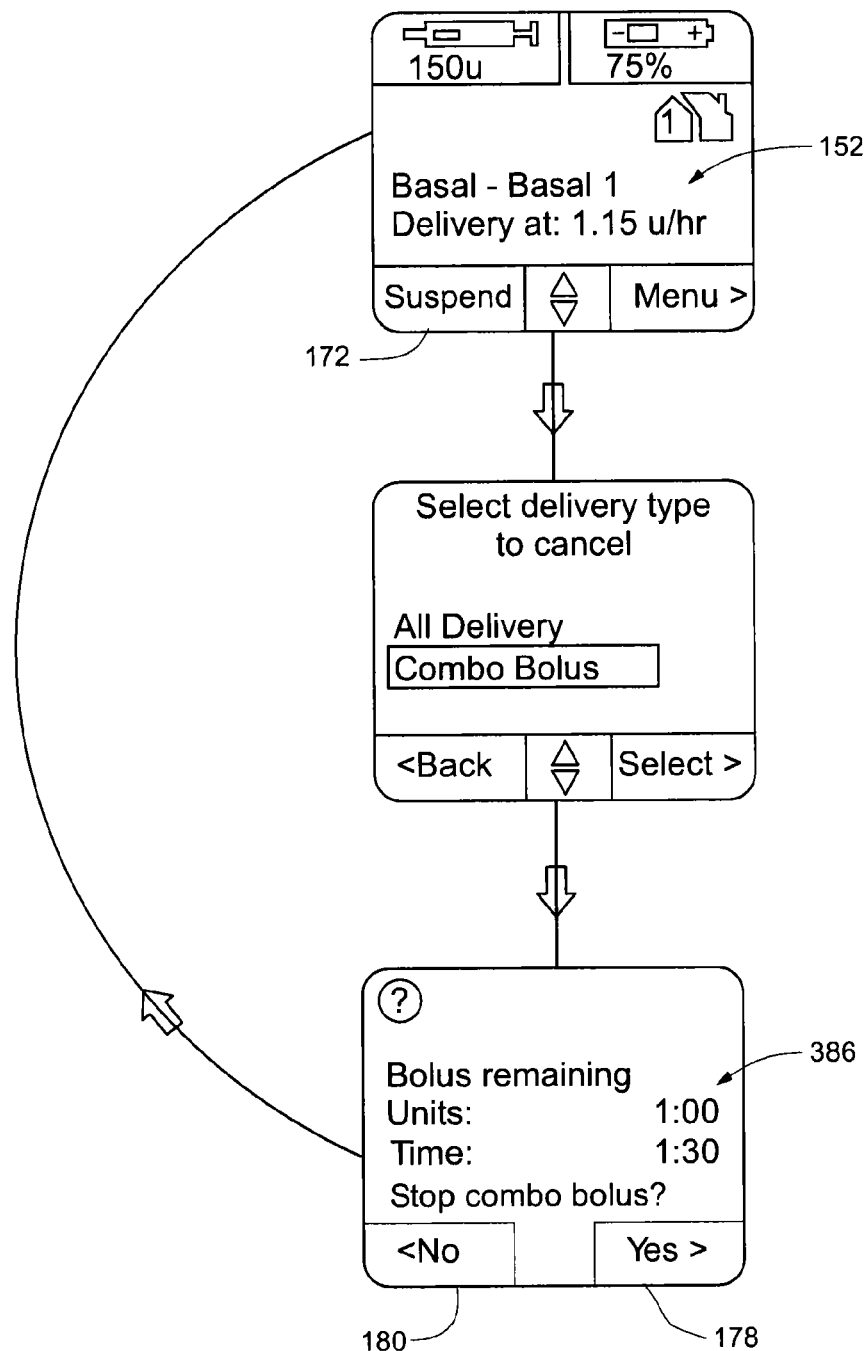

Referring to FIG. 24, the user can suspend delivery of a combination bolus in a manner substantially similar to that of the extended bolus except that the pump 100 displays a combination bolus menu item in the suspend menu. The user selects the combination bolus menu item to suspend delivery of the combination bolus, and then confirms suspension of the combination bolus.

L. Weekly Schedule

A weekly schedule can be created and preprogrammed into the pump 100. The weekly schedule allows the user to schedule a pattern of basal rates for individual days of the week, and also allows the user to schedule a set of missed meal bolus alerts for individual days of the week. The weekly schedule allows a user to preprogram one or more basal rates as described above in conjunction with FIGS. 10-11, and to preprogram one or more meal bolus alert sets as described above in conjunction with FIGS. 16-20.

Figure 25:
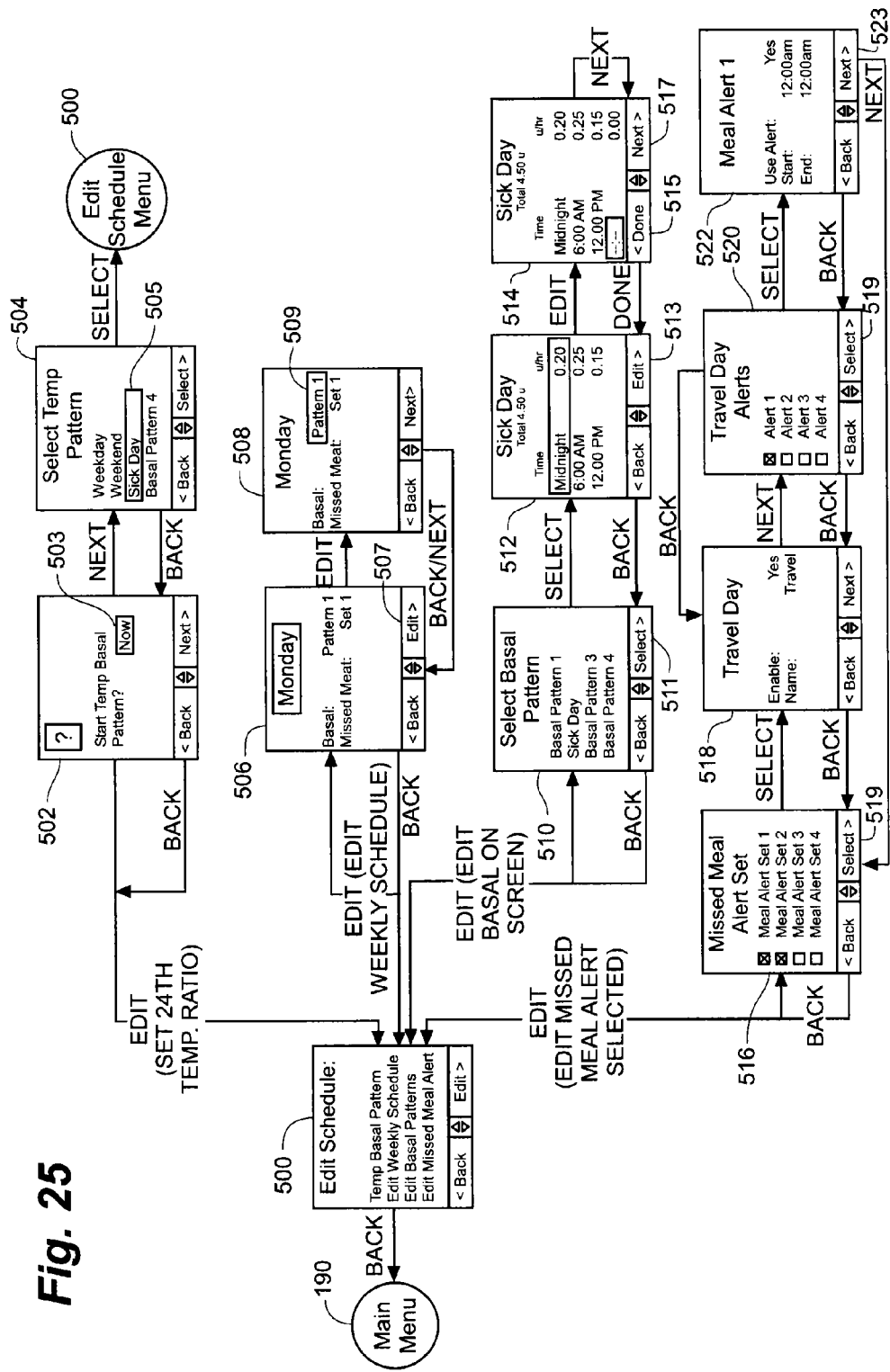
FIG. 25 illustrates the operations of setting and delivering an audio bolus on the pump shown in FIGS. 1 and 2.

Referring to FIG. 25, the pump 100 presents an editable weekly schedule to accommodate a user's specific insulin delivery requirements. For example each user may have varying meal times, activity levels, or insulin absorption rates which will affect the basal rate and bolus timing required of the pump 100. In the example shown, the user selects an Edit Schedule item optionally included in the main menu 190, and the pump 100 indexes focus to an edit schedule submenu 500. The edit schedule submenu 500 can be used in addition to or as a substitute for the basal programs option in the Personalize Delivery submenu 302 described above. The edit schedule submenu 500 lists the available editing options for the temporary rates, weekly schedule, basal patterns, and correction boluses. In the example shown, the menu items are displayed as "Temp Basal Pattern", "Edit Weekly Schedule", "Edit Basal Patterns", and "Edit Missed Meal Alert", respectively. Other menu items or names for menu items are possible as well.

The user selects one of the menu items to edit the corresponding aspect of the weekly schedule. If the user selects the Temp Basal Pattern option in the edit schedule submenu 500, the pump 100 indexes focus to a start temporary basal pattern screen 502 which allows the user to indicate when to start the temporary basal pattern. A temporary basal pattern is a basal pattern that overrides, for a day, the basal pattern scheduled in the weekly schedule. For example, if a pump user has to occasionally work on Saturday, they can schedule their "Weekday" pattern to temporarily override their "Weekend" pattern for the Saturday they must work. Selecting the Temp Basal Pattern option allows the user to have a temporary basal pattern applied by the pump 100 for the remainder of the current day and a second temporary basal pattern programmed to take effect the following day as well. A temp basal pattern start box 503 displays the time at which the temporary basal pattern will begin. In the start temporary basal pattern screen 502 shown, the temp basal pattern start box 503 indicates that the basal pattern will start immediately. To select a different time at which the temporary basal pattern will begin, the user can change the setting in the temp basal pattern start box 503 using the up and down keys. Other start times, such as delayed by an hour, a day, or other time period are possible. A back option returns focus to the edit schedule submenu 500.

Upon confirmation of the temp basal pattern start time by selecting a next option, the pump 100 indexes focus to a select temp pattern screen 504. The select temp pattern screen 504 prompts the user to select the temporary basal pattern that is to be applied. The user selects from the list of basal patterns 505 programmed or loaded into and enabled in the pump. In the example shown, "Weekday", "Weekend", "Sick Day", and "Basal Pattern 4" are listed as selectable options. Other lists or combinations of basal patterns can be displayed as well, depending upon the patterns created or loaded into the pump 100. The user selects one of the basal patterns using up and down keys 142, 144. Upon selection of a basal pattern and confirmation of the selection with a select option, focus returns to a main menu 190. A back option in the select temp pattern screen 504 returns focus to the start temporary basal pattern screen 502.

If the user selects the Edit Weekly Schedule option in the edit schedule submenu 500, the pump 100 indexes focus to a day program screen 506, which displays the basal pattern and missed meal pattern associated with that day. In the day program screen 506 shown, the day displayed is Monday, and the basal pattern is Pattern 1. The missed meal bolus alarm set is shown as Set 1. The up and down keys 142, 144 navigate through the days of the week, and an edit option 507 indexes focus to a day edit screen 508. The day edit screen 508 displays the basal pattern assigned to the day in a basal pattern field 509, and allows the user to edit the basal pattern for the day selected in the day program screen 506. The user changes the basal pattern using the up and down keys 142, 144, among the basal patterns edited using the Edit Basal Patterns option in the edit schedule submenu 500. The user also optionally selects a missed meal bolus alert set to associate with the selected day, from a listing of missed meal bolus alert sets programmed using the Edit Missed Meal Alert option in the edit schedule submenu. A back option and a next option both cause the pump 100 to index focus back to the day program screen 506.

If the user selects the Edit Basal Patterns option in the edit schedule submenu 500, the pump 100 displays a basal pattern listing 510 including basal patterns programmed into the pump. The basal pattern listing 510 displays one or more editable basal patterns which are available to be scheduled in the day edit screen 509 or used as temporary basal patterns in the select rate screen 504. The basal pattern listing 510 displays the defined basal patterns, and allows a user to select one of the predefined basal patterns using the up and down keys 142, 144. The user selects a back option to return to the edit schedule submenu 500, or selects a select option 511 to cause the pump 100 to index focus to a pattern view screen 512 related to the selected basal pattern. The pump 100 displays a listing of times and associated delivery rates in the pattern view screen 512 for the basal pattern selected in the basal pattern listing 510. If the user does not wish to edit the times displayed, the user selects a back option to return to the basal pattern listing 510. To edit one or more of the times and/or basal patterns, the user selects an edit option 513 to cause the pump 100 to index focus to a pattern edit screen 514. The pattern edit screen 514 displays on the pump 100 and allows the user to change the times and basal rates, or add additional times with associated basal rates. The user employs the up and down keys 142, 144 to select and edit the times of the day, as well as to select and edit the basal rates associated with the times of the day. A done option 515 indicates that the user has completed editing the basal pattern, and causes the pump 100 to index focus back to the pattern view screen 512. A next option 517 indexes focus within the pattern edit screen 514.

If the user selects the Missed Meal Alert option in the edit schedule submenu 500, the pump indexes focus to a missed meal alert listing 516. The missed meal alert listing 516 includes one or more sets of alerts configured to match the planned meal times of the user. The sets of alerts correspond to the alerts selected using the day edit screen 508. If the pump 100 does not deliver a meal bolus between the start and end time of a missed meal alert, the user may have forgotten to deliver the meal bolus and is prompted to deliver the meal bolus. The meal bolus can be programmed according to the meal bolus and food database description above. The user can select one or more missed meal alert sets using selection boxes associated with each of the missed meal alert sets. A select option 519 causes the pump to index focus to an alert enable screen 518.

The alert enable screen 518 displays the enabled or disable status of the missed meal alert set selected in the missed meal alert listing 516, and also displays the name of the alert set. A next option indexes focus to an alert listing 520 associated with the alert set displayed in the alert enable screen 518. A back option returns focus to the missed meal alert listing 516.

Upon user selection of the next option, the pump 100 indexes focus to the alert listing 520, which displays all of the defined missed meal alerts associated with a missed meal alert set. The user can select one or more of the alerts in the alert listing which the user wishes to edit. Upon selection of a select option 519, the pump 100 indexes focus to an alert edit screen 522. A back option returns focus to the alert listing screen 520.

The alert edit screen 522 allows the user to set a start time and an end time for the selected alert in the missed meal alert set. Upon selection of a next option 523 in the alert edit screen 522, the pump 100 returns focus to the missed meal alert listing 516. A back option in the alert edit screen 522 returns focus to the alert listing 520.

In a possible embodiment of the weekly schedule, the home screen 152 can be modified to display information related to the weekly schedule as programmed, such as the current day of the week, the type of day or basal rate currently applied, the name of the basal rate pattern, the missed meal alert set applied, or other information related to the weekly schedule.

Although specific examples are illustrated herein, the weekly schedule can be used to schedule basal rates, delivery patterns, and boluses for various events such as different daily meal schedules, upcoming athletic events, travel schedules, work schedules, sick days, parties, and any other type of schedule or event. Additionally, sets of scheduled target blood glucose levels, such as are related to a correction bolus or negative meal bolus, can be created. In an alternative embodiment, a weekly schedule could also be used to remind the user of other events such as testing blood glucose levels.

The weekly schedule disclosed herein is modifiable to provide to a user a monthly or yearly schedule as well. The monthly or yearly schedule can be programmed with monthly or yearly meal boluses, and can track holidays, vacations, or other events which occur outside the user's typical daily or weekly schedule.

M. Disconnect/Suspend Bolus

Referring back to FIG. 3, a disconnect/suspend bolus feature is included in the pump 100, and can be added to the main menu 190. The disconnect/suspend bolus feature 193 allows a user to disconnect from the pump 100 for up to two hours without missing delivery of insulin, although other embodiments will permit disconnecting the pump for periods greater than two hours. A user may want to disconnect from the pump 100 for a variety of reasons, such as for bathing, high levels of activity, or in other situations in which a pump may be inconvenient or unsafe.

When the user wishes to disconnect from the pump 100, the user is first prompted by the pump 100 to enter the duration they will be disconnected from the pump. The pump 100 calculates and displays the amount of insulin delivery which will be missed in that time. This includes any basal rate and temporary rate scheduled during that time. The pump 100 prompts the user to enter a percentage of the missed insulin that the user wishes to receive as a bolus prior to disconnecting from the pump, and accepts any percentage value up to 100% of the total insulin delivery that will be missed, although other embodiments might include a limit other than 100%. This percentage bolus delivered prior to disconnection can be referred to as a disconnect bolus.

The pump 100 prompts the user to optionally check their blood glucose level prior to disconnecting from the pump. If the user chooses to check their blood glucose level and requires a correction bolus, the correction bolus is delivered prior to disconnection. If the user chooses to check their blood glucose level and the negative meal bolus feature would normally activate, the pump 100 reduces the disconnect bolus to compensate for the user's low blood glucose level.

Upon confirmation by the user, the pump stops all basal rate delivery, logs the disconnection time, the percentage of immediately delivered insulin as selected, and delivers the disconnection bolus, which is the bolus amount calculated by the pump and multiplied by the percentage input by the user. Once the bolus delivery is complete, the pump 100 triggers an alarm, such as a visible alarm displayed on the pump or an audible alarm emitted by the pump, indicating to a user that they should disconnect from the pump. In the exemplary embodiment, the pump requests confirmation by the user that they are disconnected from the pump. Once confirmation is received from the user, the pump adds a "reconnect" option into the main menu 190. The pump stores its disconnected state and the elapsed disconnection time, such that the pump status is retained during the disconnect/suspend bolus operation even if the pump power is interrupted during the disconnect period, or if the user changes the time or date in the pump 100.

When the pump 100 remains in the disconnected state, the user can physically reconnect their infusion set and configure the pump to deliver a meal bolus or a correction bolus. The pump 100 maintains the interrupted basal rate during the time that the pump is in the disconnected state.

When the user begins the reconnect process by selecting the reconnect option on the main menu, the pump 100 calculates the originally scheduled insulin dose, which is the amount of insulin originally scheduled to be delivered during the elapsed time between the time the pump was disconnected and the time the reconnect option is selected on the main menu. The pump then subtracts the originally scheduled insulin dose from the dose delivered by disconnection bolus the dose. If the difference is a negative number, the user has reconnected before the time they had indicated, and the pump should not deliver additional insulin to the patient upon reconnection. The pump 100 starts a temporary rate of zero units per hour for the time required for the basal rate and boluses to make up for that negative amount. If the amount of insulin owed is a positive number, the pump 100 prompts the user to enter the percentage of that "missed" amount that they wish to have delivered, up to 100%. This percentage of missed insulin is referred to as the reconnect bolus.

The pump 100 prompts the user to optionally check their blood glucose level before reconnecting. If the user chooses to check their blood glucose level, any correction bolus deemed necessary will be added to the reconnect bolus. Likewise, if the user chooses to check their blood glucose level, any negative meal bolus will be subtracted from the reconnect bolus.

N. Additional Pump Features

Additional features can be included in the pump consistent with the present disclosure. For example, the pump can include programming for temporary basal rates, an option to include an audio bolus, customized alerts, and lock levels. A temporary rate allows the user to temporarily raise or lower the delivery rate being administered by the active bolus program. The user can personalize or customize the temporary rate programs and how they are present in the user interface. An audio bolus provides for delivery of a standard meal bolus using a single button. A series of sounds, such as beeps, are used to provide an indication of the setting to the user. In a possible embodiment, the beeps are configured analogously to the sounds used to program the pump 100 without the need for visual confirmation, such as by a visually impaired user. Customizable alerts allow a user to select specific alerts for various types of events occurring in the pump. Lock levels provide various levels of user rights in the pump based on access codes. Lock levels prevent unauthorized users from entering and changing settings in the pump. These and additional pump features are described in greater detail in U.S. Pat. No. 6,744,350, filed Feb. 28, 2002 and entitled Insulin Pump Having Missed Meal Bolus Alarm, the disclosure of which was incorporated by reference in its entirety above.

O. Computer-Pump Communication and Programming

In one possible embodiment, the pump 100 can communicate with a computer. The computer can upload information from the pump 100, including the historical information generated by and stored on the pump 100. The computer can archive the historical information and maintain a complete historical record about the pump 100. Additionally, the computer can generate various reports regarding use of the pump 100, including information about delivery rates, bolus amounts, and alarms. Additionally, the computer can operate a program that allows the user to enter operating parameters for the various delivery programs that are loaded on the pump 100 and to download those operating parameters to the pump 100. In yet another possible embodiment, the computer can be used to download delivery programs and software updates to the pump 100.

Figure 26:
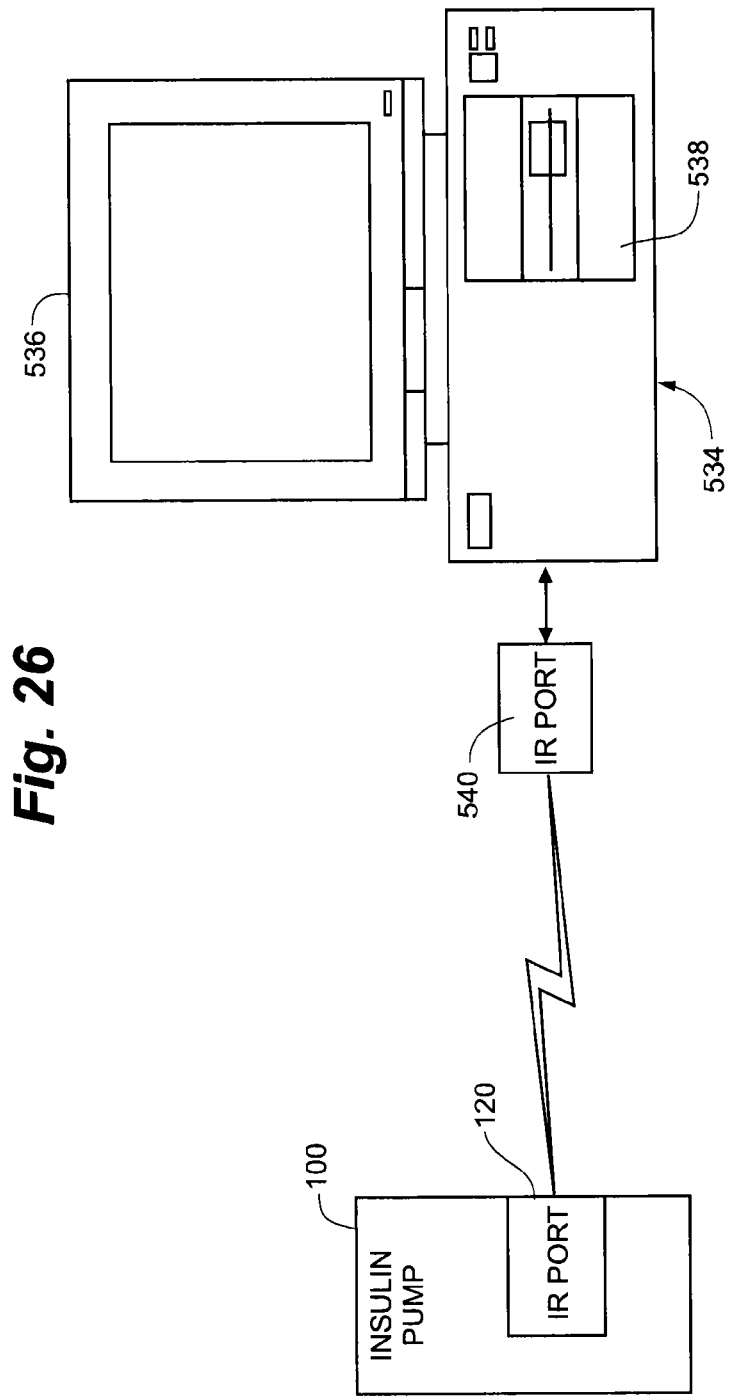
FIG. 26 illustrates the pump shown in FIGS. 1 and 2 communicating with a computer.

Referring to FIG. 26, in one possible embodiment, a computer 534 is a desktop computer that is IBM PC compatible, although other computers can be used. For example, the computer 534 could be an Apple computer, portable computer, a hand-held computer, a mainframe computer, a computer that is connected to a network. The computer 534 has a monitor 536, a storage device 538, and an infrared (IR) communication port 540. The pump 100 communicates with the computer through the IR port 120 on the pump 100 and the IR communication port 540 of the computer 534. In other embodiments, the pump 100 and computer 534 communicate through other types of data links such as a wireless or radio frequency (RF) connection or a wired connection such as USB, RS232, Fire wire, etc.

Communication between a medical pump and a computer is also discussed in U.S. Pat. No. 5,935,099, entitled Drug Pump Systems and Methods, the disclosure of which is hereby incorporated by reference.

Figure 27A:
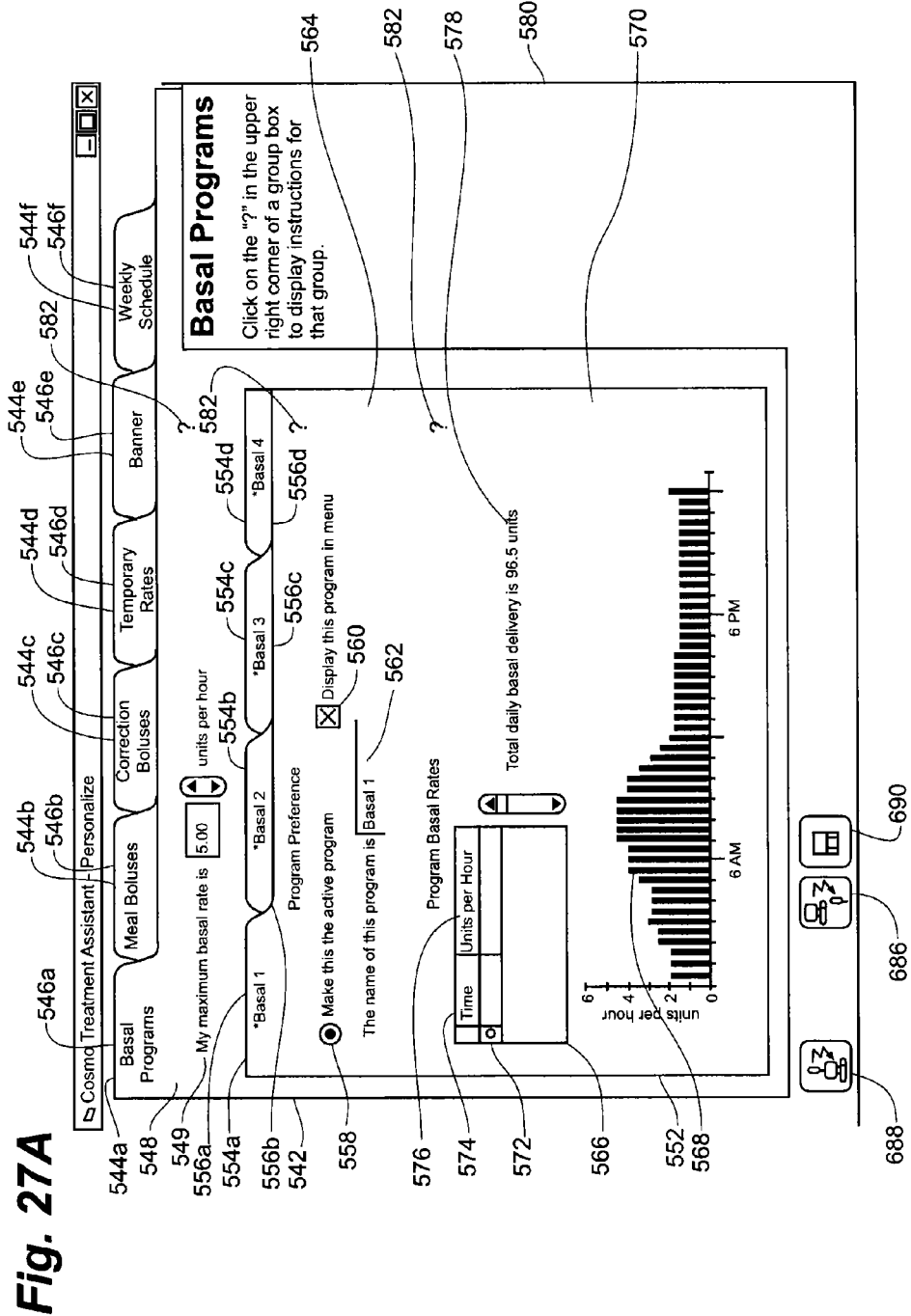
FIGS. 27A-27F illustrate a user interface on the computer illustrated in FIG. 26.

Referring to FIG. 27A, the software operating on the computer 534 generates a user interface 542 that allows a user to view, edit, and enter operating parameters for the various delivery programs that are loaded on the insulin pump 100. In one possible embodiment, the user interface 542 has a plurality of stacked primary windows 544*a*-544*e*. Each primary window includes a tab 546*a*-546*e* and data entry features for entering profile settings for the delivery programs. A basal programs primary window 544*a* is associated with the basal delivery programs, and is marked with a tab 546*a* bearing the name Basal Programs. A meal boluses primary window 544*b* is associated with the meal bolus delivery programs, and is marked with a tab 546*b* bearing the name Meal Boluses. A correction boluses primary window 544*c* is associated with the correction bolus deliver programs, and is marked with a tab 546*c* bearing the name Correction Boluses. A temporary rates primary window 544*d* is associated with the temporary rate delivery programs, and is marked with tab 546*d* bearing the name Temporary Rates. A banner window 544*e* can include display options for the pump 100, and is marked with tab 546*e* bearing the name Banner. A weekly schedules primary window 544*f* is associated with the weekly schedule programs, and is marked with tab 546*f* bearing the name Weekly schedule.

A primary window 544 can include a variety of different data entry features for entering the operating parameters including text, numbers, flags, or the like. Examples of the data entry features include buttons, check boxes, spin boxes, text fields, numeric fields, and tables. The buttons and check boxes are alternatively set and cleared by clicking on them with a pointing device such as a mouse. Each spin box is associated with up and down buttons and contains a list of values. The user sets the desired value by spinning though the list of values with the up and down keys until the desired value is visible in the spin box. The tables have rows of cells and a scroll bar. The user can manipulate the scroll bar with a pointing device to scroll through the available rows within the table. Additionally, each primary window has a download button, an upload button, and a save button.

The primary window on the top of the stack is active, and the user can enter, edit, and view operating parameters in the active primary window. The user can bring any one of the primary windows to the top of the stack by clicking on the primary window's tab.

Still referring to FIG. 27A, the first primary window 544*a*, which is for setting the operating parameters for the basal programs, has three panels. The first panel 548 has a spin box 550 for setting the maximum basal rate for the insulin pump. The spin box 550 is displayed in a first group box 549. The user spins though available values until the desired maximum basal rate is visible within the spin box 550. The maximum basal rate set in the spin box will apply to all of the basal delivery programs. In the illustrated example, there are four possible basal delivery programs. The first spin box 550 is present in a first group box.

The second panel 552 of the screen has one secondary window 554*a*-554*d* for each of the basal delivery programs. The secondary windows are stacked and are marked with tabs 556*a*-556*d*. Each tab 556 is marked with the name of the basal program associated with the tab's secondary window 554. The secondary window 554 on the top of the stack is active, and the user can enter, edit, and view operating parameters in the active secondary window. The user clicks on the tab 556 for any given secondary window to bring it to the top of the stack. In the illustrated example, there are four basal delivery programs and hence four secondary windows named Basal 1 554*a*, Basal 2 554*b*, Basal 3 554*c*, and Basal 4 554*d*.

Each secondary window 554 has a button 558, a check box 560, and a text field 562 organized into a second group box 564 for setting program preferences. A table 566 and a graph 568 are organized into a third group box 570 and are for naming, setting, and viewing the basal delivery rates. To activate a basal delivery program, the user sets the button 558 by clicking on it. Any other basal program that was active becomes inactive and the button for the previously active basal delivery program is cleared. Additionally, an asterisk is placed in the tab 556 for the active basal delivery program so that the user can easily identify the active basal delivery program if the secondary window 554 for that basal delivery program is not on top of the stack. When the operating parameters for the basal delivery programs are downloaded to the pump 100, the basal delivery program in which the button 558 is set will become the active basal delivery program on the pump 100.

To display the basal delivery program as a menu item in the Basal Program submenu 318 (FIG. 12) on the pump 100, the user sets the checkbox 560. When the operating parameters for the basal programs are downloaded to the pump 100, the name for the basal program is displayed as a menu item in the Basal Program submenu 318.

To customize the name of the basal delivery program, the user types the custom name into the text field 562. The custom name is assigned to the basal delivery program and appears in the tab 556 for that program. Additionally, the custom name is the name downloaded into the pump 100 and appears in the Basal Program submenu 318, if the checkbox 560 is set. In an alternative embodiment, a spin box is associated with the text field 562. The spin box presents preprogrammed, optional names for the basal delivery programs that the user can select. The selected name would then replace the generic name (e.g., Basal 1, Basal 2, Basal 3, and Basal 4 in the illustrated example) for the program associated with the display. Examples of optional names that might be loaded in the pump 100 include weekday, weekend, sick, and monthly (which is to designate a basal delivery program set for a woman's menstrual cycle).

The basal rate table 566 or grid has a plurality of rows 572 and each row has two cells 574 and 576. When a cell within the table 566 has focus and the user presses the enter key or the tab key, the focus shifts to the next cell to the right. If the current cell is the last cell in the row, focus shifts to the first cell in the next row. If the user presses the enter key while the last cell in the last row is in focus, a new row is created. In this manner, the user can expand the length of the table 572. If the user presses the enter key while the last cell of a row is in focus and there is no data in any cell within that row, the computer will delete the row. The one exception is the first row in the table, which cannot be deleted.

The first cell within a row is a start-time cell 574, and the second cell within a row is a delivery-rate cell 576. Each row corresponds to a different interval in the delivery protocol for the basal delivery program. To set the delivery protocol for a basal program, the user enters the start time for each delivery interval in the start-time cell 574 and the delivery rate in the delivery-rate cell 576. The pump 100 will then deliver at the set delivery rate beginning at the set start time and until the start time for the next delivery interval. In one possible embodiment, the start time for the first interval is 12:00 midnight and cannot be changed.

Accordingly, to set the delivery protocol for the basal delivery program, the user types the start time in the start-time cell 574, hits the enter key and changes the focus to the delivery-rate cell 576 to the right. The user then types in the delivery rate for that interval, hits the cell key, and changes the focus to the start-time cell in the next row (creating the row if the next row does not already exist). A new row will appear in which the user can enter the operating parameters for another delivery interval. The user continues this process until the operating parameters for all of the desired intervals are entered into the table.

In an alternative embodiment, when a cell has focus, a spin box having up and down buttons is presented in that cell. The user can either type a value into the spin box or spin through values until a desired value is visible in the spin box. When the cell and hence the spin box loses focus, the visible value from the spin box is entered into the corresponding cell and the spin box becomes invisible.

The graph 568 provides a graphical illustration of the delivery rate for the basal delivery program over a 24-hour period. In one possible embodiment, the graph 568 is a bar chart illustrating the delivery rate in a resolution of 30 minutes. In the illustrated example, Basal 1 is set to deliver 2 units/hour from 12:00 midnight to 2:00 am, 2.5 units/hour from 2:00 am to 3:00 am, etc.

In one possible embodiment, the graph 568 is automatically updated as the user completes entering the start time and delivery rate for each delivery interval. Additionally, the total daily basal rate is displayed 578, and is automatically calculated and updated as the user completes entering the start time and delivery rate for each delivery interval. Entry of data for an interval is complete when the user enters the start time and delivery rate for the interval and exits both the start-time cell 574 and the delivery-rate cell 576.

The third panel 580 presents instructions to the user. In one possible embodiment, the user interface presents a help label 582 (e.g., the question mark in the illustrated example) in each of the group boxes 549, 564, and 570. When the user clicks on a help label 582, instructions specific to the group box or other aspects of the user interface associated with the help label are presented in the third panel. Alternatively, the user can point to a particular aspect of the user interface and right click on the mouse to present field-specific instructions in the third panel.

An additional panel (not shown) can include control options for performing a basal test. The additional panel will include options to set up and review the results of the basal test. The additional panel will have analogous functionality to that described above in conjunction with FIGS. 7-9.

Figure 27B:
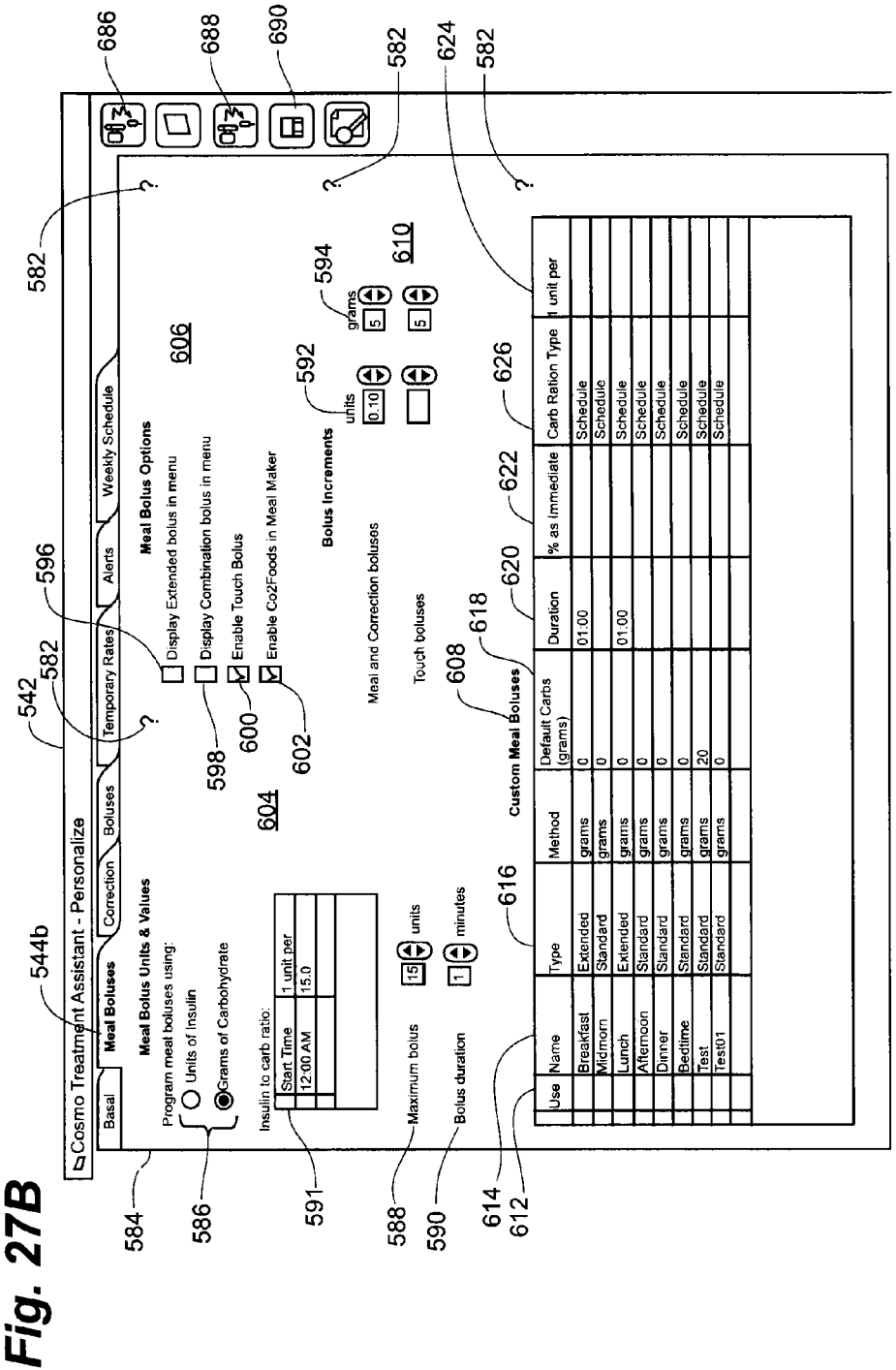

FIG. 27B illustrates the second primary window 544b, which is for setting the operating parameters of the meal bolus delivery programs. The meal bolus primary window includes two panels. The first panel 584 has a pair buttons 586, a first spin box 588, a second spin box 590, a third spin box 592, a fourth spin box 594, a first check box 596, a second check box 598, a third check box 600, a fourth check box 601 and a meal bolus table 602.

The pair of buttons 586, spin boxes 588, 590 and table 591 are present in a first group box 604. The check boxes 596, 598, 600, and 601 are presented in a second group box 606, and the table 602 is present in a third group box 608. Spin boxes 592 and 594 are present in a fourth group box 610. The pair of buttons 586 is for setting the meal bolus delivery program to use either units of insulin or grams of carbohydrates. The pair of buttons 586 toggle between set and cleared states so that when one is set the other cleared. The user set the first button to program the meal bolus programs in units of insulin and sets the second button to program the meal bolus programs in grams of carbohydrates The first spin box 588 is for setting the maximum bolus that the pump 100 can deliver when executing the meal bolus program. The second spin box 590 is for setting the duration of the bolus. The table 591 is for setting the user's fixed carbohydrate ratio. The table 591 optionally also works in conjunction with functionality to set a schedule of carbohydrate ratios configured to change based on the time of day.

In the fourth group box 610, the spin box 592 is for programming in units of insulin and is for setting the increments at which a user can spin through bolus amounts. The spin box 594 is for programming in grams of carbohydrates and is for setting the increments at which a user can spin through grams of carbohydrates to be consumed in a meal.

When the user sets the first button for programming in units of insulin, the third spin box 592 is enabled and the fourth 594 spin box is disabled. When the user sets the second button for programming in grams of carbohydrates, the fourth 594 spin boxes is enabled, and the third spin box 592 is disabled.

To enable the extended bolus program, the user sets the first check box 596. To enable the combination bolus program, the user sets the second check box 598. To enable the audio bolus function, the user sets the third check box 600.

To enable to food database, the user sets the fourth check box 602. Selection of the fourth check box 602 can optionally trigger creation of another window (not shown) used for browsing a food database stored on the computer.

The custom meal bolus table 608 has a plurality of rows, and each row has a plurality of cells. The user navigates through the meal bolus table 608 using procedures substantially similar to that of the basal rate table. Also similar to the basal rate table, the custom meal bolus table 608 can have various spin boxes that become visible when a cell has focus. The spin boxes are for entering values and pre-typed text into the cell with which it is associated.

Within the meal bolus table 608, each row has seven cells. The first cell 612 has a check box 613. To enable the custom meal bolus defined by that row, the user sets the check box 613. The second cell 614 has a text field in which the user types a name to identify the custom meal bolus defined by that row. An example includes pizza, when the operating parameters for the custom meal bolus are customized to deliver insulin for working against a meal of pizza. Other examples, might include breakfast, lunch, dinner, snack, or any other specific type of food, drink, or meal.

The third cell 616 contains a text field for entering the type of custom meal bolus, whether it is a standard bolus, an extend bolus, or a combination bolus. In one possible embodiment, a spin box is presented in the third cell 616 when focus is placed on the cell. The user can then spin through the types of bolus (e.g., standard, extended, or combination) and set the desired type. The fourth cell 618 is a numeric field for entering the default number of carbohydrates to be delivered by the bolus program defined by that row. The fifth cell 620 is a duration field in which the user enters the duration of the bolus delivery if the bolus program defined by that row is an extended bolus or a combination bolus. The sixth cell 622 is a numeric field in which the user enters the percent of the bolus to be delivered immediately if the bolus program defined by that row is a combination bolus.

The seventh cell 626 contains a text field for entering the type of carbohydrate ratio entered into the pump 100. In the embodiment shown, the carbohydrate ratio is either a Fixed or Scheduled ratio. When a Scheduled carbohydrate ratio is selected, the custom bolus uses the carbohydrate ratio that is currently in use by the pump 100. If a Fixed carbohydrate ratio is selected, the custom bolus uses the carbohydrate ratio entered in the eighth cell 624. In one possible embodiment, a spin box is presented in the seventh cell 626 when focus is placed on the cell. The user can then spin through the types of carbohydrate ratios (e.g., Fixed or Scheduled) to set the desired type. The eighth cell 624 is a numeric field in which the user enters the carbohydrate ratio the pump 100 is to use when the seventh cell is set to Fixed. The carbohydrate ratio is used when calculating the bolus amount to deliver. The eighth cell 624 allows the user to enter a customized carbohydrate ratio independent of the carbohydrate ratio schedule. For example, a user might use one carbohydrate for a custom meal bolus to be delivered before an early morning breakfast and a different carbohydrate ratio for a custom meal bolus to be delivered prior to an exercise session.

If the type of meal bolus set in the third cell (Type of Meal Bolus) 616 is standard, the fifth cell (Duration) 620 and sixth cell (% as Immediate) 622 are disabled and cleared. If the type of meal bolus set in the third cell 616 is an extended bolus, the fifth cell 620 is enabled and the sixth cell 622 is disabled and cleared. If the type of meal bolus set in the third cell 616 is set as a combination bolus, the fifth 620 and sixth 622 cells are enabled.

Also, the fourth cell 618 allows a default number carbohydrates for the custom bolus to be entered. For example, if a user eats a 40 gram carbohydrate snack before bed each night, a custom meal bolus called "Bedtime Snack" could be created with a default carbohydrate value of 40 grams. The default value can be adjusted before the bolus is delivered.

An optional second panel (not shown) in the primary window 544b for the meal bolus delivery program presents instructions. It operates in a manner substantially similar to the third, instruction panel 580 in the first primary window 544a for the basal rate delivery programs as described above.

Figure 27C:
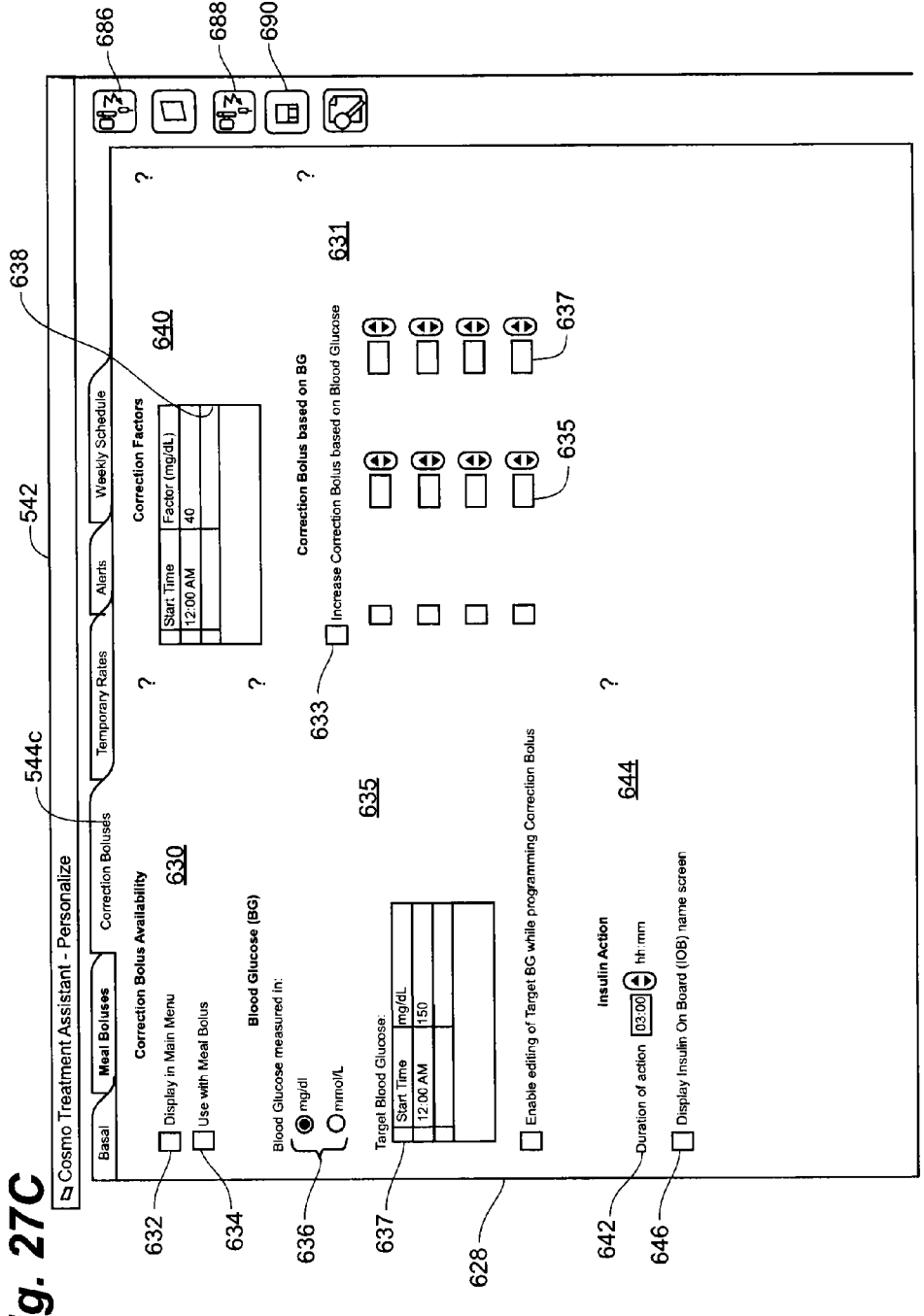

FIG. 27C illustrates the third primary window 544c, which is for setting the operating parameters for the correction bolus delivery program. The primary window 544c can contain two panels. The first panel 628 has buttons, check boxes, and spin boxes. A first group box 630 in the first panel 628 has first and second check boxes 632 and 634. To control the pump 100 to make the correction bolus delivery program available through the main menu 190 and to display a correction bolus menu item in the main menu 190, the first check box 632 is set. To make the correction bolus program available through the meal bolus delivery programs described above, the second check box 634 is set.

A table control 638 resides within a second group box 640, and sets a schedule of correction factors. The correction factors define operating parameters used by the correction bolus program. The table control allows the user to define a start time and a Factor, which refers to the amount of correction which could occur at that time of day. Alternately, a pair of buttons set the units for the operating parameters used by the correction bolus program. The pair of buttons toggle between set and cleared states so that when one is set the other is cleared. The first button is set to use mg/dL and the second button is set to use mmol/l. A first spin box is for setting the correction bolus factor. When the first spin box is in focus, the user spins through value until the desired correction factor is set. The pair of buttons and the first spin box are optionally organized into the second group box 640.

A third group box 635 has buttons and a table control. The buttons 636 set the method by which blood glucose is measured. In the embodiment shown, the buttons 636 allow a user to select between units of mg/dl and mmol/L. The table control 637 defines one or more target blood glucose levels and associates the target blood glucose levels with times of the day. In an optional embodiment, the table control 637 allows a user to define a schedule or target blood glucose levels for one or more days.

A fourth group box 644 in the first panel 628 has buttons and spin boxes. A second spin box 642 is for setting the duration of activity or action for the insulin. As discussed above, the duration of activity is the length of time that each bolus remains working in the user's body. To enter the duration of activity, the user spins through values in the second spin box 642 until the desired value is set. Optional spin boxes (not shown) set the start time and tail time of an insulin absorption model. To enter the start and tail times, the user spins through the values in the respective spin boxes until the desired values are set. Buttons may set the insulin absorption model to be used in the pump by toggling between set and cleared states so that when one is set the other two buttons are cleared. Each button can correspond to a linear absorption model such as is shown in FIG. 14A, a nonlinear absorption model, such as is shown in FIG. 14C, or a custom absorption model, using a graphical user interface which optionally appears upon selection of the button (not shown).

A fifth group box 631 enables and sets the change in the correction factor based on the user's blood glucose level. A check box 633 enables changes in the correction factor based on the user's current blood glucose level, of the form "If blood glucose is at least X, add Y %." A series of spin boxes 635 set the threshold blood glucose reading at which the rule takes effect for one or more rules, and represents the "X" value in the above statement for each selected rule. A second series of spin boxes 637 sets the percentage increase in insulin delivery upon reaching the threshold blood glucose level, and represents the "Y" value in the above statement for each corresponding selected rule. In the implementation shown, four separate sets of spin boxes are used to set four blood glucose dependent rules for insulin delivery. However, more or fewer sets of spin boxes are included according to specific implementations of the group box 631 and correction factors.

An optional second panel (not shown) in the primary window 544c for the correction bolus delivery program presents instructions. It operates in a manner substantially similar to the third, instruction panel 580 in the first primary window 544a for the basal rate delivery programs as described above.

Figure 27D:
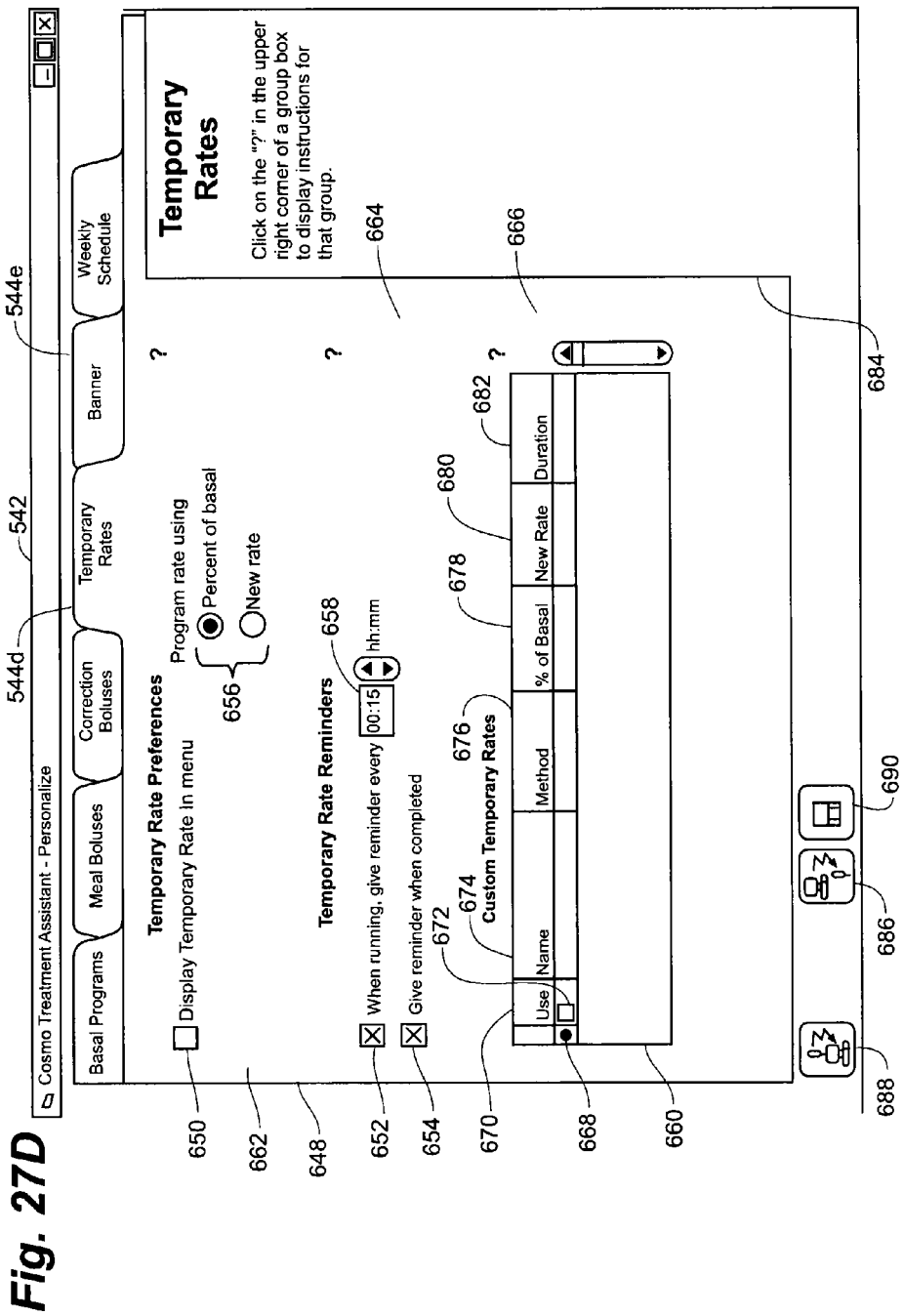

FIG. 27D illustrates the fourth primary window 544d, which is for setting operating parameters for the temporary rate programs. The primary window 544d has two panels. The first panel 648 has a first check box 650, a second check box 652, a third check box 654, a pair of buttons 656, a spin box 658, and a temporary rate table 660. The first check box 650 and pair of buttons 656 are in a first group box 662. The second 652 and third 654 check boxes and the spin box 658 are in a second group box 664. The table 660 is in a third group box 666.

The pair of buttons 656 sets the temporary rate either as a percentage of the running basal rate or as a new temporary basal rate. The pair of buttons 656 toggle between set and cleared states so that when one button is set the other button is cleared. The user sets the first button to set the temporary rate as a percent of the basal rate. The user sets the second button to set the temporary rate as a new, temporary basal rate.

To set a reminder so that the pump 100 intermittently generates a reminder (audible and/or vibratory) while the temporary rate program is running, the user sets the second check box 652. When the second check box 652 is set, the spin box 658 is enabled. The spin box 658 is for setting the interval between reminders. The spin box 658 is disabled when the second check box 652 is cleared. To set the pump 100 to generate a final reminder upon completion of the temporary rate, the user sets the third check box 654.

The temporary rate table 660 has a plurality of rows 668, and each row 668 contains a plurality of cells. The user navigates through the temporary rate table 660 using procedures substantially similar to that of the basal rate table. Also similar to the basal rate table 602, the temporary rate table 660 can have various spin boxes that become visible when a cell has focus. The spin boxes are for entering values and pretyped text into the cell with which it is associated.

Within the temporary rate table 660, each row has six cells. The first cell 670 has a check box 672. To enable the temporary rate defined by that row, the user sets the check box 672. The second cell 674 has a text field in which the user types a name to identify the temporary rate defined by that row. Examples might include exercise, 5-mile run, sick, evening, and the like. The third cell 676 is a text field to set the temporary rate to be programmed as a percent of current basal rate or as a new rate. In one possible embodiment a spin is present in the third cell 676 when focus is place on the cell. The user then spins through the types of temporary rates (e.g., % of Basal or New Rate) and sets the desired type.

The fourth cell 678 is for assigning the percentage of the running basal rate to set as the temporary rate. The fifth cell 680 is for setting a new rate for the temporary rate. When the user enters % of basal in the third cell 676, the fourth cell 678 is enabled and the fifth cell 680 is disabled. When the user enters New Rate in the third cell 676, the fourth cell 678 is disabled, and the fifth cell 680 is enabled. The sixth cell 682 is for setting the duration of the temporary rate.

Additionally, in one possible embodiment, when the user sets the first button to adjust the delivery rate as a percent of the basal rate, the check box 672 is set in the first cell 670 for each row 668 in which there is a percentage in the fourth cell 678. The check box 672 in the first cell 670 is cleared for each row 668 in which there is a delivery rate value in the fifth cell 680. Similarly, when the user sets the second button to use a new delivery rate, the check box 672 is set in the first cell 670 for each row 668 in which there is a delivery rate value in the fifth cell 680. The check box 672 in the first cell 670 is cleared for each row 668 in which there is a percentage value in the fourth cell 678.

The second panel 684 in the primary window 544*d* for the temporary rate delivery programs presents instructions. It operates in a manner substantially similar to the third, instruction panel 580 in the first primary window 544*a* for the basal rate delivery programs as described above.

In addition to operating parameters, one possible embodiment of the user interface 542 also enables a user to view, edit, and enter other data, character strings, and settings that are loaded on the insulin pump 100.

Figure 27E:
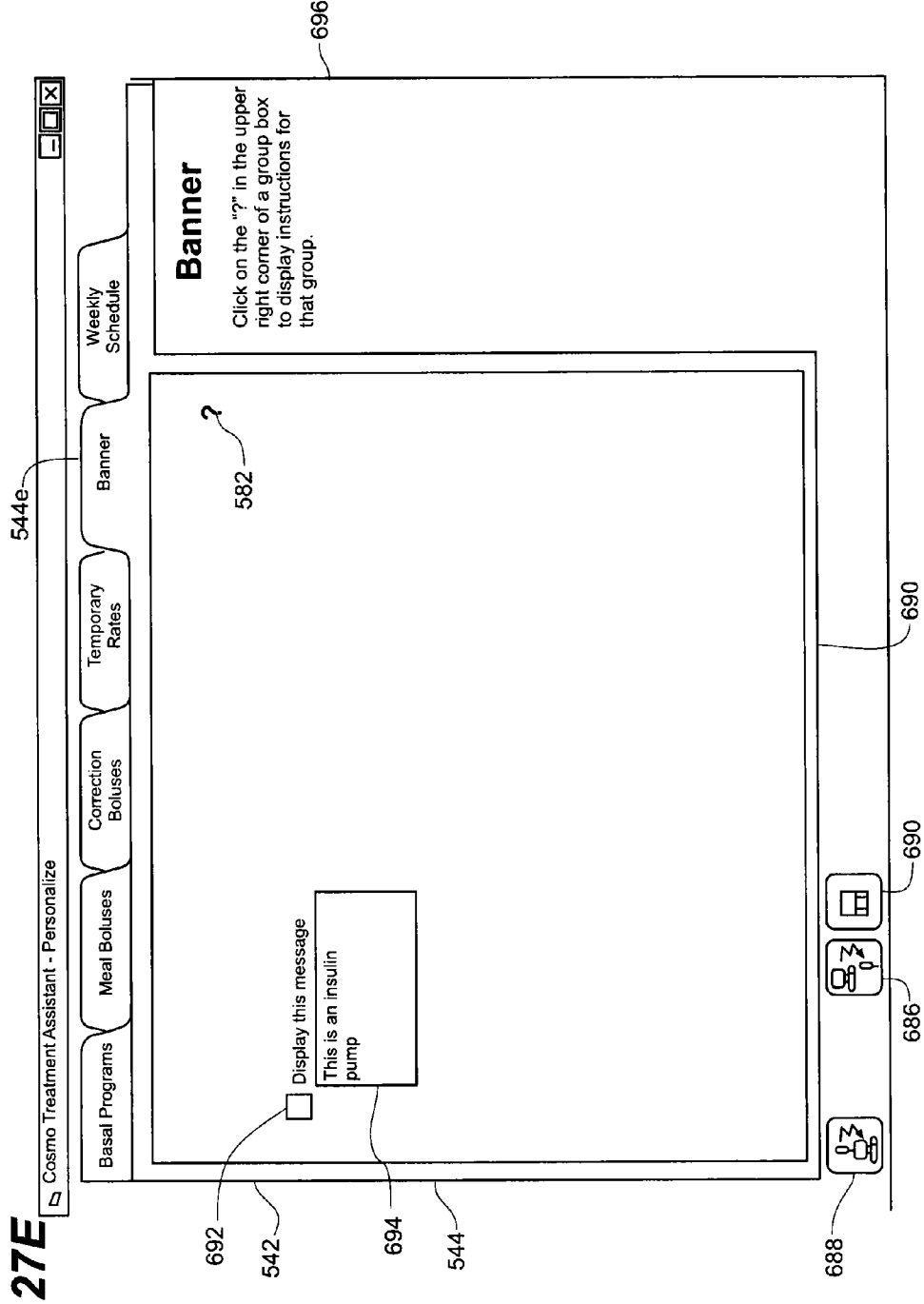

For example, FIG. 27E illustrates the fifth primary window 544*e*, which is for setting the banner displayed in the home page 152 of the pump 100. Primary window 544*e* is in the stack of primary windows 544. The fifth primary window 544*e* includes two panels. The first panel 690 has a field check box 692 and a text field 694 mated to the checkbox 692. To enter text into the home page 152, the user sets the checkbox 692 and enters text (numbers and letters as desired) into the text field 694. If the pump 100 includes multiple home pages 152 through which the user can scroll, an embodiment of the primary window 544*e* includes a checkbox 692 and mating text field 694 for each of the home pages 152. The user can then designate certain text for a particular home page 152 by setting the checkbox 692 associated with that home page 152 and entering text into the mating text field 694. In an alternative embodiment, if the text in the text field 694 is too long to fit into one display, the pump 100 automatically generates multiple home pages 152 through which the user can scroll and divides the text from the text field 694 between the multiple home pages 152. In another embodiment, similar text fields and associated checkboxes can be used to customize displays and messages for particular alarms, alerts, and reminders.

The second panel 696 in the primary window 544*e* presents instructions. It operates in a manner substantially similar to the third, instruction panel 580 in the first primary window 544*a* for the basal rate delivery programs as described above.

Figure 27F:
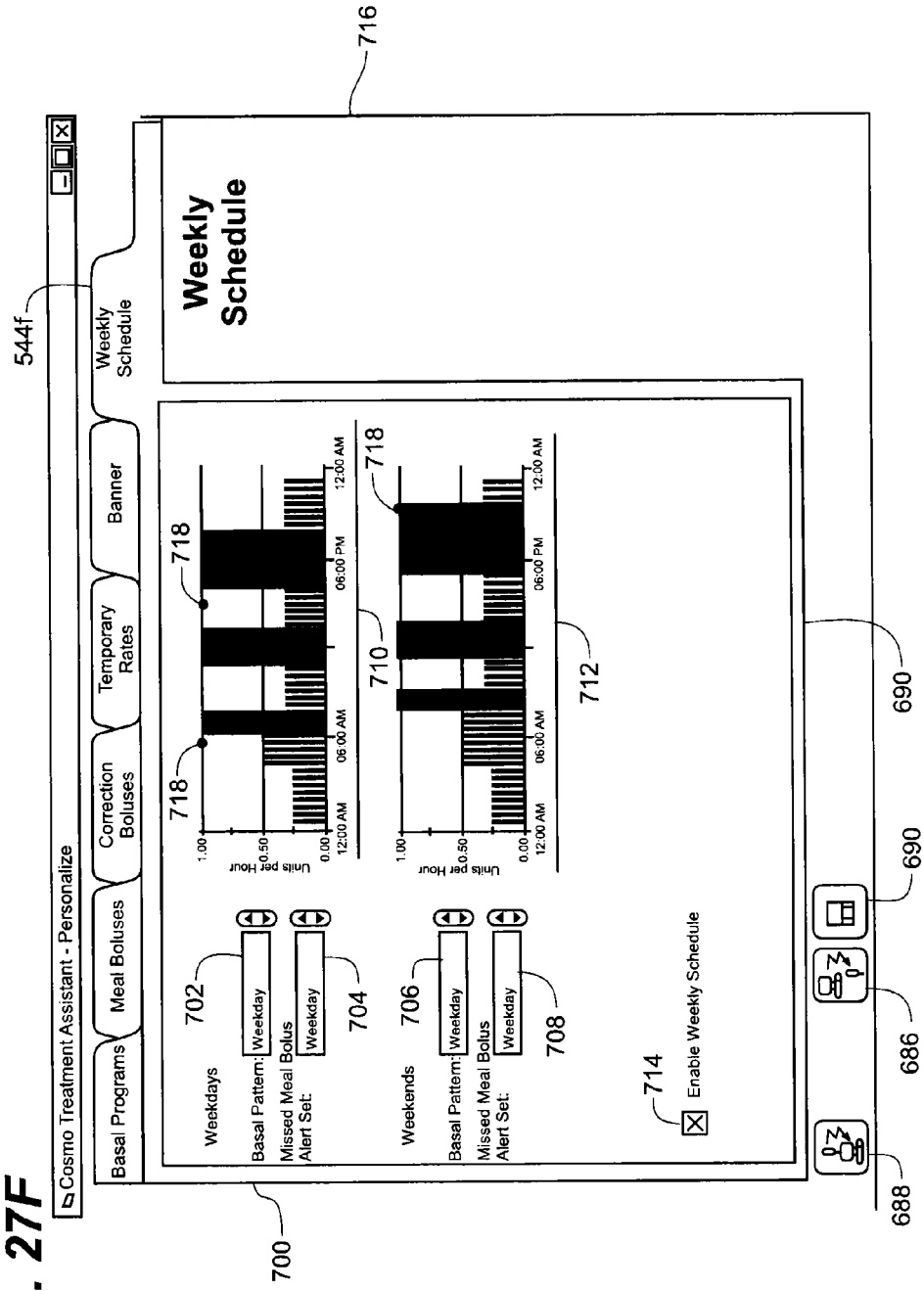

FIG. 27F illustrates the sixth primary window 544*f*, which is for programming basal delivery patterns in a weekly schedule, as described above in conjunction with FIG. 25. The sixth primary window 544*f* includes two panels. The first panel 700 has a first spin box 702 and a second spin box 704 configured to set the basal pattern and missed meal bolus alerts for weekday operation. To select a weekday basal pattern, the user can spin through the listed basal patterns programmed in the basal patterns tab 544*a* and set the desired type. To select a weekday missed meal alert set, the user can spin through the listed alert sets configured in the meal boluses tab 544*b* and set the desired type. The first and second spin boxes 702, 704 correspond to a graphical representation 710 of the weekday schedule. The graphical representation displays the basal rates and the missed meal bolus alert times that are selected using the spin boxes 702, 704 on an hour by hour basis.

The first panel 700 also has a third spin box 706 and a fourth spin box 708 configured to set the basal pattern and missed meal bolus alerts for weekend operation. To select a weekend basal pattern, the user can spin through the listed basal patterns programmed in the basal patterns tab 544*a* and set the desired type. Likewise, to select a weekend missed meal alert set, the user can spin through the listed alert sets configured in the meal boluses tab 544*b* and set the desired type. The first and second spin boxes 706, 708 correspond to a graphical representation 712 of the weekend schedule, which displays the basal rates and meal bolus alerts analogously to the weekday graphical representation 706. In an alternative embodiment, the first panel 700 can include seven spin box controls, corresponding to each day of the week. In a further alternative embodiment, the first panel 700 can include a graphical calendar display configured to allow monthly programming of the basal pattern and/or missed meal bolus alerts.

A first check box 714 enables the weekly schedule option in the software and on the pump 100. The first check box 714 is by default in a checked, or enabled, state.

One or more indicators 718 correspond to alarms scheduled to occur during the day displayed. The indicators and corresponding alarms can represent appointments, times of the day at which blood glucose values should be checked, or other user reminders.

The second panel 716 in the primary window 544*f* presents instructions. It operates in a manner substantially similar to the instruction panel 580 in the first primary window 544*a* for the basal rate delivery programs as described above.

Yet other embodiments of the user interface 542 include various windows, buttons, checkboxes, spin boxes, and fields for setting other parameters used to operate the pump 100. Examples of such other parameters that can be set through the user interface 542 include various format settings, alarms, reminders, operating limits, report formats, security settings, character strings, and indeed any other operating parameters, data, settings, and character strings that can be programmed into the pump 100.

Referring to FIGS. 27A-27F, to download the operating parameters displayed in an active primary window 544, the user clicks on the download button 686. The operating parameters relating to the active primary windows are then downloaded into the pump 100 over the communication link. The pump 100 returns the downloaded operating parameters to the computer 534, which compares the returned operating parameters to the sent operating parameters. If the returned and sent operating parameters match, the computer 534 sends a handshake signal to the pump 100 and the microprocessor 102 maps each of the downloaded operating parameters to its designated memory addresses in RAM 116 and saves the downloaded operating parameters in RAM 116. If the returned and sent operating parameters do not match, the computer 534 generates an error signal and sends the error signal to the pump 100. The pump 100 then discards the downloaded operating parameters and preserves the preexisting operating parameters already stored in RAM 116.

To upload operating parameters from the pump 100 into the active primary window 544, the user clicks the upload button 688. The profile settings in RAM 116 that correspond to the active primary window 544 are then retrieved from RAM 116 on the pump 100 and are sent to the computer 534. The uploaded operating parameters are then populated into the fields of the active primary window 544, including all secondary windows 554. To save the profile settings, the user clicks the save button 690. The profile settings that populate the active primary window 544 then are saved in the storage device 538. In one possible embodiment, the name of the file that includes the saved data is the name of the pump user.

Furthermore, the user interface 542 can be used on the computer 534 to program and manage pumps 100 for several different pump users. In one such embodiment, the computer 534 is programmed with an initial interface that includes a text field in which the name of the pump user is entered either through the computer keyboard or through a spin box. Upon entering the name of the pump user, the computer 534 populates the data saved for that pump user's pump 100 into the user interface 542. In an alternative embodiment, the computer 534 is loaded with a menu in which the name of each pump user having stored data is included as a menu item. Selecting the name/menu item causes the computer 534 to populate the user interface 542 with data.

The various embodiments described above are provided by way of illustration only and should not be construed to limit the invention. Those skilled in the art will readily recognize various modifications and changes that may be made to the present invention without following the example embodiments and applications illustrated and described herein, and without departing from the true spirit and scope of the present invention, which is set forth in the following claims.

The invention claimed is:

1. A method of regulating blood glucose levels using an insulin pump, the method comprising:
   receiving a current blood glucose level at an insulin pump;
   determining whether the current blood glucose level is above a threshold value with the insulin pump; and
   upon determining that the current blood glucose level is above the threshold, automatically calculating a revised correction bolus value with the pump from a preexisting correction bolus value, both the revised correction bolus value and the preexisting correction bolus value being calculated based upon the current blood glucose level.

2. The method of claim 1, further comprising delivering the revised correction bolus to a user.

3. The method of claim 1, wherein calculating the revised correction bolus value includes altering a correction bolus calculation factor according to at least one predefined rule based on the threshold value and calculating the revised correction bolus value using the altered correction bolus calculation factor.

4. The method of claim 1, wherein calculating the revised correction bolus value includes increasing the correction bolus value by a predefined amount based on the threshold value.

5. The method of claim 4, wherein the predefined amount is a percentage of the preexisting correction bolus value.

6. The method of claim 5, further comprising prompting a user to input the percentage and the threshold value to define the rule.

7. The method of claim 6, further comprising prompting the user to define a plurality of rules.

8. The method of claim 6, wherein the pump prompts the user.

9. The method of claim 6, wherein a computing system interfaced with the pump prompts the user.

10. The method of claim 4, further comprising displaying the predefined amount on a display of the insulin pump.

11. The method of claim 1, further comprising displaying the revised correction bolus value on a display of the insulin pump.

12. The method of claim 1, wherein calculating a revised correction bolus value is further based on an insulin absorption model selected from a plurality of insulin absorption models.

13. An insulin pump comprising:
   a pump mechanism;
   a memory configured to store one or more blood glucose levels;
   a programmable circuit arranged to control the pump mechanism and operatively connected to the memory, the programmable circuit programmed to:
   receive a current blood glucose level;
   determine whether the current blood glucose level is above a threshold value; and
   upon determining that the current blood glucose level is above the threshold value, automatically calculate a revised correction bolus value from a preexisting correction bolus value, both the revised correction bolus value and the preexisting correcting bolus value being calculated based upon the current blood glucose level.

14. The insulin pump of claim 13, wherein the programmable circuit is further programmed to deliver the revised correction bolus to a user.

15. The insulin pump of claim 13, wherein calculating the revised correction bolus value includes altering a correction bolus calculation factor according to at least one predefined rule based on the threshold value.

16. The insulin pump of claim 15, wherein the programmable circuit is further programmed to calculate the revised correction bolus value using the altered correction bolus calculation factor.

17. The insulin pump of claim 13, wherein calculating the revised correction bolus value includes increasing the correction bolus value by a predefined amount based on the threshold value.

18. The insulin pump of claim 17, wherein the predefined amount is a percentage of the preexisting correction bolus value.

19. The insulin pump of claim 18, wherein the programmable circuit is further programmed to prompt a user to input the percentage and the threshold value to define a rule.

20. The insulin pump of claim 19, wherein the programmable circuit is further programmed to prompt the user to define a plurality of rules.

21. An insulin pump comprising: a pump mechanism;
a memory configured to store one or more rules, each rule including a threshold value and a percentage;
a programmable circuit arranged to control the pump mechanism and operatively connected to the memory, the programmable circuit programmed to:
prompt a user to input the threshold value and the percentage for at least one rule;
receive a current blood glucose level;
determine whether the current blood glucose level is above the threshold value;
upon determining that the current blood glucose level is above the threshold value, automatically alter a pre-existing correction bolus calculation factor representing an amount the user's blood glucose level drops for each unit of delivered insulin according to the at least one rule to define an altered correction bolus calculation factor;
calculate a correction bolus value based upon the altered correction bolus calculation factor; and
deliver the correction bolus to the user.

* * * * *